(12) United States Patent
Hatakeyama et al.

(10) Patent No.: US 10,156,788 B2
(45) Date of Patent: Dec. 18, 2018

(54) RESIST UNDERLAYER FILM COMPOSITION, PATTERNING PROCESS, AND COMPOUND

(71) Applicant: SHIN-ETSU CHEMICAL CO., LTD., Tokyo (JP)

(72) Inventors: Jun Hatakeyama, Jyoetsu (JP); Daisuke Kori, Jyoetsu (JP); Tsutomu Ogihara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 10 days.

(21) Appl. No.: 15/198,369

(22) Filed: Jun. 30, 2016

(65) Prior Publication Data

US 2017/0018436 A1    Jan. 19, 2017

(30) Foreign Application Priority Data

Jul. 14, 2015   (JP) .................................. 2015-140401

(51) Int. Cl.

| | |
|---|---|
| *G03F 7/004* | (2006.01) |
| *G03F 7/20* | (2006.01) |
| *G03F 7/38* | (2006.01) |
| *C07C 303/32* | (2006.01) |
| *C07C 309/04* | (2006.01) |
| *C07C 309/06* | (2006.01) |
| *C07C 309/12* | (2006.01) |
| *C07C 309/17* | (2006.01) |
| *C07C 309/19* | (2006.01) |
| *C07D 327/02* | (2006.01) |
| *C07D 327/04* | (2006.01) |
| *C07D 327/06* | (2006.01) |
| *C07D 333/46* | (2006.01) |
| *C07D 335/02* | (2006.01) |
| *C07D 337/04* | (2006.01) |
| *G03F 7/11* | (2006.01) |
| *C07C 39/17* | (2006.01) |
| *C07D 493/10* | (2006.01) |
| *C08G 8/10* | (2006.01) |
| *C07C 49/665* | (2006.01) |
| *C08G 8/02* | (2006.01) |
| *C08G 8/20* | (2006.01) |
| *C08G 8/36* | (2006.01) |
| *C08L 61/06* | (2006.01) |
| *C08L 61/12* | (2006.01) |
| *G03F 7/075* | (2006.01) |
| *G03F 7/09* | (2006.01) |
| *H01L 21/033* | (2006.01) |
| *H01L 21/311* | (2006.01) |

(52) U.S. Cl.
CPC ............... *G03F 7/11* (2013.01); *C07C 39/17* (2013.01); *C07C 49/665* (2013.01); *C07D 493/10* (2013.01); *C08G 8/02* (2013.01); *C08G 8/10* (2013.01); *C08G 8/20* (2013.01); *C08G 8/36* (2013.01); *C08L 61/06* (2013.01); *C08L 61/12* (2013.01); *G03F 7/0752* (2013.01); *G03F 7/091* (2013.01); *G03F 7/094* (2013.01); *H01L 21/0332* (2013.01); *C07C 2603/52* (2017.05); *H01L 21/31116* (2013.01); *H01L 21/31138* (2013.01)

(58) Field of Classification Search
CPC ............ G03F 7/11; C08G 8/10; C07C 49/665
USPC ...................... 430/271.1, 326, 317, 318, 323
See application file for complete search history.

(56) References Cited

U.S. PATENT DOCUMENTS

| | | | |
|---|---|---|---|
| 6,013,416 A | 1/2000 | Nozaki et al. | |
| 6,312,867 B1 | 11/2001 | Kinsho et al. | |
| 7,973,203 B2 * | 7/2011 | Buesing | ............... C07C 2/861 257/40 |
| 2004/0241577 A1 | 12/2004 | Hatakeyama et al. | |
| 2004/0259037 A1 | 12/2004 | Hatakeyama et al. | |
| 2006/0014106 A1 | 1/2006 | Hatakeyama et al. | |
| 2006/0019195 A1 | 1/2006 | Hatakeyama et al. | |
| 2006/0204891 A1 | 9/2006 | Hatakeyama | |
| 2006/0234158 A1 | 10/2006 | Hatakeyama | |
| 2007/0122740 A1 | 5/2007 | Hatakeyama et al. | |
| 2007/0275325 A1 | 11/2007 | Hatakeyama et al. | |
| 2008/0038662 A1 | 2/2008 | Hatakeyama et al. | |
| 2008/0227037 A1 | 9/2008 | Hatakeyama et al. | |
| 2010/0047709 A1 | 2/2010 | Echigo et al. | |
| 2010/0099044 A1 | 4/2010 | Hatakeyama et al. | |
| 2010/0104977 A1 | 4/2010 | Hatakeyama et al. | |
| 2014/0370444 A1* | 12/2014 | Rahman | ............... G03F 7/0757 430/311 |

FOREIGN PATENT DOCUMENTS

| | | |
|---|---|---|
| CN | 1711301 A | 12/2005 |
| CN | 104003846 A | 8/2014 |
| JP | H05-4822 B2 | 1/1993 |
| JP | H09-73173 A | 3/1997 |
| JP | 2000-336121 A | 12/2000 |
| JP | 2001-226430 A | 8/2001 |
| JP | 2004-205658 A | 7/2004 |
| JP | 2004-205676 A | 7/2004 |
| JP | 2004-205685 A | 7/2004 |
| JP | 2004-271838 A | 9/2004 |
| JP | 2004-354554 A | 12/2004 |

(Continued)

OTHER PUBLICATIONS

Aug. 23, 2017 Office Action issued in Taiwanese Application No. 1015121867.

*Primary Examiner* — John S Chu
(74) *Attorney, Agent, or Firm* — Oliff PLC

(57) ABSTRACT

The present invention provides a resist underlayer film composition for lithography, containing a compound having an indenofluorene structure. This resist underlayer film composition is excellent in filling property, generates little outgas, and has high heat resistance.

8 Claims, 3 Drawing Sheets

(56) References Cited

FOREIGN PATENT DOCUMENTS

| | | | |
|---|---|---|---|
| JP | 2005-010431 | A | 1/2005 |
| JP | 2005-049810 | A | 2/2005 |
| JP | 2005-114921 | A | 4/2005 |
| JP | 2005-128509 | A | 5/2005 |
| JP | 2005-250434 | A | 9/2005 |
| JP | 2006-053543 | A | 2/2006 |
| JP | 2006-096848 | A | 4/2006 |
| JP | 2006-227391 | A | 8/2006 |
| JP | 2006-259249 | A | 9/2006 |
| JP | 2006-259482 | A | 9/2006 |
| JP | 2006-285095 | A | 10/2006 |
| JP | 2006-293207 | A | 10/2006 |
| JP | 2006-293298 | A | 10/2006 |
| JP | 2007-140461 | A | 6/2007 |
| JP | 2007-171895 | A | 7/2007 |
| JP | 2007-199653 | A | 8/2007 |
| JP | 2007-316282 | A | 12/2007 |
| JP | 2008-026600 | A | 2/2008 |
| JP | 2008-065303 | A | 3/2008 |
| JP | 2008-096684 | A | 4/2008 |
| JP | 2008-116677 | A | 5/2008 |
| JP | 2008-145539 | A | 6/2008 |
| JP | 2008-257188 | A | 10/2008 |
| JP | 2010-122656 | A | 6/2010 |
| JP | 2010-134437 | A | 6/2010 |
| JP | 2010-160189 | A | 7/2010 |
| JP | 2010-170013 | A | 8/2010 |
| JP | 2010-271654 | A | 12/2010 |
| WO | 2004/041901 | A1 | 5/2004 |

\* cited by examiner

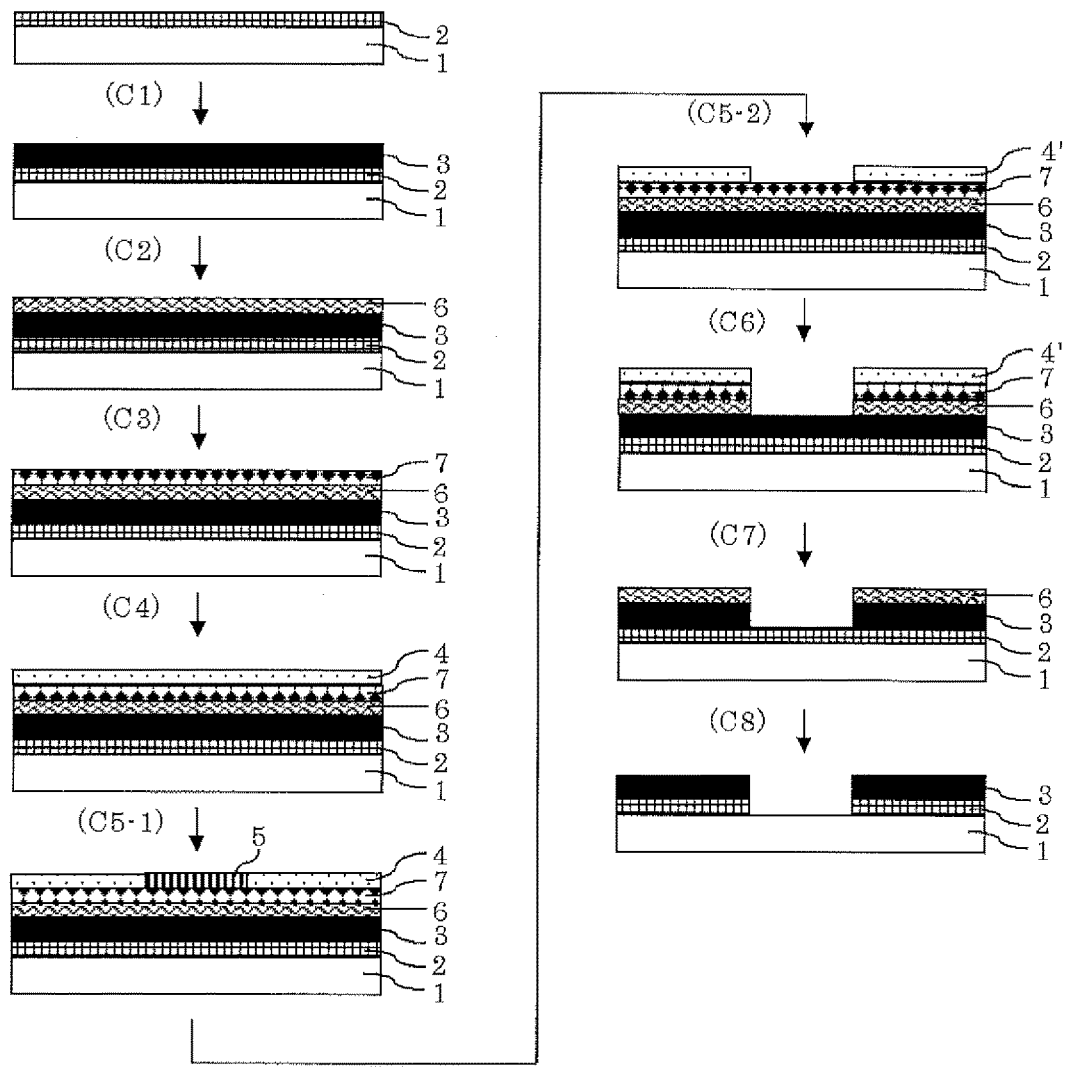

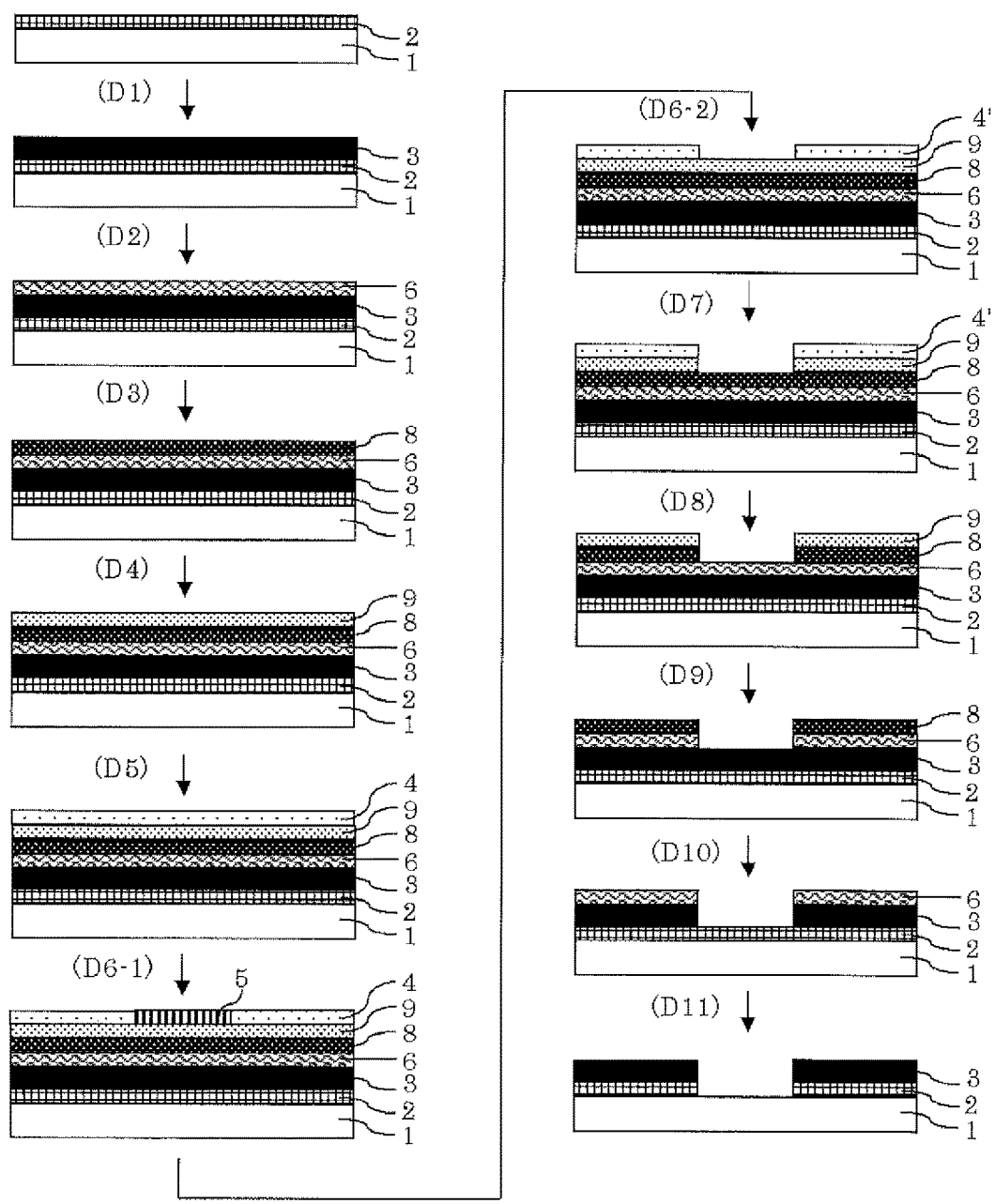

RESIST UNDERLAYER FILM COMPOSITION, PATTERNING PROCESS, AND COMPOUND

BACKGROUND OF THE INVENTION

Field of the Invention

The present invention relates to a resist underlayer film composition for patterning by a multilayer resist process, a patterning process using the resist underlayer film composition, and a novel compound usable in the resist underlayer film composition.

Description of the Related Art

In recent years, problems of device operation failure due to an increase in gate leakage current arise with miniaturization and higher speed of transistors. Although a longer channel (a longer distance between a source and a drain) reduces the leakage current, this makes response speed lower and the transistor larger.

Fin-field effect transistor (Fin-FIT), which uses a three-dimensional gate, has been suggested to achieve conflict aims of miniaturization and a reduction in leakage current. The three-dimensional gate makes the channel long and enables the reduction in leakage current with miniaturization, higher speed, and lower power consumption. Fin-FIT was established based on a three-dimensional transistor shown in FIG. 2 of Patent Document 1. This great suggestion foresaw the problems decades ago and provided its solution.

Manufacture of the three-dimensional devices such as three-dimensional transistors uses substrates having concavity and convexity (three-dimensional device substrates), so that a top-down processing typified by lithography, which has been widely used for forming two-dimensional patterns, cannot be applied to the manufacture of the three-dimensional devices as it is used for forming two-dimensional patterns. Thus, a novel process and a material suited to the process have been desired for the manufacture of the three-dimensional transistors typified by Fin-FET.

The manufacture of the three-dimensional devices by lithography requires planarizing a photoresist film to cover a decrease in focus margin with miniaturization. On the other hand, the three-dimensional device substrates tend to have gaps with higher aspect ratio. To fill the gaps, a high technique for planarizing the photoresist film and the three-dimensional substrate has been required.

One example of such a method for manufacturing three-dimensional devices by lithography is a tri-layer (3-layer) process in which the gaps of the three-dimensional device substrate are planarized by an underlayer film (resist underlayer film) formed by spin coating, a silicon-containing middle layer film is formed thereon, and a photoresist film is formed thereon. In this method, the underlayer film needs excellent filling property.

Such manufacture of the three-dimensional devices by lithography requires forming a pattern with high aspect ratio by dry etching process. Thus, the underlayer film also needs high dry etching resistance, as well as filling property. Furthermore, the middle layer film on the underlayer film also needs high dry etching resistance, so that a metallic middle layer film formed by CVD or sputtering, which has higher dry etching resistance than a middle layer film formed by spin coating, is often selected as the middle layer film. Because the middle layer film usually requires 300° C. or higher temperature to be formed by CVD or sputtering, the underlayer film also needs high heat resistance to withstand this temperature.

A bisnaphtholfluorene novolak resin disclosed in Patent Document 2 is a high heat-resistant resin having a heat resistance of 500° C. Adding this bisnaphtholfluorene novolak resin and monomer components (bisnaphtholfluorene compounds) to an underlayer film composition enables the underlayer film composition to have increased flowability during baking at high temperature, thereby improving filling property. However, when the monomer components are added, outgas is generated in baking at high temperature and then adheres to a plate above a hot plate. This outgas can drop to the substrate and causes defects.

The generation of outgas can be prevented by crosslinking of the film. Thus, when a phenol compound, which has higher crosslinking rate and lower crosslinking temperature than a naphthol compound, is used in the underlayer film composition, the outgas generation is reduced compared with the case of using a naphthol compound. However, crosslinking reduces flowability of the underlayer film composition, so that if the phenol compound is used in the underlayer film composition, the underlayer film composition may crosslink at low temperature before flowing, thereby lowering filling property. Moreover, although filling property is generally improved by crosslinking at higher temperature, the phenol compound has low heat resistance disadvantageously.

PRIOR ART DOCUMENTS

Patent Documents

[Patent Document 1] Japanese Examined Patent Publication No. H05-004822

[Patent Document 2] Japanese Patent Laid-Open Publication No. 2010-122656

SUMMARY OF THE INVENTION

As mentioned above, it has been desired to develop a resist underlayer film composition that is excellent in filling property, generates little outgas, and has high heat resistance. To improve filling property, many low-molecular weight components (monomer components) having high crosslinking temperature need to be added. However, the more low-molecular weight components are added, the more outgas is generated due to evaporation of the low-molecular weight components. In other words, there is a trade-off relationship between the improvement in filling property and the reduction in outgas generation. Moreover, compounds having a fluorene structure, which has been used in the underlayer film composition, has high heat resistance, but causes outgas due to its small molecular weight. In other words, there is also a trade-off relationship between the improvement in heat resistance and the reduction in outgas generation.

It is an object of the present invention to provide a resist underlayer film composition that can overcome such trade-off relationships, is excellent in filling property, generates little outgas, and has high heat resistance; a patterning process using the same; and a novel compound that is suitable for such a resist underlayer film composition.

To achieve this object, the present invention provides a resist underlayer film composition for lithography, comprising a compound having an indenofluorene structure.

Such a resist underlayer film composition is excellent in filling property, generates little outgas, and has high heat resistance.

The compound having an indenofluorene structure is preferably one or more compounds selected from the group consisting of: a compound X shown by the formula (1); a compound Y in which a plurality of the compounds X is bonded directly or via an arylene group having 6 to 28 carbon atoms and optionally containing an alkylene group having 1 to 10 carbon atoms; and a condensate obtained by a condensation of a material containing the compound X and/or the compound Y,

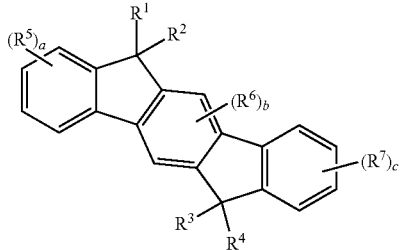

(1)

wherein $R^1$, $R^2$, $R^3$, and $R^4$ each represent a hydrogen atom, a substituted or unsubstituted hydroxyl group or carboxyl group, a linear, branched, or cyclic alkyl group having 1 to 16 carbon atoms, a linear, branched, or cyclic alkenyl group having 2 to 10 carbon atoms, a linear, branched, or cyclic alkynyl group having 2 to 10 carbon atoms, an aryl group having 6 to 35 carbon atoms, or a carbazole group that may be substituted with an alkyl group, an alkenyl group, or an alkynyl group, in which the alkyl group, the alkenyl group, the alkynyl group, and the aryl group may contain a hydroxyl group, an alkoxy group, a carboxyl group, an alkoxycarbonyl group, an acyloxy group, a sulfonate ester group, an oxirane group, an oxetane group, an acid-labile group, an ether group, and/or a thiol group; $R^1$ and $R^3$ may bond to $R^2$ and $R^4$ respectively via an oxygen atom to form a cyclic ether structure; a combination of $R^1$ and $R^2$ and a combination of $R^3$ and $R^4$ may each form a carbonyl group; $R^5$, $R^6$, and $R^7$ each represent a halogen atom, an amino group, a linear, branched, or cyclic alkyl group having 1 to 16 carbon atoms, a linear, branched, or cyclic alkenyl group having 2 to 10 carbon atoms, a linear, branched, or cyclic alkynyl group having 2 to 10 carbon atoms, or an aryl group having 6 to 12 carbon atoms; and "a", "b", and "c" each represent an integer of 0 to 2.

Such a resist underlayer film composition is more excellent in filling property, generates less outgas, and has higher heat resistance.

The compound X is preferably a compound shown by the formula (2),

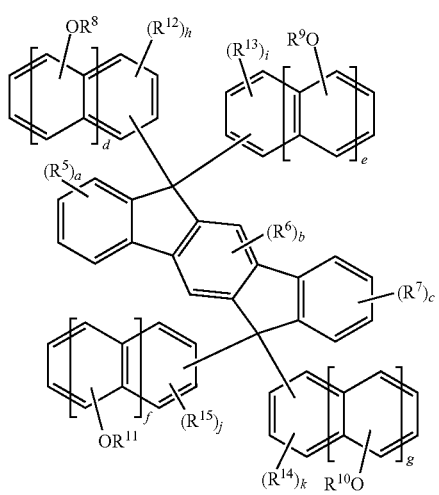

(2)

wherein $R^5$, $R^6$, $R^7$, "a", "b" and "c" are as defined above; $R^8$, $R^9$, $R^{10}$, and $R^{11}$ each represent a hydrogen atom, a linear, branched, or cyclic alkyl group having 1 to 16 carbon atoms, a linear, branched, or cyclic alkenyl or alkynyl group having 2 to 10 carbon atoms, an aryl group having 6 to 12 carbon atoms, a linear, branched, or cyclic acyl group having 1 to 16 carbon atoms, an acid-labile group, a group having an oxirane structure, a group having an oxetane structure, or a sulfa group; $R^{12}$, $R^{13}$, $R^{14}$, and $R^{15}$ each represent a hydroxyl group, an acyloxy group, or a linear, branched, or cyclic alkyl group having 1 to 16 carbon atoms; $R^{12}$ and $R^{14}$ may bond to $R^{13}$ and $R^{15}$ respectively via an oxygen atom to form a cyclic ether structure; "d", "e", "f", and "g" each represent 0 or 1; and "h", "i", "j", and "k" each represent an integer of 0 to 5.

Such a compound enables the improvement in filling property, the reduction in outgas, and the improvement in heat resistance to be achieved with particularly good balance.

The condensate is preferably a resin having a repeating unit shown by the formula (3),

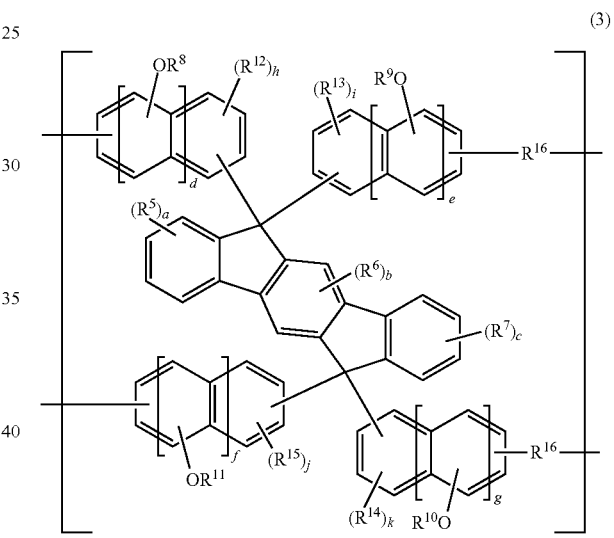

(3)

wherein $R^5$, $R^6$, $R^7$, "a", "b" and "c" are as defined above; $R^8$, $R^9$, $R^{10}$, and $R^{11}$ each represent a hydrogen atom, a linear, branched, or cyclic alkyl group having 1 to 16 carbon atoms, a linear, branched, or cyclic alkenyl or alkynyl group having 2 to 10 carbon atoms, an aryl group having 6 to 12 carbon atoms, a linear, branched, or cyclic acyl group having 1 to 16 carbon atoms, an acid-labile group, a group having an oxirane structure, a group having an oxetane structure, or a sulfo group; $R^{12}$, $R^{13}$, $R^{14}$, and $R^{15}$ each represent a hydroxyl group, an acyloxy group, or a linear, branched, or cyclic alkyl group having 1 to 16 carbon atoms; $R^{12}$ and $R^{14}$ may bond to $R^{13}$ and $R^{15}$ respectively via an oxygen atom to form a cyclic ether structure; "d", "e", "f", and "g" each represent 0 or 1; "h", "i", "j", and "k" each represent an integer of 0 to 5; $R^{16}$ represents a single bond or a linear, branched, or cyclic alkylene group having 1 to 8 carbon atoms and optionally containing a linear, branched, or cyclic alkenyl group having 2 to 10 carbon atoms, an aryl group having 6 to 14 carbon atoms, an ether group, a thiol group, a thioether group, an ester group, a lactone ring, a nitro group, or a substituted or unsubstituted hydroxyl group or carboxyl group.

Such a resin enables outgas generation to be further reduced.

The resist underlayer film composition preferably further comprises an organic solvent.

When the organic solvent is contained, coating property is improved.

The resist underlayer film composition preferably further comprises an acid generator and/or a crosslinking agent.

When the acid generator and/or the crosslinking agent are contained, crosslinking curing reaction of the resist underlayer film composition is promoted.

Furthermore, the present invention provides a patterning process for forming a pattern in a substrate by lithography, comprising the steps of: (A1) forming a resist underlayer film on the substrate from the above resist underlayer film composition; (A2) forming a photoresist film on the resist underlayer film; (A3) forming a photoresist pattern by subjecting the photoresist film to exposure and development; (A4) transferring the pattern to the resist underlayer film by dry etching using the photoresist pattern as a mask; and (A5) processing the substrate by using the resist underlayer film having the transferred pattern as a mask.

Furthermore, the present invention provides a patterning process for forming a pattern in a substrate by lithography, comprising the steps of: (B1) forming a resist underlayer film on the substrate from the above resist underlayer film composition; (B2) forming a metallic middle layer film containing an element selected from the group consisting of silicon, titanium, zirconium, hafnium, tungsten, aluminum, germanium, tin, and chromium on the resist underlayer film; (B3) forming a photoresist film on the metallic middle layer film; (B4) forming a photoresist pattern by subjecting the photoresist film to exposure and development; (B5) transferring the pattern to the metallic middle layer film by dry etching using the photoresist pattern as a mask; (B6) transferring the pattern to the resist underlayer film by dry etching using the metallic middle layer film having the transferred pattern as a mask; and (B7) processing the substrate by using the resist underlayer film having the transferred pattern as a mask.

Furthermore, the present invention provides a patterning process for forming a pattern in a substrate by lithography, comprising the steps of: (C1) forming a resist underlayer film on the substrate from the above resist underlayer film composition; (C2) forming a metallic middle layer film containing an element selected from the group consisting of silicon, titanium, zirconium, hafnium, tungsten, aluminum, germanium, tin, and chromium on the resist underlayer film; (C3) forming an organic antireflective film on the metallic middle layer film; (C4) forming a photoresist film on the organic antireflective film; (C5) forming a photoresist pattern by subjecting the photoresist film to exposure and development; (C6) transferring the pattern to the organic antireflective film and the metallic middle layer film by dry etching using the photoresist pattern as a mask; (C7) transferring the pattern to the resist underlayer film by dry etching using the metallic middle layer film having the transferred pattern as a mask; and (C8) processing the substrate by using the resist underlayer film having the transferred pattern as a mask.

Furthermore, the present invention provides a patterning process for forming a pattern in a substrate by lithography, comprising the steps of: (D1) forming a resist underlayer film on the substrate from the above resist underlayer film composition; (D2) forming a metallic middle layer film containing an element selected from the group consisting of silicon, titanium, zirconium, hafnium, tungsten, aluminum, germanium, tin, and chromium on the resist underlayer film; (D3) forming a hydrocarbon film on the metallic middle layer film; (D4) forming a silicon-containing film on the hydrocarbon film; (D5) forming a photoresist film on the silicon-containing film; (D6) forming a photoresist pattern by subjecting the photoresist film to exposure and development; (D7) transferring the pattern to the silicon-containing film by dry etching using the photoresist pattern as a mask; (D8) transferring the pattern to the hydrocarbon film by dry etching using the silicon-containing film having the transferred pattern as a mask; (D9) transferring the pattern to the metallic middle layer film by dry etching using the hydrocarbon film having the transferred pattern as a mask; (D10) transferring the pattern to the resist underlayer film by dry etching using the metallic middle layer film having the transferred pattern as a mask; and (D11) processing the substrate by using the resist underlayer film having the transferred pattern as a mask.

Thus, the inventive resist underlayer film composition can be suitably used for patterning processes by multilayer resist processes such as 2-layer process, 3-layer process, 4-layer process, and 5-layer process. Moreover, as mentioned above, the inventive resist underlayer film composition, which is excellent in filling property, generates little outgas, and has high heat resistance, can significantly reduce defects in fine processing in a process of manufacturing semiconductor apparatuses or the like.

Furthermore, the present invention provides a compound shown by the formula (4),

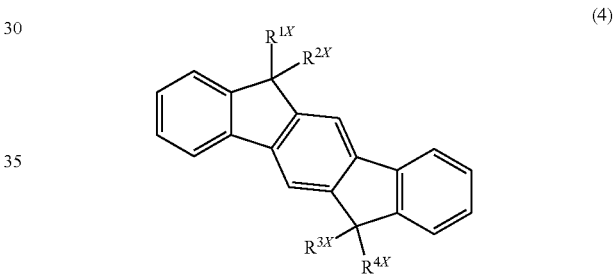

wherein $R^{1X}$, $R^{2X}$, $R^{3X}$, and $R^{4X}$ each represent a naphthol group, a glycidoxynaphthyl group, or a phenol group; and $R^{1X}$ and $R^{3X}$ may bond to $R^{2X}$ and $R^{4X}$ respectively via an oxygen atom to form a cyclic ether structure.

Such a compound can provide a resist underlayer film composition that is excellent in filling property, generate little outgas, and has high heat resistance by using the compound in the underlayer film composition.

The compound having an indenofluorene structure (particularly, an indeno[1,2-b]fluorene structure), which is contained in the inventive resist underlayer film composition, not only has larger molecular weight than the compound having a fluorene structure used in the conventional resist underlayer film composition, but also has twice as much crosslinking points as the conventional one. Thus, the inventive resist underlayer film composition containing such a compound generates little outgas even if only monomer components are contained therein or many monomer components are added thereto, is excellent in filling property, prevents pattern wiggling at dry etching due to high crosslinking density, and has high heat resistance. In other words, the inventive resist underlayer film composition can improve all properties including filling property, outgas reduction, and heat resistance, more than ever. Moreover, the inventive patterning process using the inventive resist underlayer film composition can significantly reduce defects in fine processing in a process of manufacturing semiconductor apparatuses or the like. Moreover, the inventive compound is particularly useful for the inventive resist underlayer film composition.

BRIEF DESCRIPTION OF THE DRAWINGS

FIG. 3 is an explanatory view showing an example of the patterning process by 4-layer process of the present invention; and FIG. 4 is an explanatory view showing an example of the patterning process by 5-layer process of the present invention.

DETAILED DESCRIPTION OF THE PREFERRED EMBODIMENTS

Figure 1:
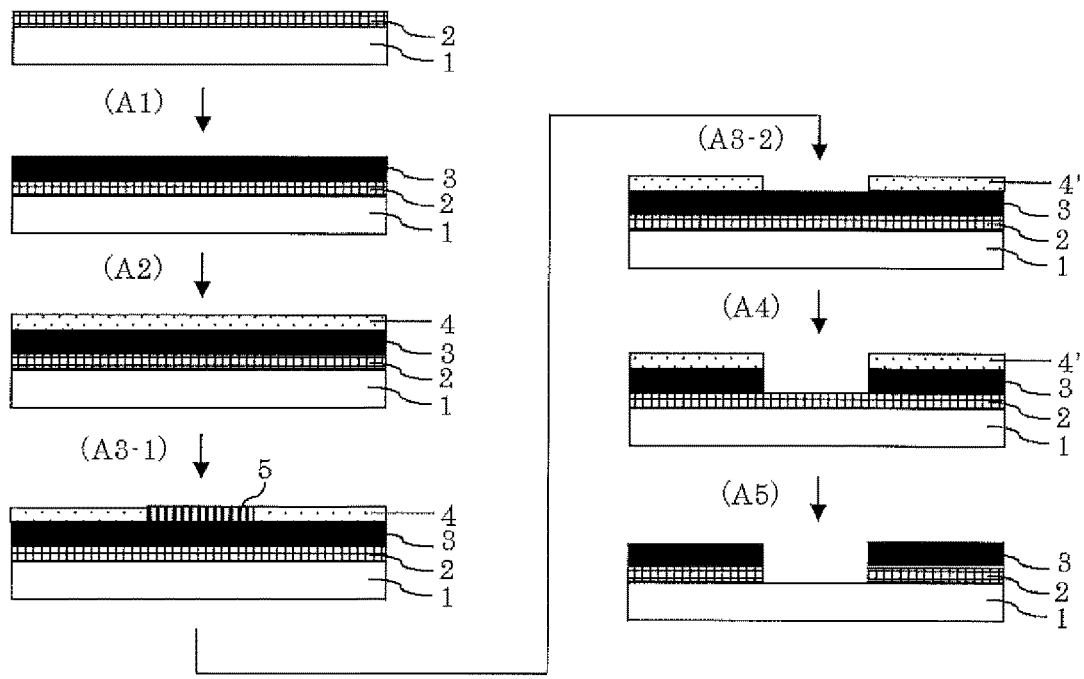
FIG. 1 is an explanatory view showing an example of the patterning process by 2-layer process of the present invention.

The present inventors have earnestly studied to develop a resist underlayer film composition that is excellent in filling property, generates little outgas, and has high heat resistance. They consequently found that a resist underlayer film composition containing a compound having an indenofluorene structure (particularly, an indeno[1,2-b]fluorene structure), which combines two fluorene units sharing a benzene ring, is excellent in the above properties, thereby bringing the present invention to completion.

That is, the present invention is a resist underlayer film composition for lithography, comprising a compound having an indenofluorene structure. The compound having an indenofluorene structure is preferably one or more compounds selected from the group consisting of: a compound X shown by the formula (1); a compound Y in which a plurality of the compounds X is bonded directly or via an arylene group having 6 to 28 carbon atoms and optionally containing an alkylene group having 1 to 10 carbon atoms; and a condensate obtained by a condensation of a material containing the compound X and/or the compound Y,

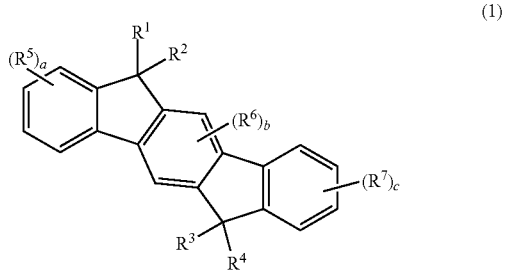

(1)

wherein $R^1$, $R^2$, $R^3$, and $R^4$ each represent a hydrogen atom, a substituted or unsubstituted hydroxyl group or carboxyl group, a linear, branched, or cyclic alkyl group having 1 to 16 carbon atoms, a linear, branched, or cyclic alkenyl group having 2 to 10 carbon atoms, a linear, branched, or cyclic alkynyl group having 2 to 10 carbon atoms, an aryl group having 6 to 35 carbon atoms, or a carbazole group that may be substituted with an alkyl group, an alkenyl group, or an alkynyl group, in which the alkyl group, the alkenyl group, the alkynyl group, and the aryl group may contain a hydroxyl group, an alkoxy group, a carboxyl group, an alkoxycarbonyl group, an acyloxy group, a sulfonate ester group, an oxirane group, an oxetane group, an acid-labile group, an ether group, and/or a thiol group; $R^1$ and $R^3$ may bond to $R^2$ and $R^4$ respectively via an oxygen atom to form a cyclic ether structure; a combination of $R^1$ and $R^2$ and a combination of $R^3$ and $R^4$ may each form a carbonyl group; $R^5$, $R^6$, and $R^7$ each represent a halogen atom, an amino group, a linear, branched, or cyclic alkyl group having 1 to 16 carbon atoms, a linear, branched, or cyclic alkenyl group having 2 to 10 carbon atoms, a linear, branched, or cyclic alkynyl group having 2 to 10 carbon atoms, or an aryl group having 6 to 12 carbon atoms; and "a", "b", and "c" each represent an integer of 0 to 2.

In the following, the present invention will be described in detail, but the present invention is not limited thereto. Herein, the aforementioned compound X, compound Y, and condensate are collectively referred to as "indeno[1,2-b]fluorene compound".

<Compound>

The present invention provides a compound shown by the formula (4),

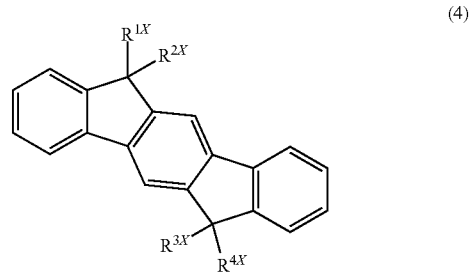

(4)

wherein $R^{1X}$, $R^{2X}$, $R^{3X}$, and $R^{4X}$ each represent a naphthol group, a glycidoxynaphthyl group, or a phenol group; and $R^{1X}$ and $R^{3X}$ may bond to $R^{2X}$ and $R^{4X}$ respectively via an oxygen atom to form a cyclic ether structure.

Illustrative examples of the compound are shown below.

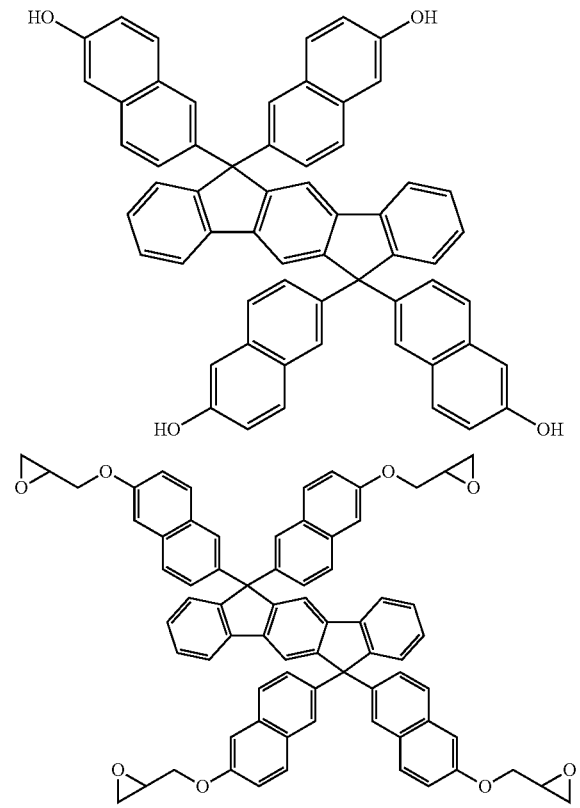

-continued

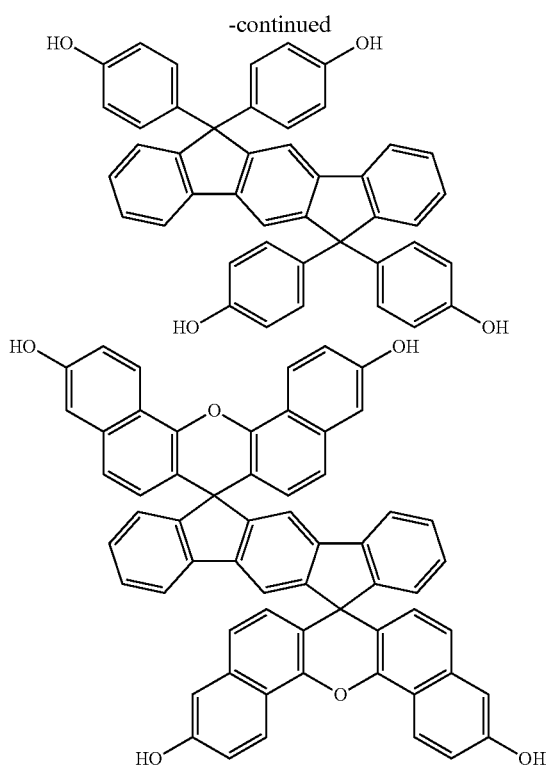

Such a compound enables a resist underlayer film using this compound to have excellent filling property and high heat resistance and to generate little outgas. In other words, the inventive compound is particularly suitable for the inventive resist underlayer film composition described later.

<Resist Underlayer Film Composition>

The inventive resist underlayer film composition contains a compound having an indenofluorene structure (particularly, an indeno[1,2-b]fluorene structure) as an essential component. More specifically, the composition preferably contains one or more of the following three compounds. Of course, the composition may contain two or all the three compounds.

(a) Compound X shown by the formula (1)

(b) Compound Y in which multiple compounds X are bonded directly or via an arylene group having 6 to 28 carbon atoms and optionally containing an alkylene group having 1 to 10 carbon atoms (c) Condensate obtained by a condensation of a material containing the compound X and/or the compound Y

[Compound X]

The indeno[1,2-b]fluorene compound contained in the inventive resist underlayer film composition may be the compound X shown by the formula (1). Illustrative examples of the compound X include the following compounds, although it is not limited thereto.

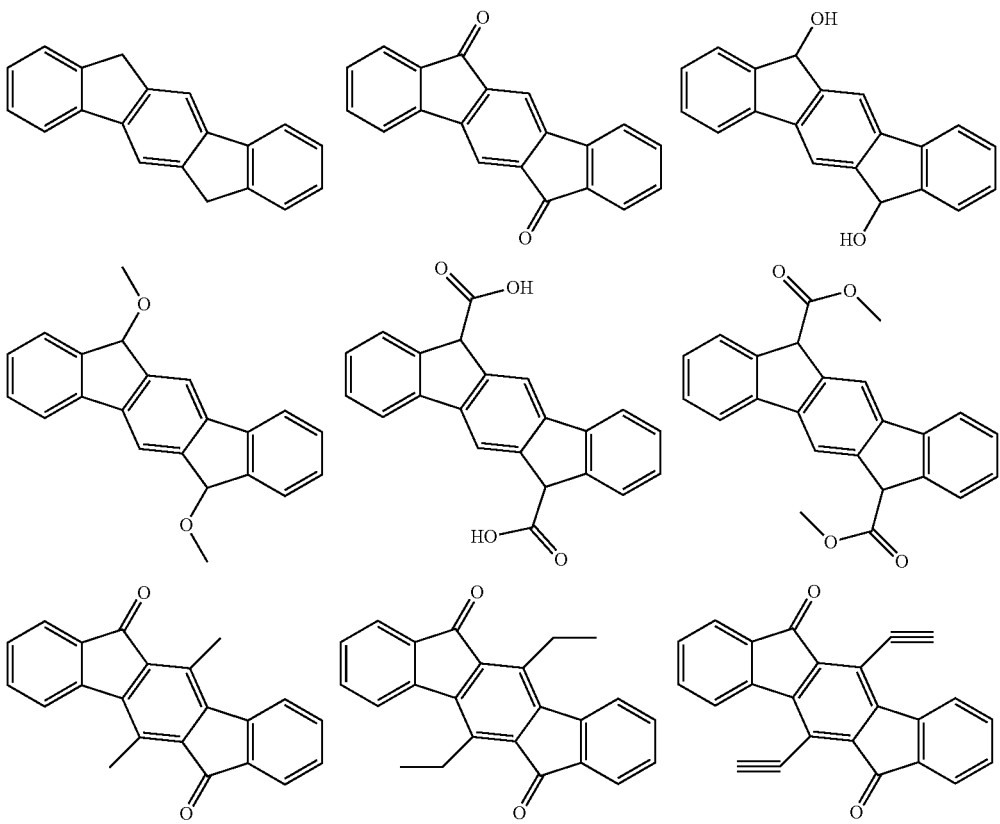

-continued
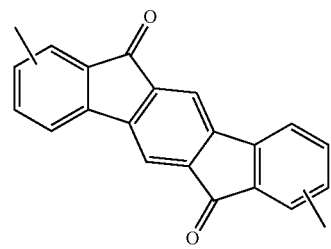 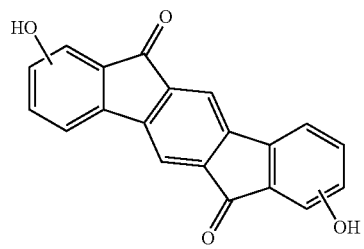 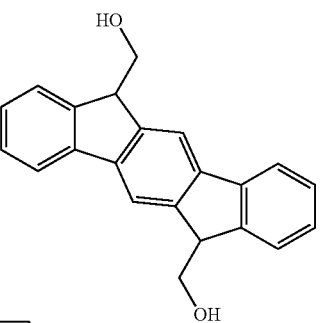
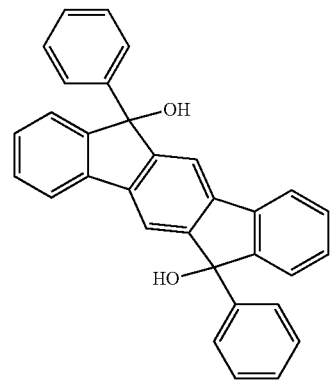 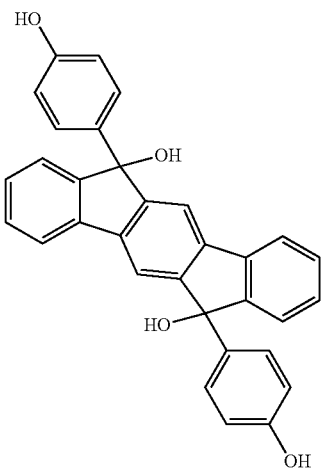 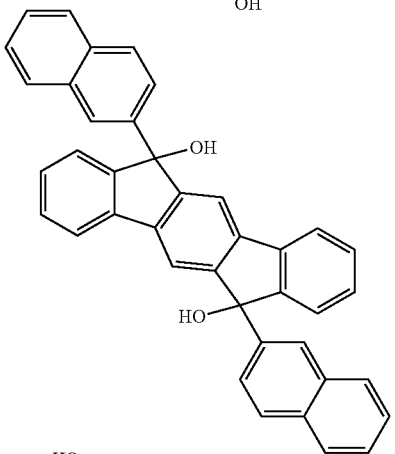
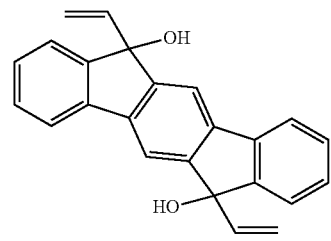 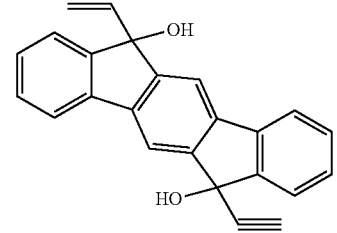 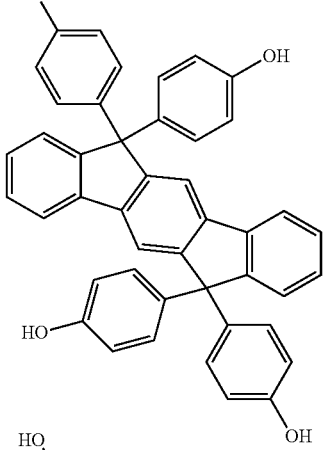
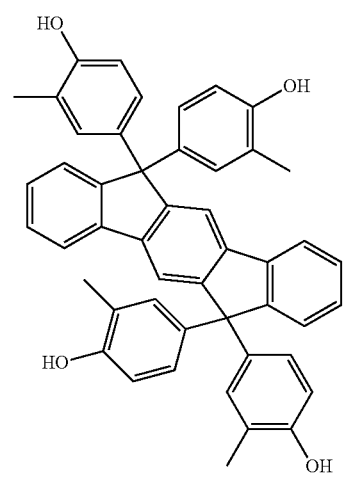 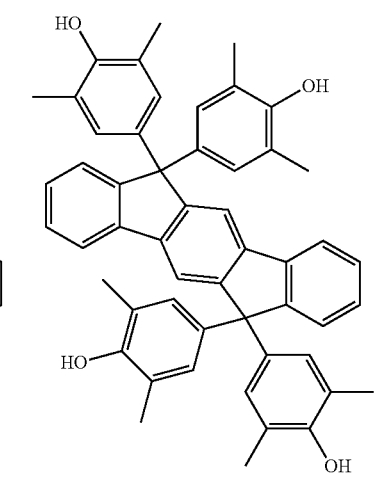 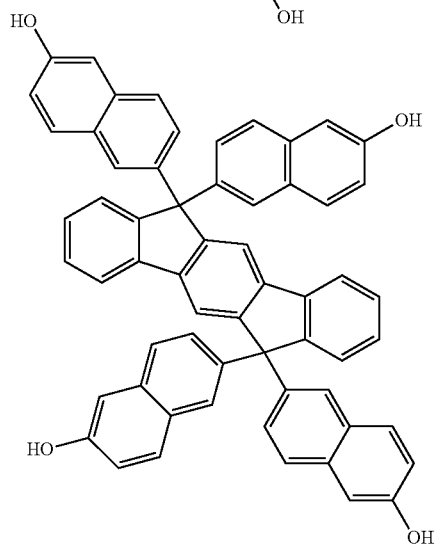

-continued
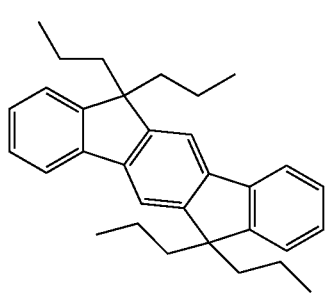
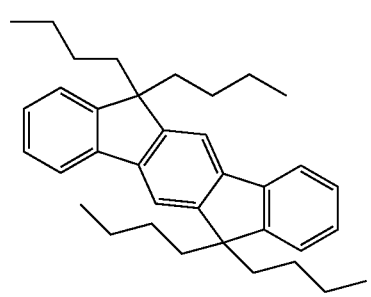
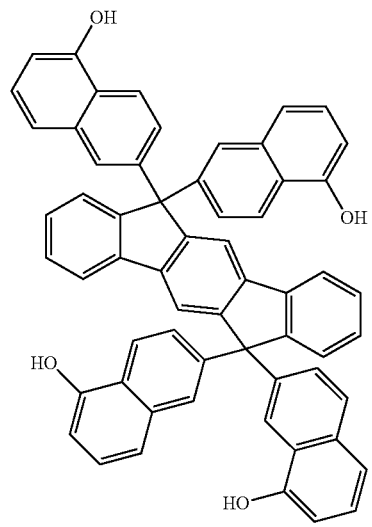
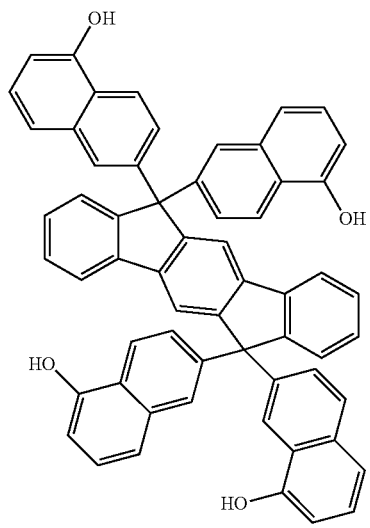
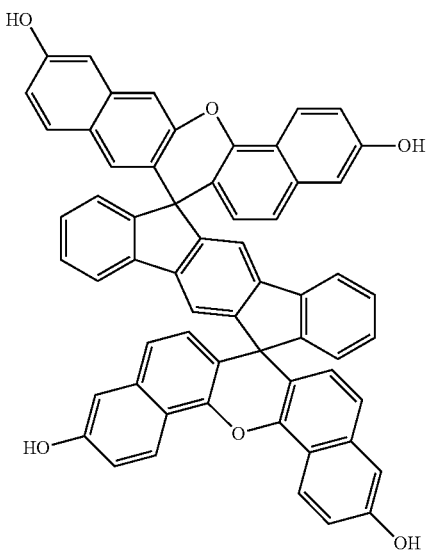
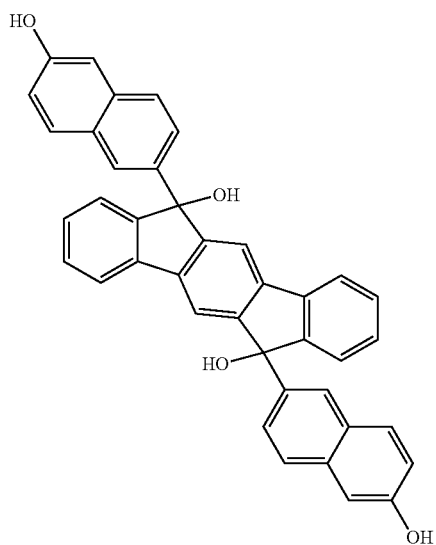
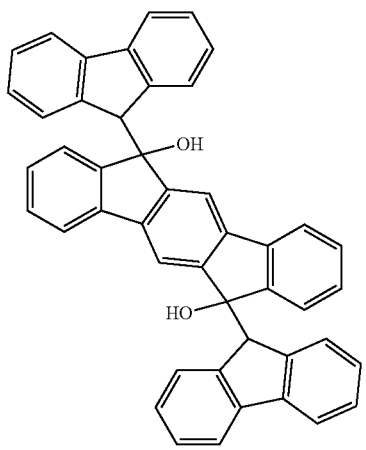
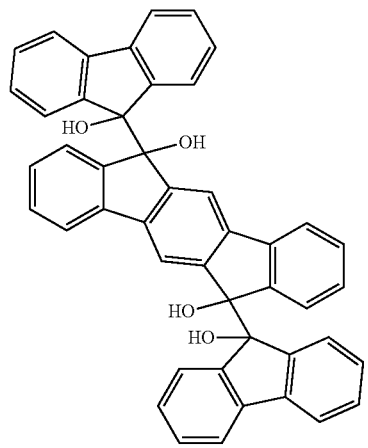

-continued
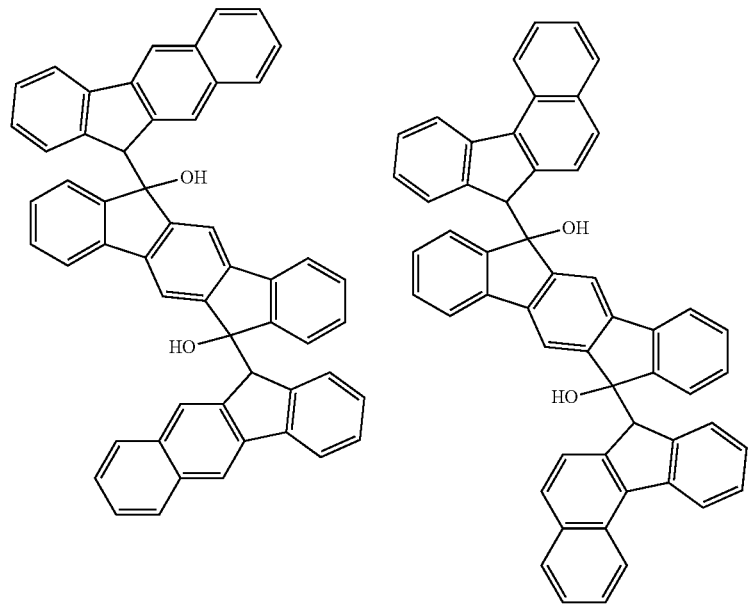
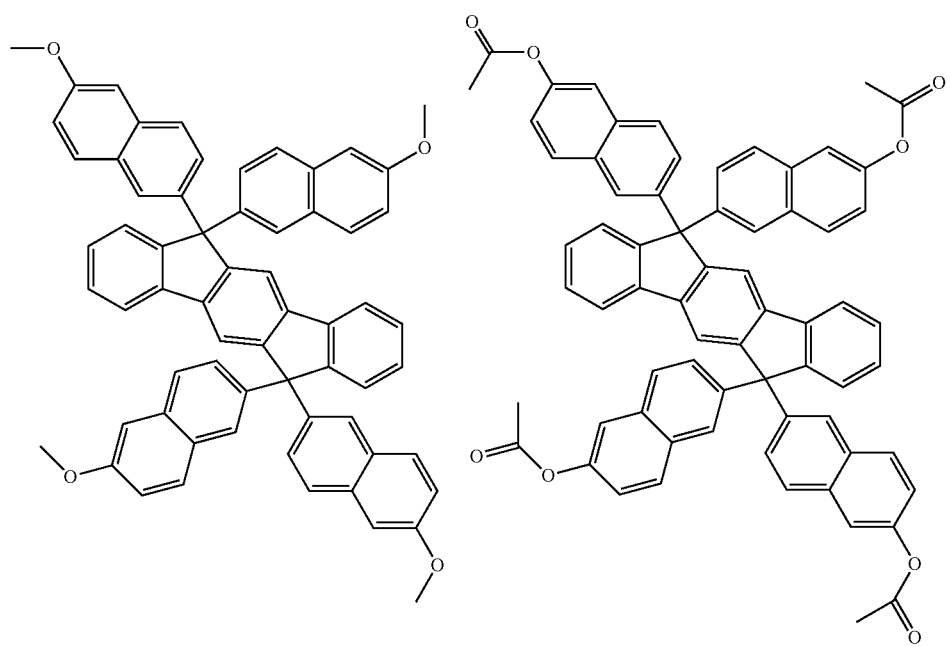

-continued
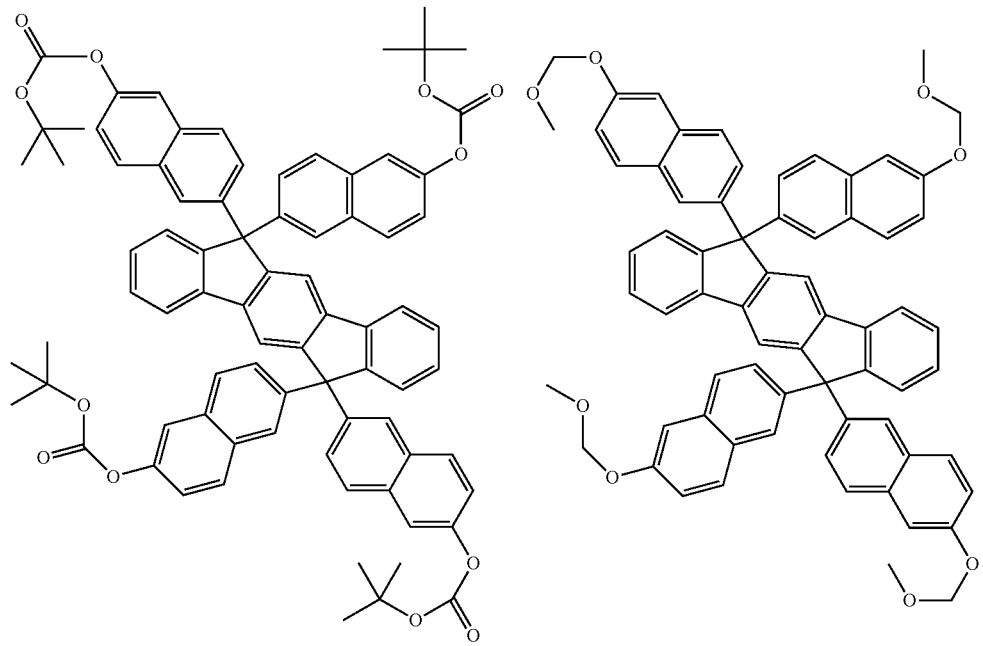
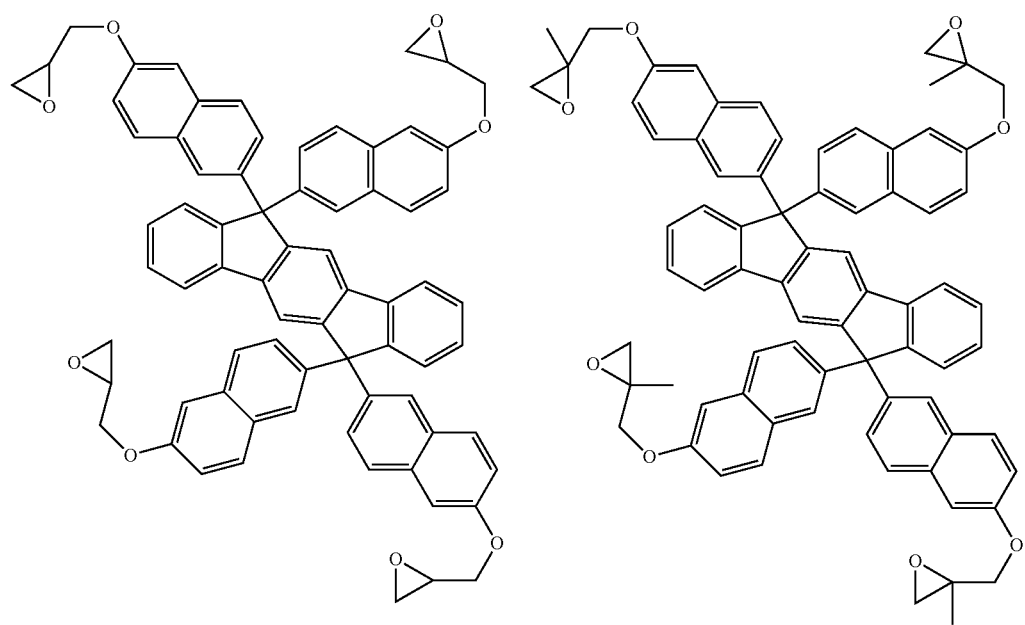

-continued
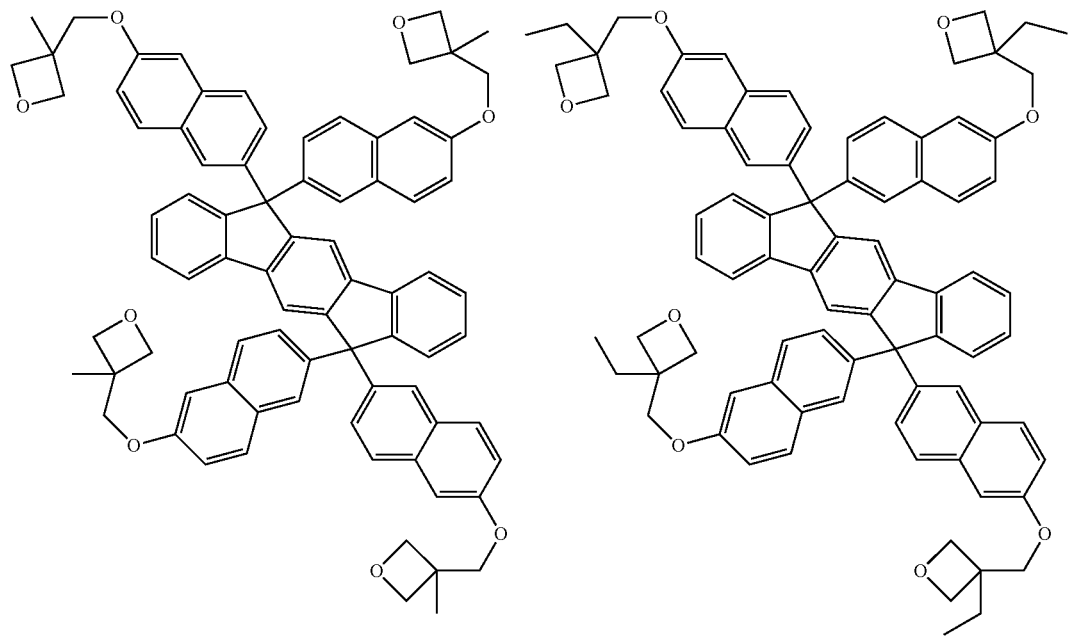
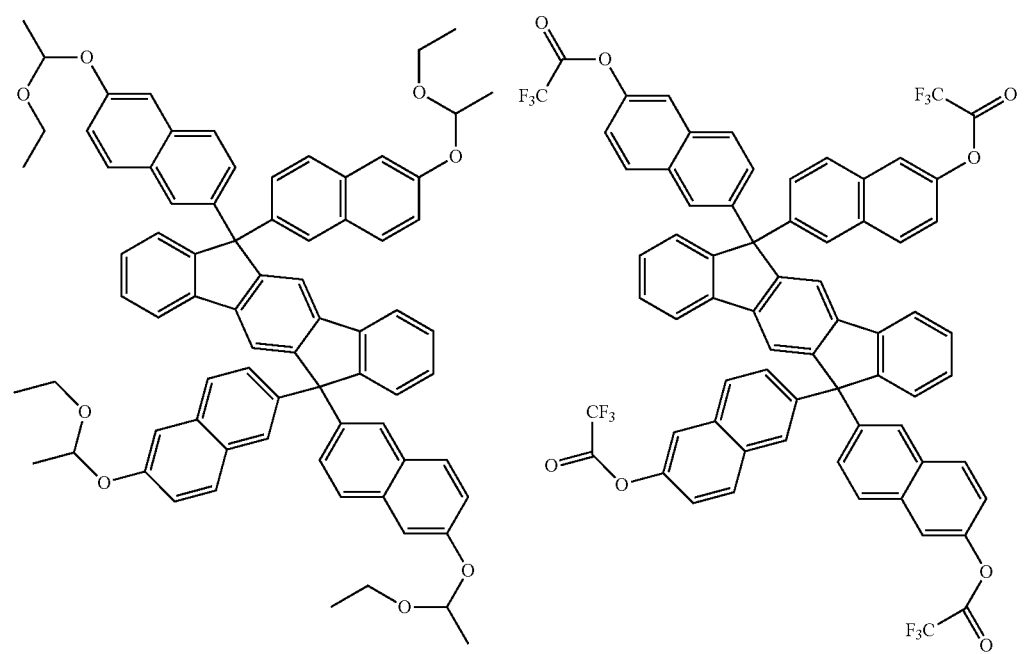

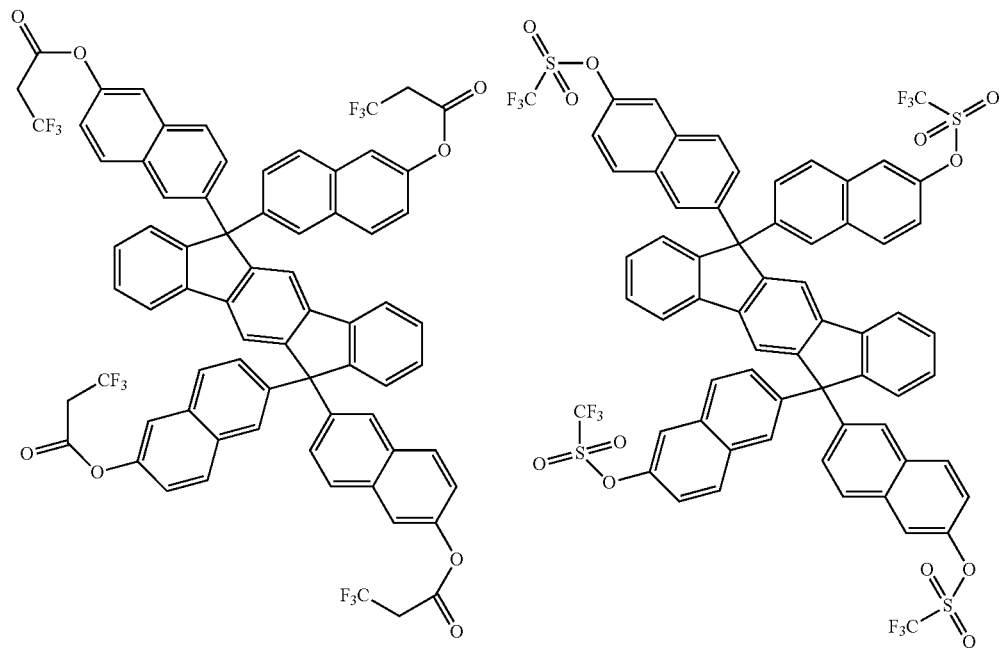
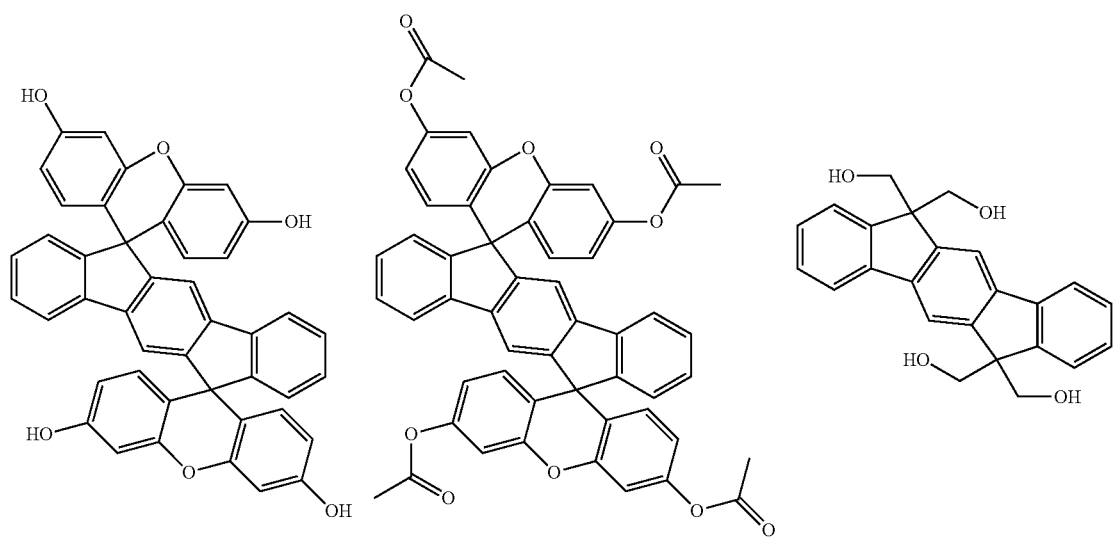
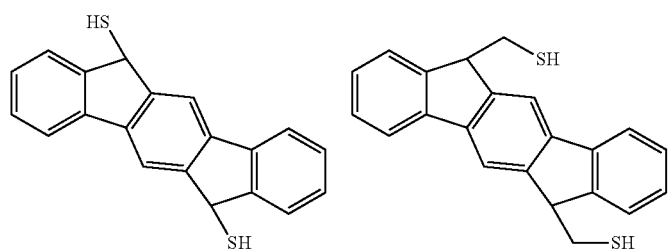

-continued
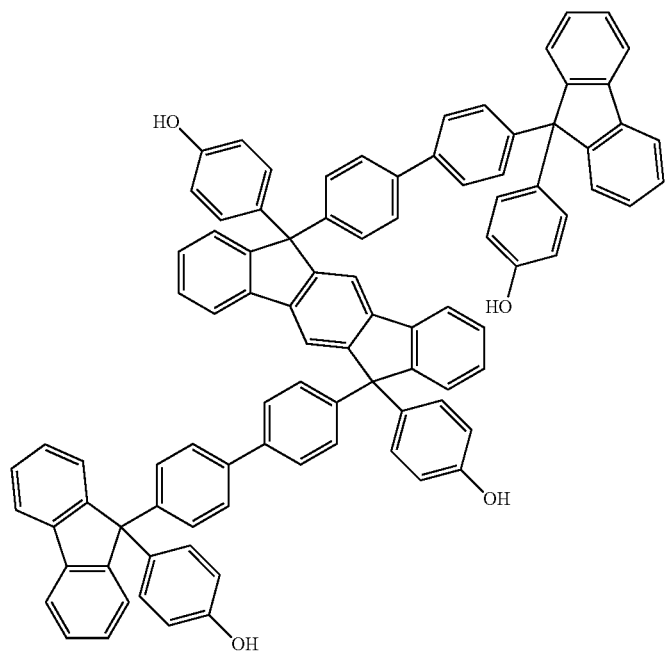
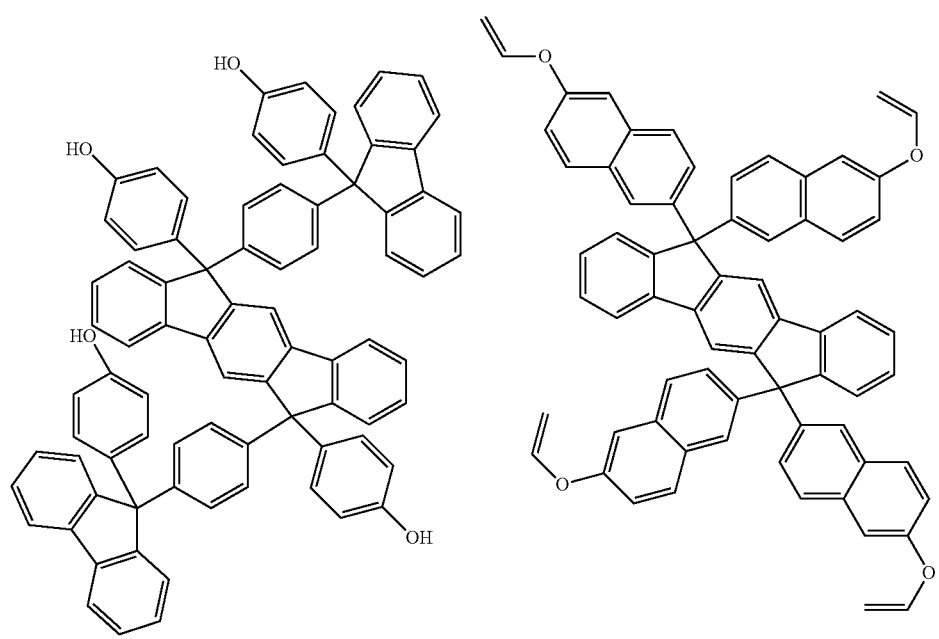

-continued
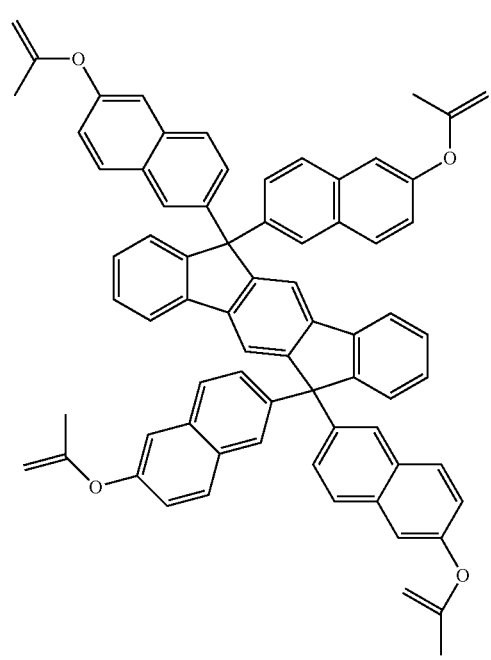
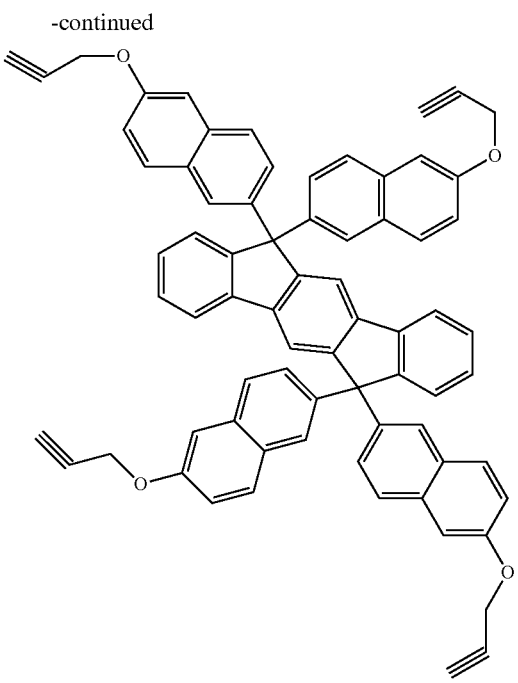
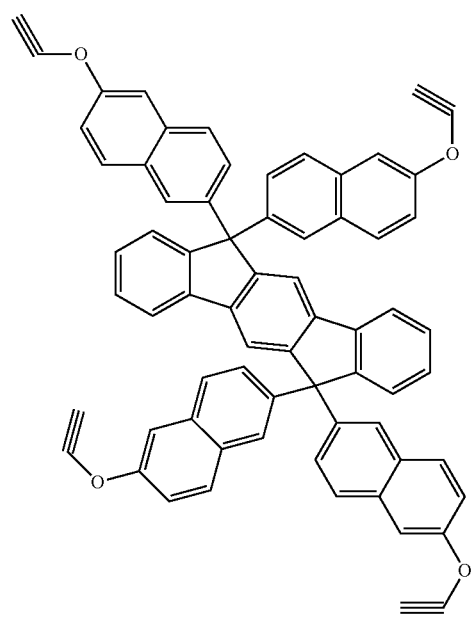
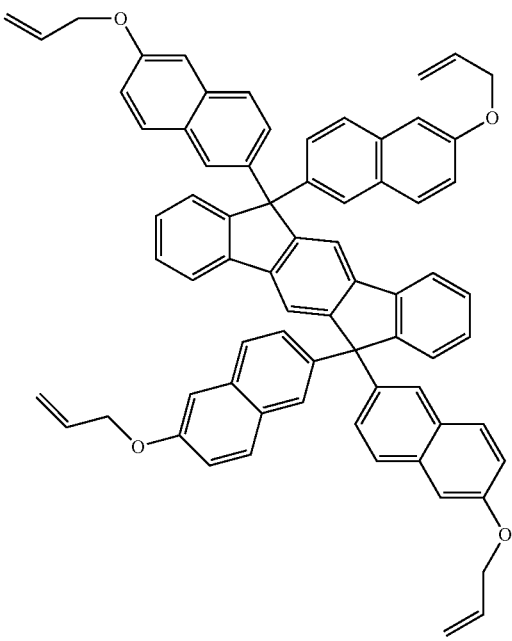
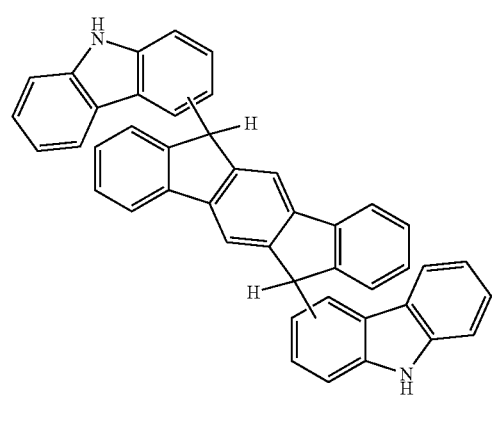
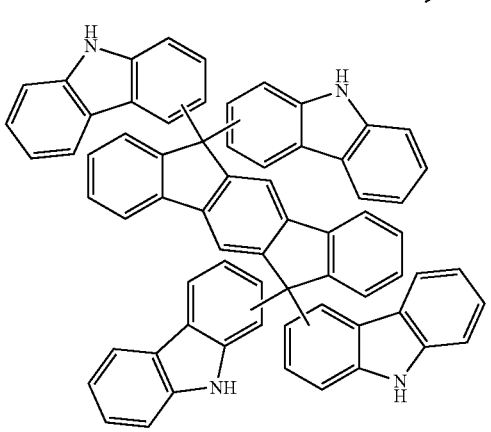

-continued
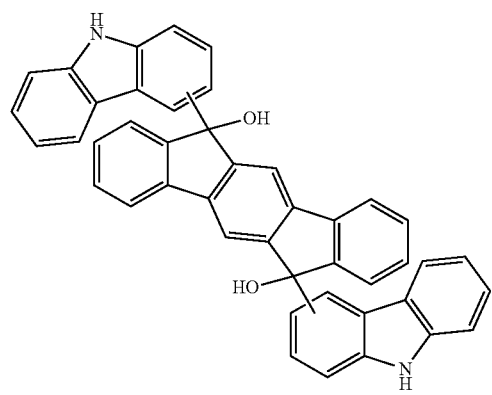
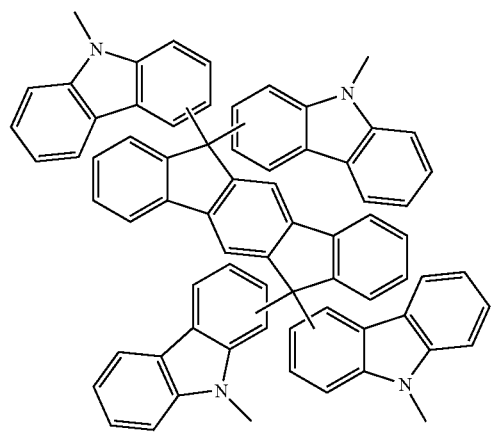
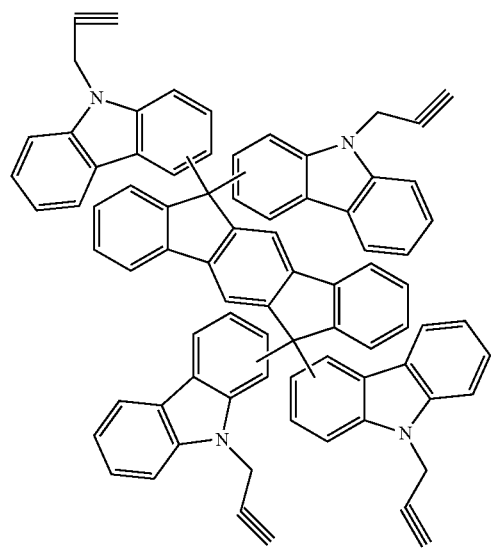
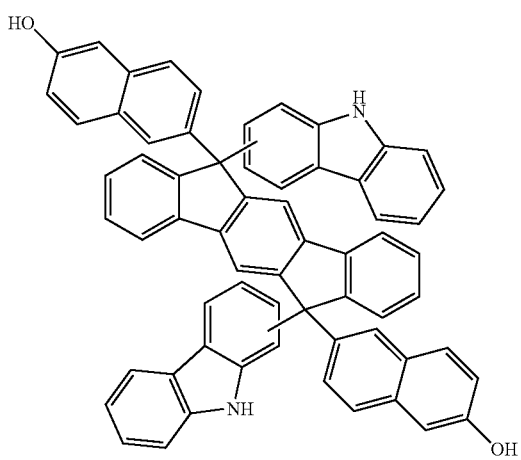
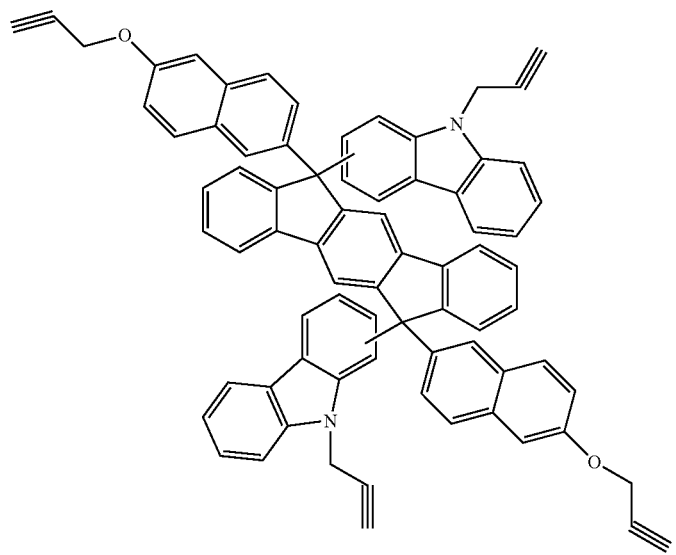
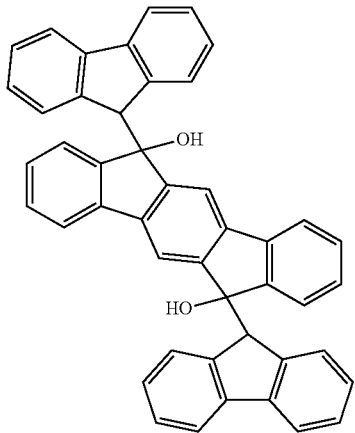

-continued
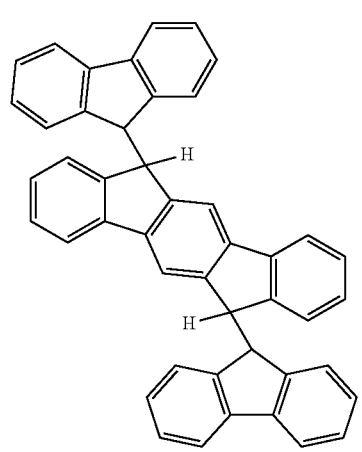
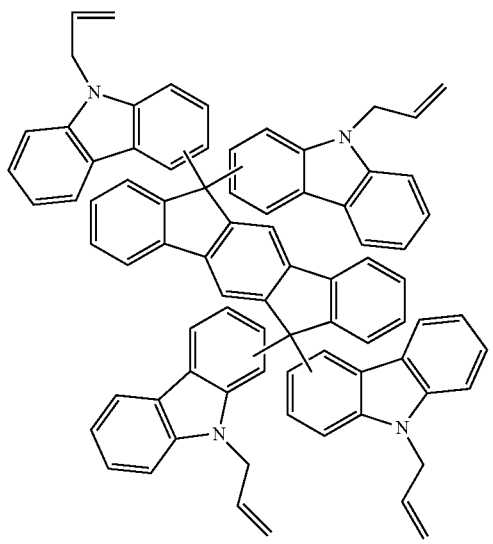
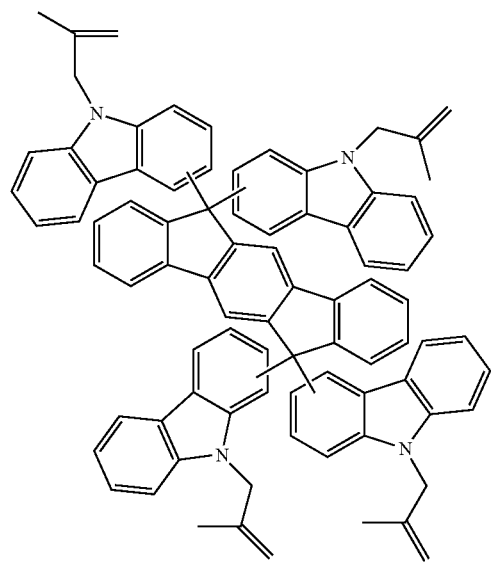
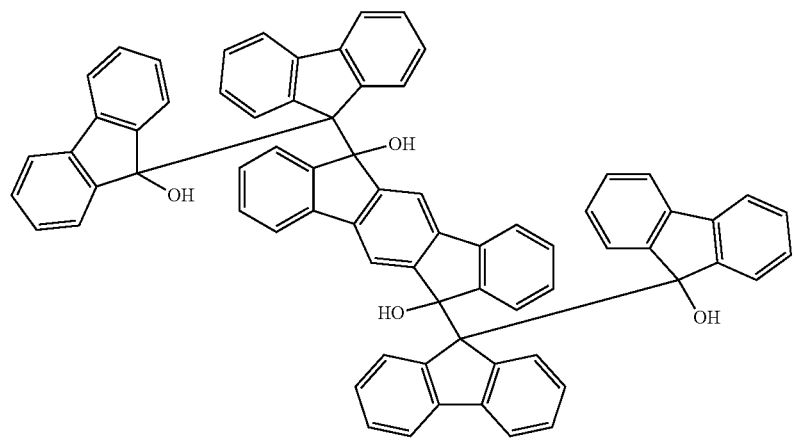

-continued

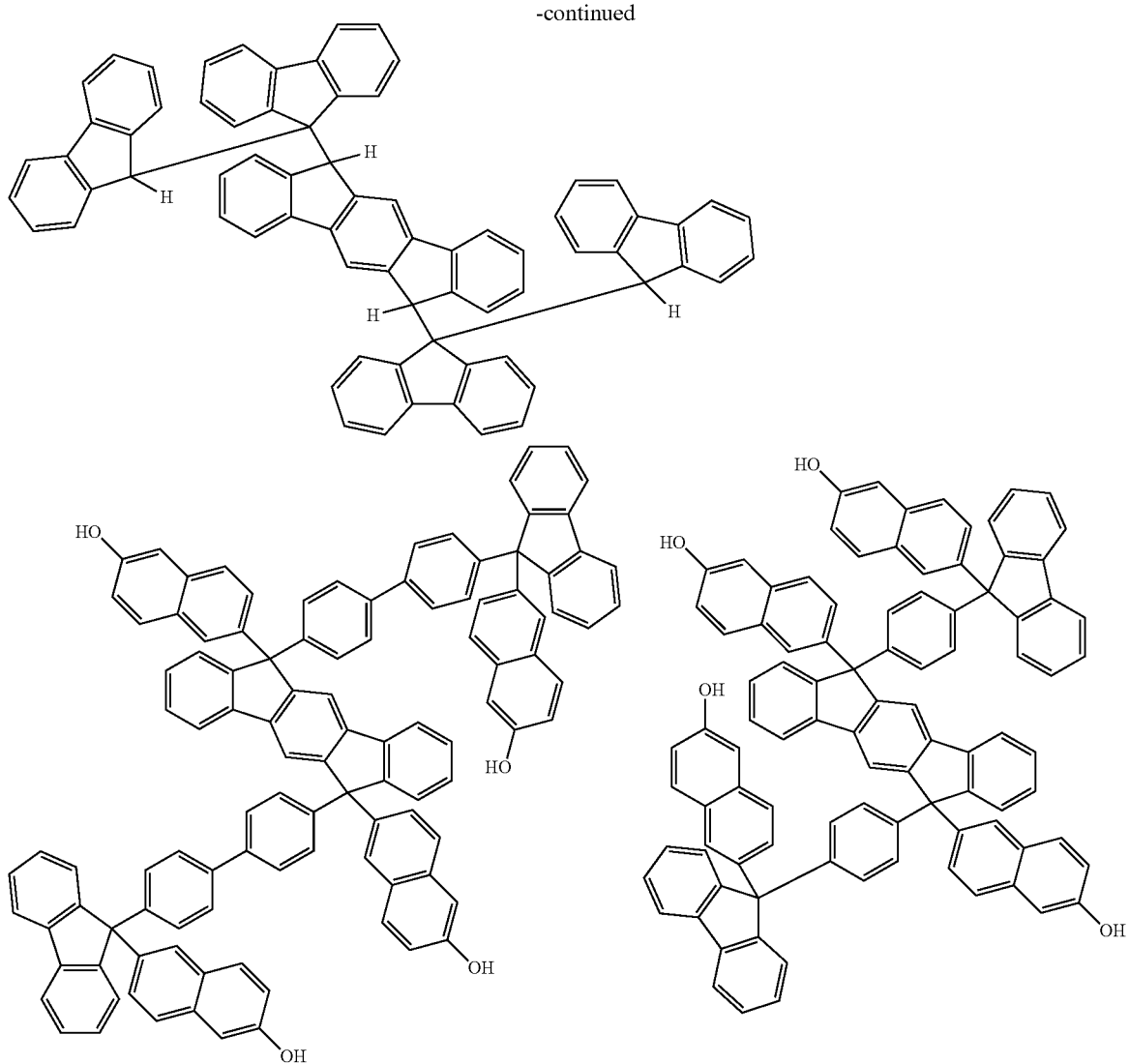

As the compound X, a compound having a substituted or unsubstituted benzene ring or naphthalene ring, as shown by the formula (2), is particularly preferable.

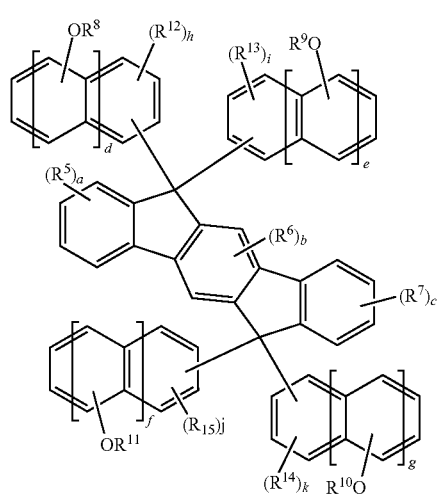

wherein $R^5$, $R^6$, $R^7$, "a", "b" and "c" are as defined above; $R^8$, $R^9$, $R^{10}$, and $R^{11}$ each represent a hydrogen atom, a linear, branched, or cyclic alkyl group having 1 to 16 carbon atoms, a linear, branched, or cyclic alkenyl or alkynyl group having 2 to 10 carbon atoms, an aryl group having 6 to 12 carbon atoms, a linear, branched, or cyclic acyl group having 1 to 16 carbon atoms, an acid-labile group, a group having an oxirane structure, a group having an oxetane structure, or a sulfo group; $R^{12}$, $R^{13}$, $R^{14}$, and $R^{15}$ each represent a hydroxyl group, an acyloxy group, or a linear, branched, or cyclic alkyl group having 1 to 16 carbon atoms; $R^{12}$ and $R^{14}$ may bond to $R^{13}$ and $R^{15}$ respectively via an oxygen atom to form a cyclic ether structure; "d", "e", "f", and "g" each represent 0 or 1; and "h", "i", "j", and "k" each represent an integer of 0 to 5.

Such a compound enables the improvement in filling property, the reduction in outgas, and the improvement in heat resistance to be achieved with particularly good balance.

When $R^8$ to $R^{11}$ are acid-labile groups, these groups may be the same or different. Examples thereof include groups shown by the formulae (A-1) to (A-3).

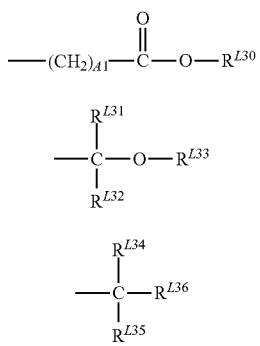
(A-1)

(A-2)

(A-3)

In the formula (A-1) $R^{L30}$ represents a tertiary alkyl group having 4 to 20, preferably 4 to 15 carbon atoms, a trialkylsilyl group containing alkyl groups having 1 to 6 carbon atoms, an oxoalkyl group having 4 to 20 carbon atoms, or a group shown by the formula (A-3). Illustrative examples of the tertiary alkyl group include a tert-butyl group, a tert-amyl group, a 1,1-diethylpropyl group, a 1-ethylcyclopentyl group, a 1-butylcyclopentyl group, a 1-ethylcyclohexyl group, a 1-butylcyclohexyl group, a 1-ethyl-2-cyclopentenyl group, a 1-ethyl-2-cyclohexenyl group, and a 2-methyl-2-adamantyl group; illustrative examples of the trialkylsilyl group include a trimethylsilyl group, a triethylsilyl group, and a dimethyl-tert-butylsilyl group; and illustrative examples of the oxoalkyl group include a 3-oxocyclohexyl group, a 4-methyl-2-oxooxane-4-yl group, and a 5-methyl-2-oxooxolane-5-yl group. A1 is an integer of 0 to 6.

Illustrative examples of the acid-labile group of the formula (A-1) include a tert-butoxycarbonyl group, a tert-butoxycarbonylmethyl group, a tert-amyloxycarbonyl group, a tert-amyloxycarbonylmethyl group, a 1,1-diethylpropyloxycarbonyl group, a 1,1-diethylpropyloxycarbonylmethyl group, a 1-ethylcyclopentyloxycarbonyl group, a 1-ethylcyclopentyloxycarbonylmethyl group, a 1-ethyl-2-cyclopentenyloxycarbonyl group, a 1-ethyl-2-cyclopentenyloxycarbonylmethyl group, a 1-ethoxyethoxycarbonylmethyl group, a 2-tetrahydropyranyloxycarbonylmethyl group, and a 2-tetrahydrofuranyloxycarbonylmethyl group.

Other examples thereof include groups shown by the formulae (A-1)-1 to (A-1)-10.

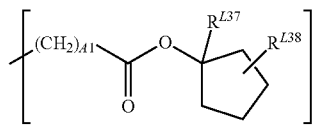
(A-1)-1

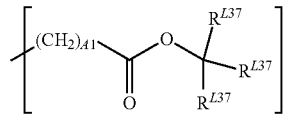
(A-1)-2

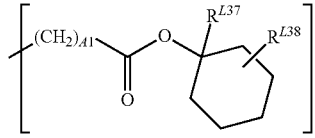
(A-1)-3

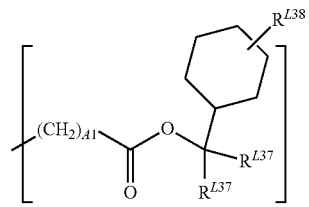
(A-1)-4

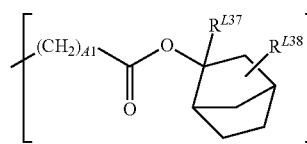
(A-1)-5

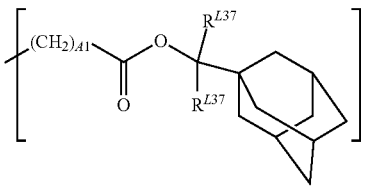
(A-1)-6

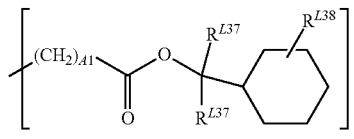
(A-1)-7

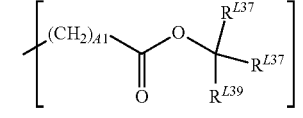
(A-1)-8

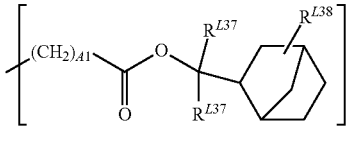
(A-1)-9

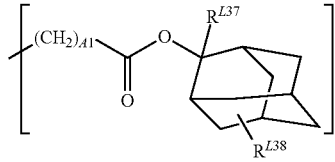
(A-1)-10

In these formulae, each $R^{L37}$ may be the same or different, and represents a linear, branched, or cyclic alkyl group having 1 to 10 carbon atoms or an aryl group having 6 to 17 carbon atoms; $R^{L38}$ represents a hydrogen atom or a linear, branched, or cyclic alkyl group having 1 to 10 carbon atoms; each $R^{L39}$ may be the same or different, and represents a linear, branched, or cyclic alkyl group having 2 to 10 carbon atoms or an aryl group having 6 to 20 carbon atoms; and A1 is as defined above.

In the formula (A-2), $R^{L31}$ and $R^{L32}$ represent a hydrogen atom or a linear, branched, or cyclic alkyl group having 1 to 18, preferably 1 to 10 carbon atoms. Illustrative examples of the alkyl group include a methyl group, an ethyl group, a propyl group, an isopropyl group, a n-butyl group, a sec-butyl group, a tert-butyl group, a cyclopentyl group, a cyclohexyl group, a 2-ethylhexyl group, and a n-octyl group. $R^{L33}$ represents a monovalent hydrocarbon group having 1 to 18, preferably 1 to 10 carbon atoms, and optionally containing a heteroatom such as an oxygen atom. More specifically, there may be mentioned a linear, branched, or cyclic alkyl group and a group in which a part of hydrogen atoms in these groups is substituted with a hydroxyl group, an alkoxy group, an oxo group, an amino group, an alkylamino group, or the like. Illustrative examples thereof include the following substituted alkyl groups.

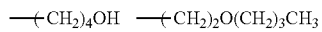
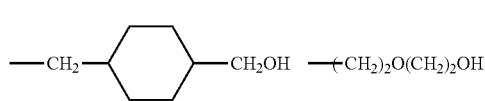
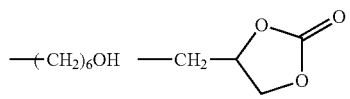

$R^{L31}$ and $R^{L32}$, $R^{L31}$ and $R^{L33}$, and $R^{L32}$ and $R^{L33}$ may be bonded to form a ring together with the carbon atoms to which these groups are bonded; and when the ring is formed, each of $R^{L31}$, $R^{L32}$, and $R^{L33}$ that participate in the ring formation represents a linear or branched alkylene group having 1 to 18, preferably 1 to 10 carbon atoms. The carbon number in the ring is preferably 3 to 10, particularly preferably 4 to 10.

Among the acid-labile groups shown by the formula (A-2), illustrative examples of the linear or branched one include groups shown by the formulae (A-2)-1 to (A-2)-69.

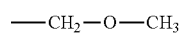 (A-2)-1

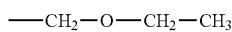 (A-2)-2

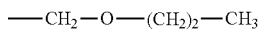 (A-2)-3

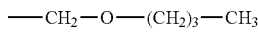 (A-2)-4

 (A-2)-5

 (A-2)-6

 (A-2)-7

 (A-2)-8

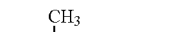 (A-2)-9

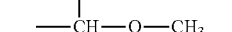 (A-2)-10

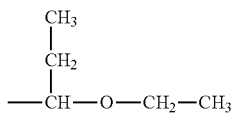 (A-2)-11

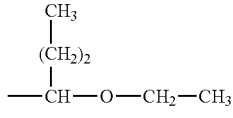 (A-2)-12

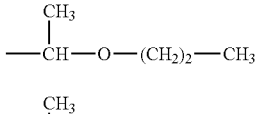 (A-2)-13

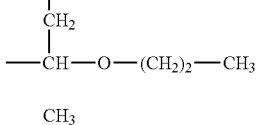 (A-2)-14

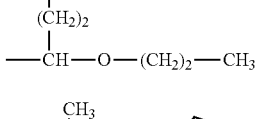 (A-2)-15

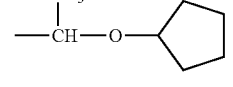 (A-2)-16

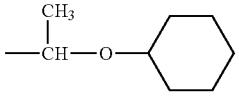 (A-2)-17

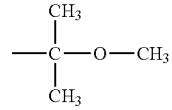 (A-2)-18

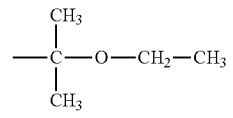 (A-2)-19

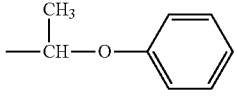 (A-2)-20

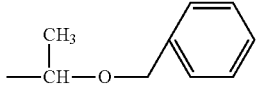 (A-2)-21

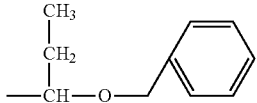 (A-2)-22

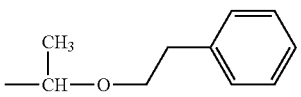 (A-2)-23

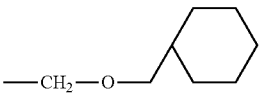 (A-2)-24

-continued (A-2)-25: —CH₂—O—CH₂CH₂—cyclohexyl (A-2)-26: —CH₂—O—CH₂—adamantyl (A-2)-27: —CH₂—O—CH₂CH₂—adamantyl (A-2)-28: —CH₂—O—bicyclic (A-2)-29: —CH₂—O—dimethylbicyclic (A-2)-30: —CH₂—O—(4-methyl-2-isopropylcyclohexyl)

(A-2)-31: —CH₂—O—adamantyl (A-2)-32: —CH₂—O—adamantyl derivative (A-2)-33: —CH₂—O—CH₂—adamantyl (A-2)-34: —CH₂—O—CH₂—adamantyl derivative (A-2)-35: —CH₂—O—(cyclohexyl-cyclohexyl)

(A-2)-36: (CH₃)₂CH—CH(O—CH₃)—

(A-2)-37: (CH₃)₂CH—CH(O—CH₂CH₃)—

(A-2)-38: (CH₃)₂CH—CH₂—CH(O—CH₃)—

(A-2)-39: (CH₃)₂CH—CH(CH₃)—CH(O—CH₃)—

(A-2)-40: cyclohexyl—CH(O—CH₃)—

(A-2)-41: cyclopentyl—CH(O—CH₃)—

(A-2)-42: (CH₃)₂CH—CH(O—CH(CH₃)₂)—

(A-2)-43: (CH₃)₂CH—CH(O—C(CH₃)₃)—

(A-2)-44: cycloheptyl—CH(O—CH₃)—

(A-2)-45: cyclooctyl—CH(O—CH₃)—

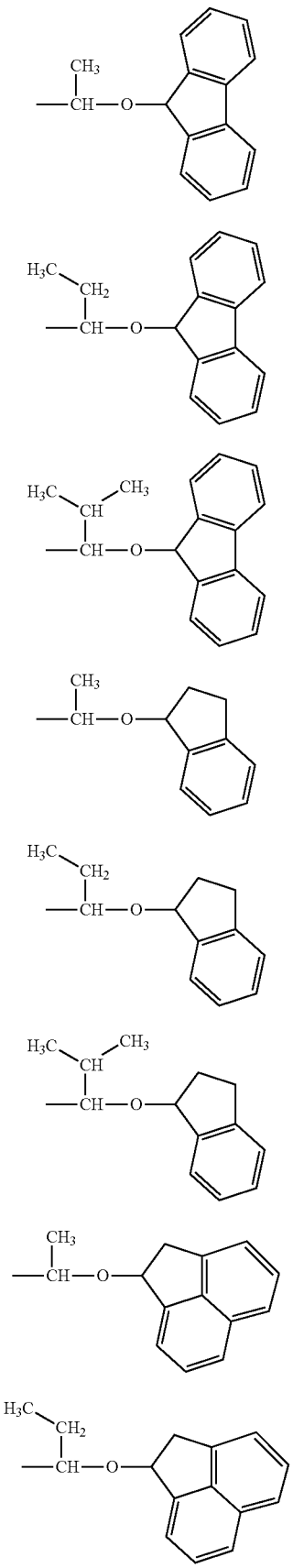
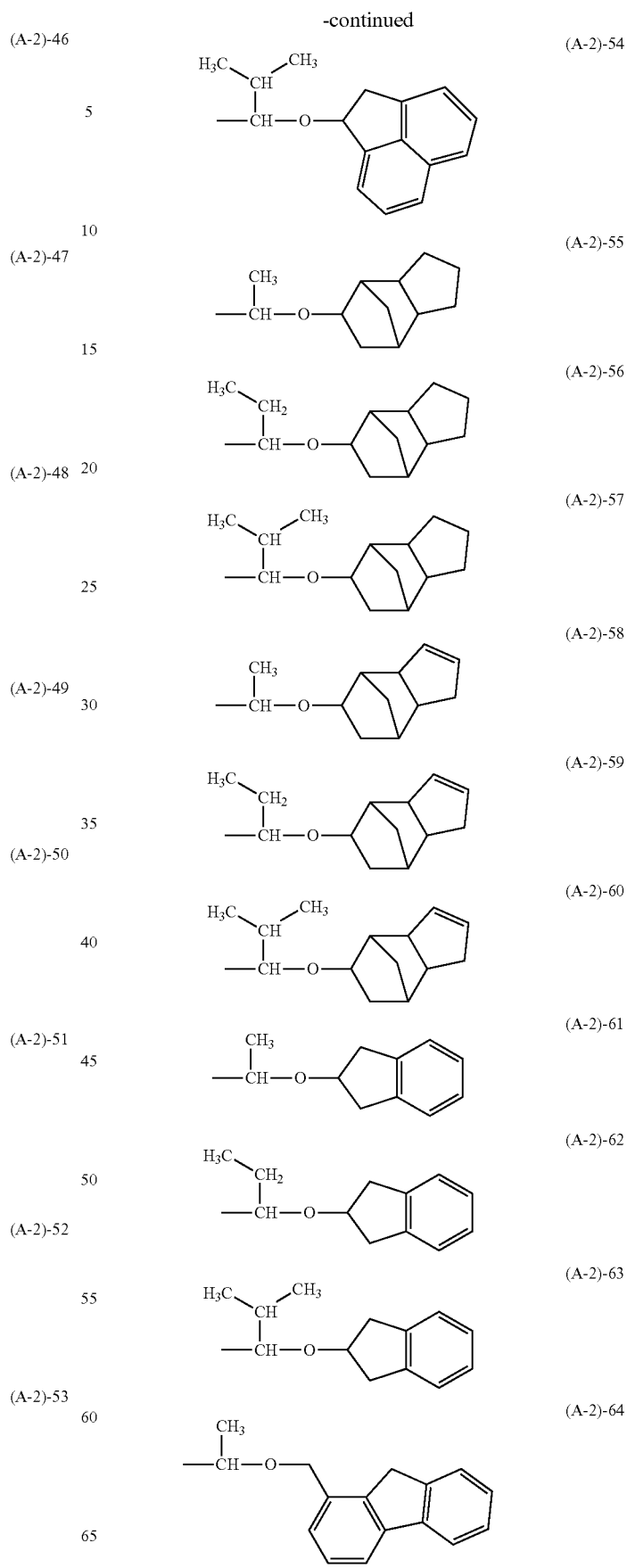

(A-2)-65
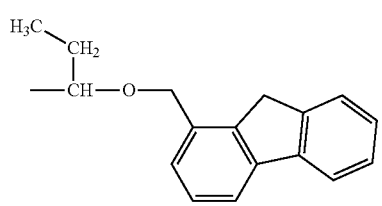

(A-2)-66
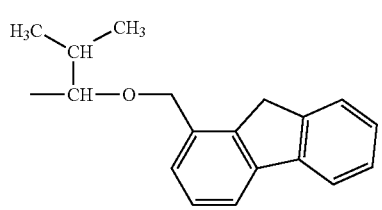

(A-2)-67
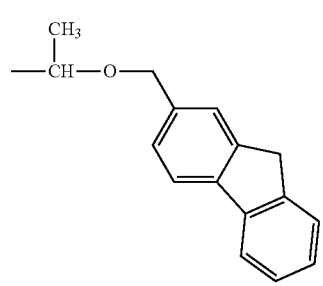

(A-2)-68
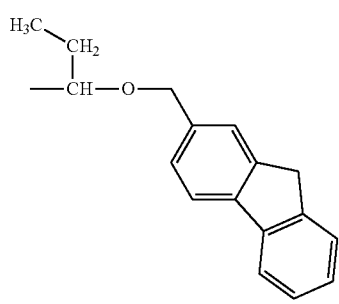

(A-2)-69
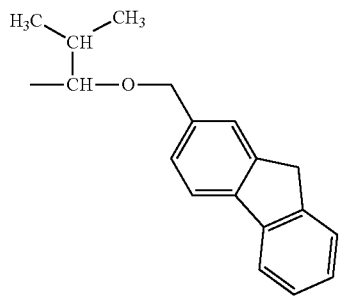

Among the acid-labile groups shown by the formula (A-2), illustrative examples of the cyclic one include a tetrahydrofuran-2-yl group, a 2-methyltetrahydrofuran-2-yl group, a tetrahydropyran-2-yl group, and a 2-methyltetrahydropyran-2-yl group.

The indeno[1,2-b]fluorene compound(s) may be linked through an acid-labile group shown by the formula (A-2a) or (A-2b) to form intermolecular or intramolecular crosslinking.

(A-2a)
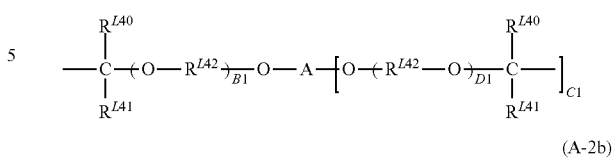

(A-2b)
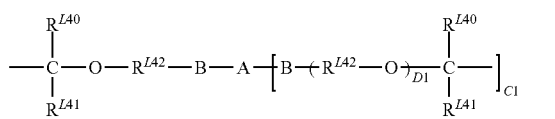

In the formulae (A-2a) and (A-2b), $R^{L40}$ and $R^{L41}$ represent a hydrogen atom or a linear, branched, or cyclic alkyl group having 1 to 8 carbon atoms. Alternatively, $R^{L40}$ and $R^{L41}$ may be bonded to form a ring together with the carbon atoms to which these groups are bonded. When the ring is formed, $R^{L40}$ and $R^{L41}$ represent a linear or branched alkylene group having 1 to 8 carbon atoms. $R^{L42}$ represents a linear, branched, or cyclic alkylene group having 1 to 10 carbon atoms. B1 and D1 represent an integer of 0 to 10, preferably 0 to 5. C1 represents an integer of 1 to 7, preferably 1 to 3.

In the formulae (A-2a) and (A-2b), "A" represents an aliphatic or alicyclic saturated hydrocarbon group, an aromatic hydrocarbon group, or a heterocyclic group having 1 to 50 carbon atoms with a valency of (C1+1); these groups may contain a heteroatom, or a part of hydrogen atoms bonded to the carbon atom in these groups may be substituted with a hydroxyl group, a carboxyl group, a carbonyl group, or a fluorine atom. "A" is preferably a linear, branched, or cyclic alkylene group, alkyltriyl group, alkyltetrayl group having 2 to 4 valency and 1 to 20 carbon atoms, or an arylene group having 6 to 30 carbon atoms; these group may contain a heteroatom, or a part of hydrogen atoms bonded to the carbon atom in these groups may be substituted with a hydroxyl group, a carboxyl group, an acyl group, or a halogen atom.

In the formula (A-2b), "B" represents —CO—O—, —NHCO—O—, or —NHCONH—.

Illustrative examples of the crosslinking acetal group shown by the formula (A-2a) or (A-2b) include groups shown by the formulae (A-2)-70 to (A-2)-77.

(A-2)-70
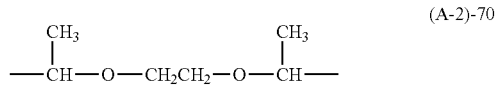

(A-2)-71
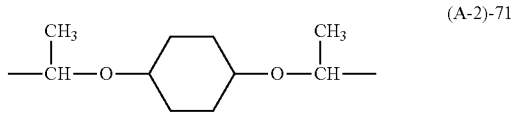

(A-2)-72
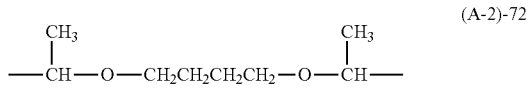

(A-2)-73

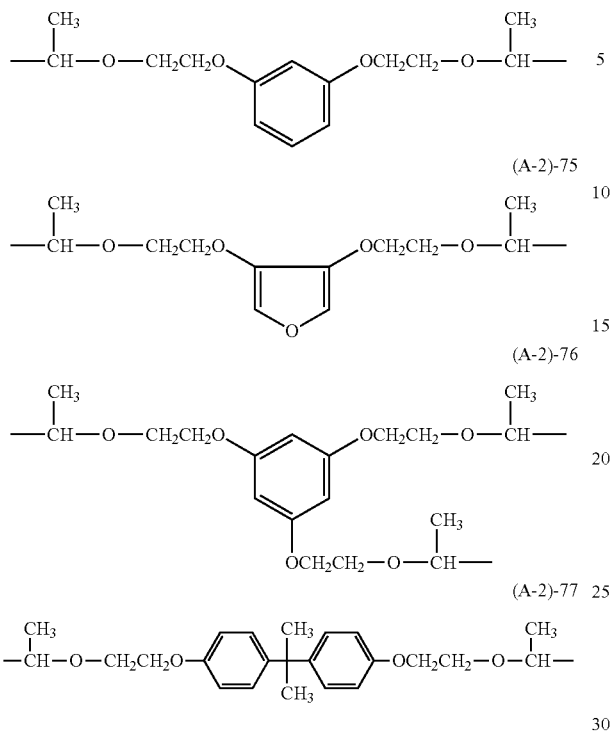

(A-2)-74

(A-2)-75

(A-2)-76

(A-2)-77

In the formula (A-3), $R^{L34}$, $R^{L35}$, and $R^{L36}$ represent a monovalent hydrocarbon group such as a linear, branched, or cyclic alkyl group having 1 to 20 carbon atoms or a linear, branched, or cyclic alkenyl group having 2 to 20 carbon atoms. These groups may contain a heteroatom such as oxygen, sulfur, nitrogen, and fluorine. $R^{L34}$ and $R^{L35}$, $R^{L34}$ and $R^{L36}$, and $R^{L35}$ and $R^{L36}$ may be bonded to form an aliphatic ring structure having 3 to 20 carbon atoms together with the carbon atoms to which these groups are bonded.

Illustrative examples of the tertiary alkyl group shown by the formula (A-3) include a tert-butyl group, a triethylcarbyl group, a 1-ethylnorbornyl group, a 1-methylcyclohexyl group, a 1-ethylcyclopentyl group, a 2-(2-methyl)adamantyl group, a 2-(2-ethyl)adamantyl group, and a tert-amyl group.

Other examples of the tertiary alkyl group include groups shown by the formulae (A-3)-1 to (A-3)-18.

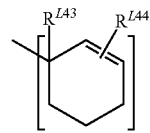

(A-3)-1

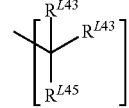

(A-3)-2

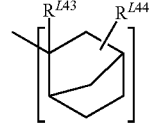

(A-3)-3

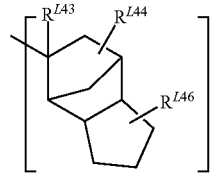

(A-3)-4

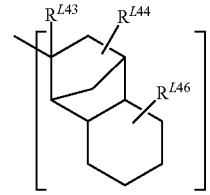

(A-3)-5

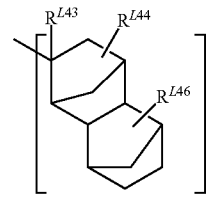

(A-3)-6

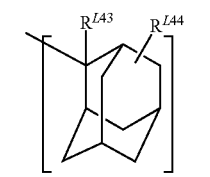

(A-3)-7

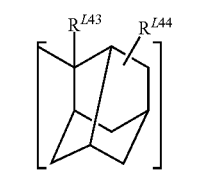

(A-3)-8

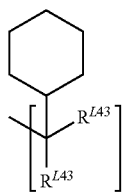

(A-3)-9

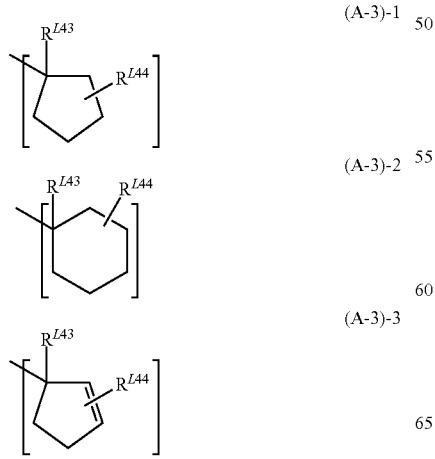

(A-3)-10

(A-3)-11

(A-3)-12

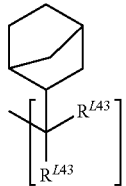
(A-3)-13

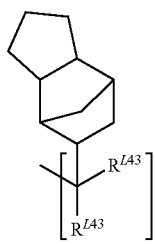
(A-3)-14

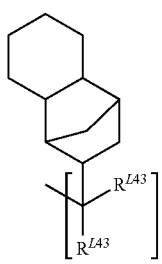
(A-3)-15

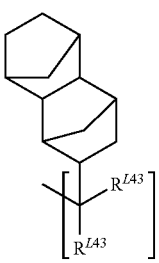
(A-3)-16

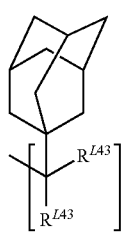
(A-3)-17

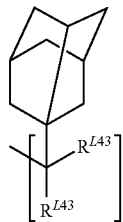
(A-3)-18

In these formulae (A-3)-1 to (A-3)-18, each $R^{L43}$ may be the same or different, and represents a linear, branched, or cyclic alkyl group having 1 to 8 carbon atoms, or an aryl group having 6 to 20 carbon atoms, such as a phenyl group. $R^{L44}$ and $R^{L46}$ represent a hydrogen atom or a linear, branched, or cyclic alkyl group having 1 to 20 carbon atoms. $R^{L45}$ represents an aryl group having 6 to 20 carbon atoms, such as a phenyl group.

Furthermore, as shown in the following formulae (A-3)-19 and (A-3)-20, the indeno[1,2-b]fluorene compound may contain $R^{L47}$ to form intermolecular or intramolecular cross-linking.

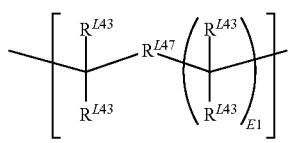
(A-3)-19

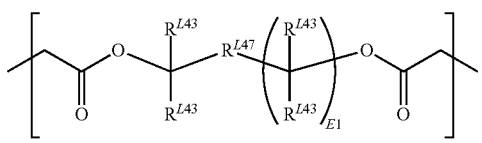
(A-3)-20

In the formulae (A-3)-19 and (A-3)-20, $R^{L43}$ is as defined above; $R^{L47}$ represents a linear, branched, or cyclic alkylene group having 1 to 20 carbon atoms or an arylene group such as a phenylene group, in which these groups may contain a heteroatom such as oxygen, sulfur, and nitrogen; and E1 represents an integer of 1 to 3.

[Compound Y]

The indeno[1,2-b]fluorene compound contained in the inventive resist underlayer film composition may be the compound Y in which multiple compounds X are bonded directly or via an arylene group having 6 to 28 carbon atoms and optionally containing an alkylene group having 1 to 10 carbon atoms. Illustrative examples of the compound Y include the following compounds, although it is not limited thereto.

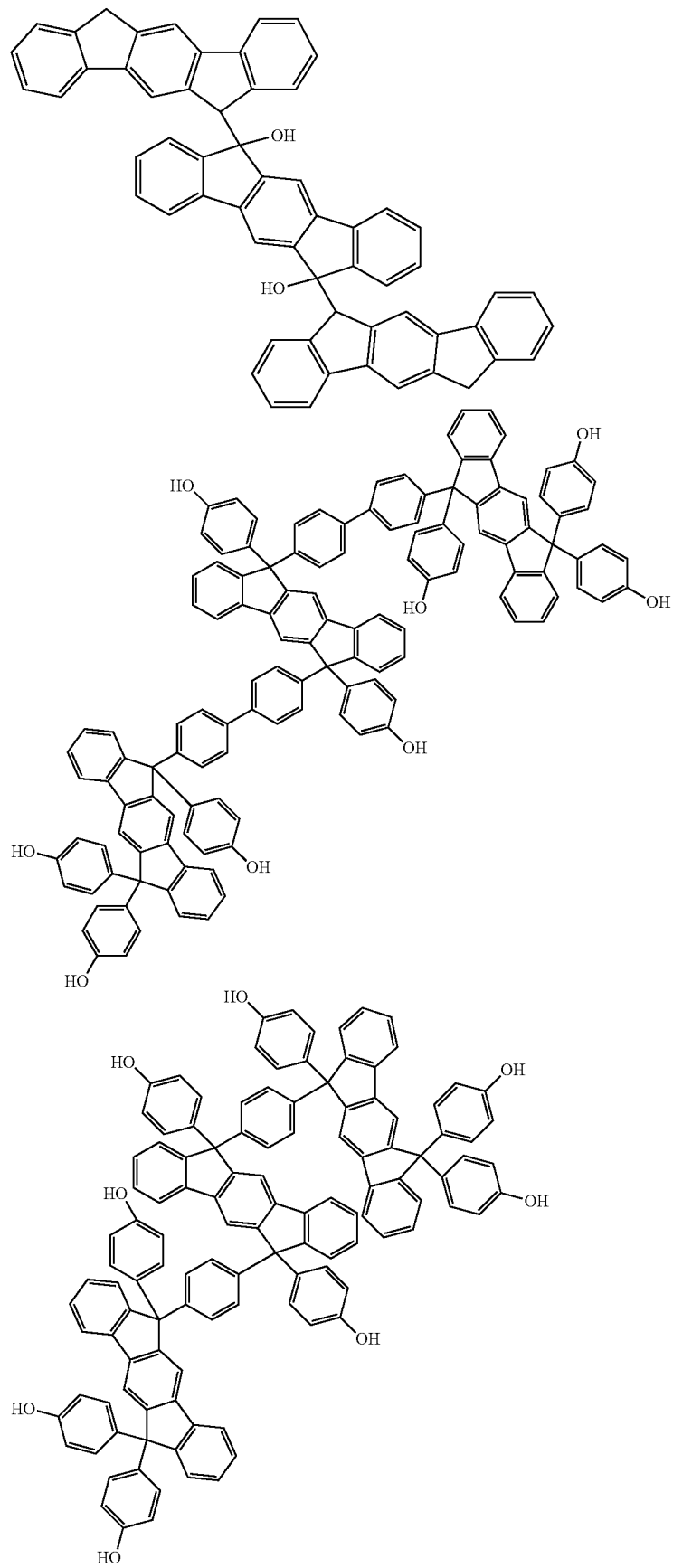

-continued
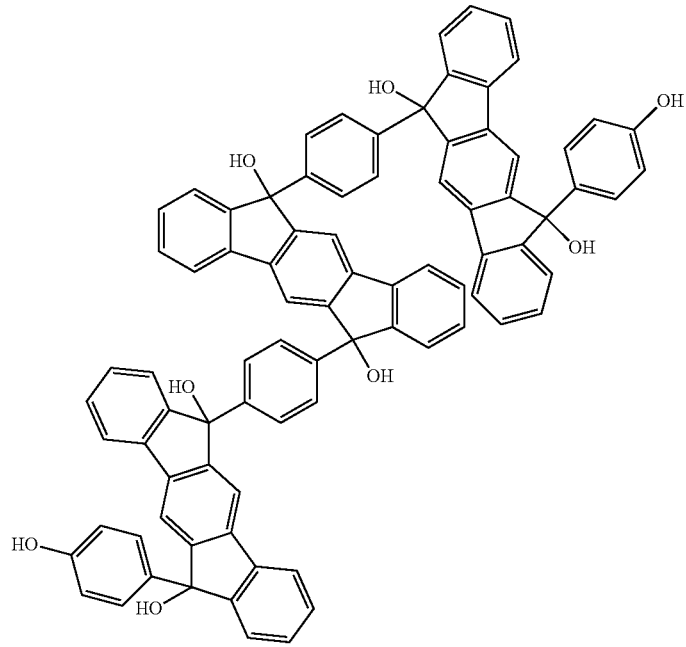
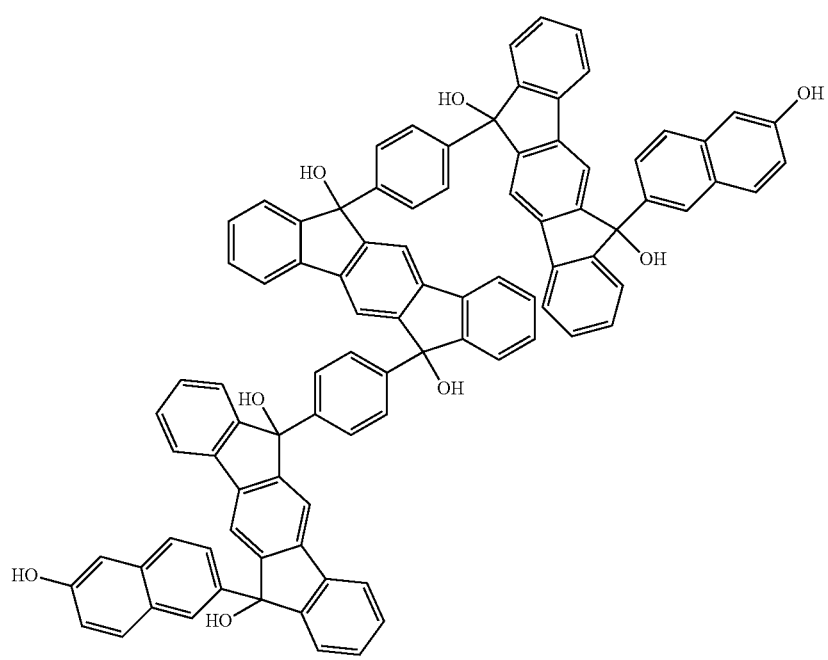

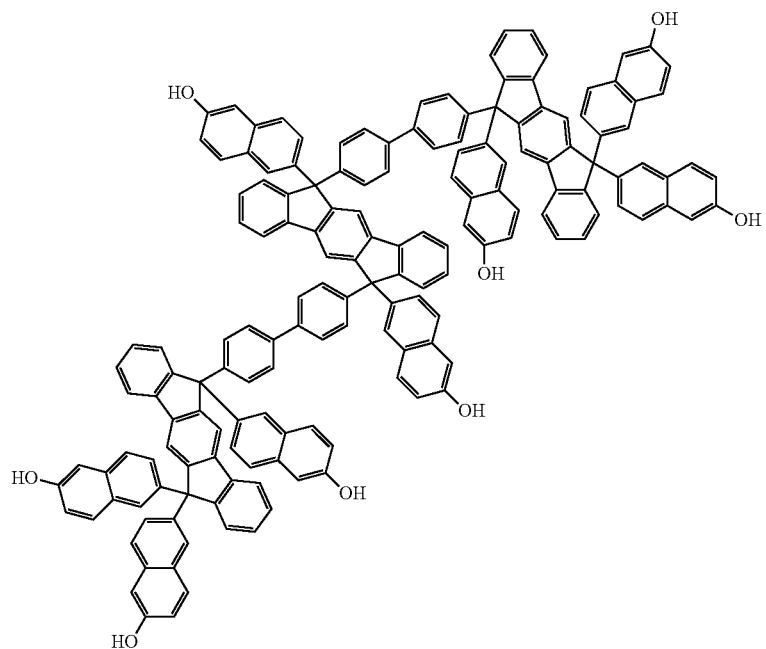
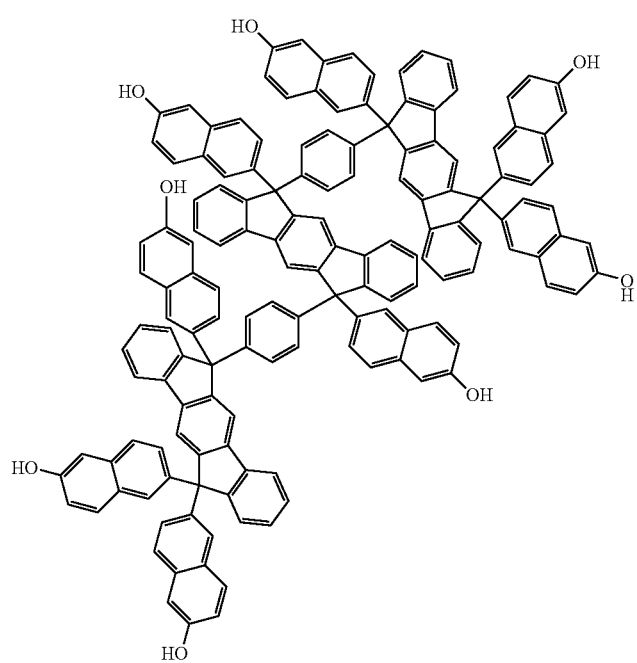

-continued
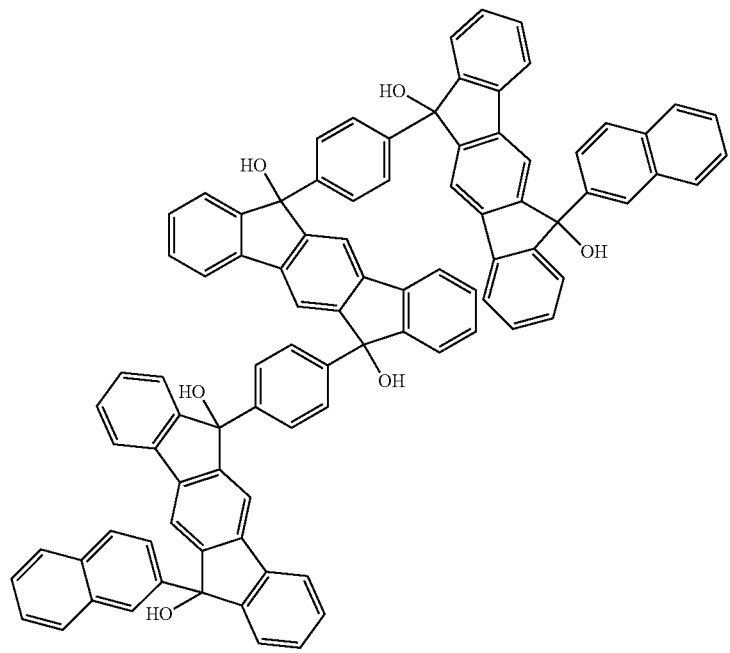
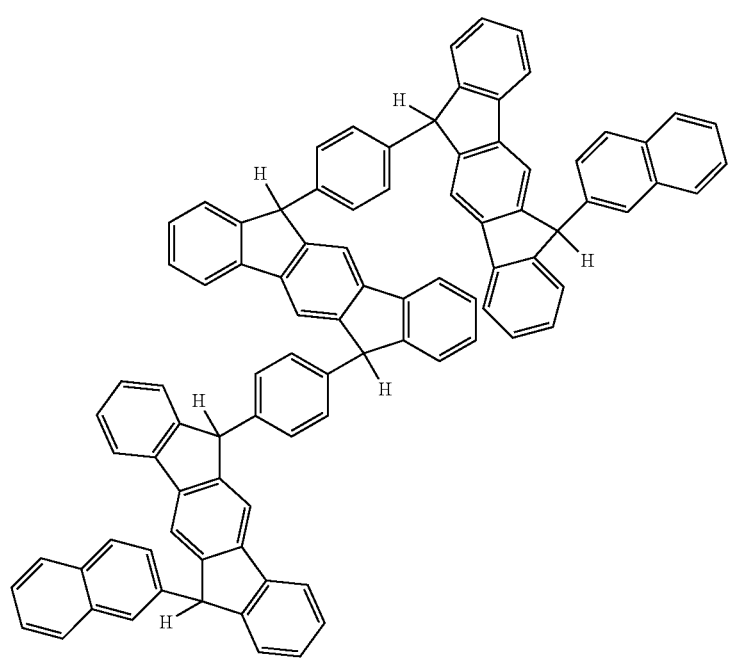

-continued

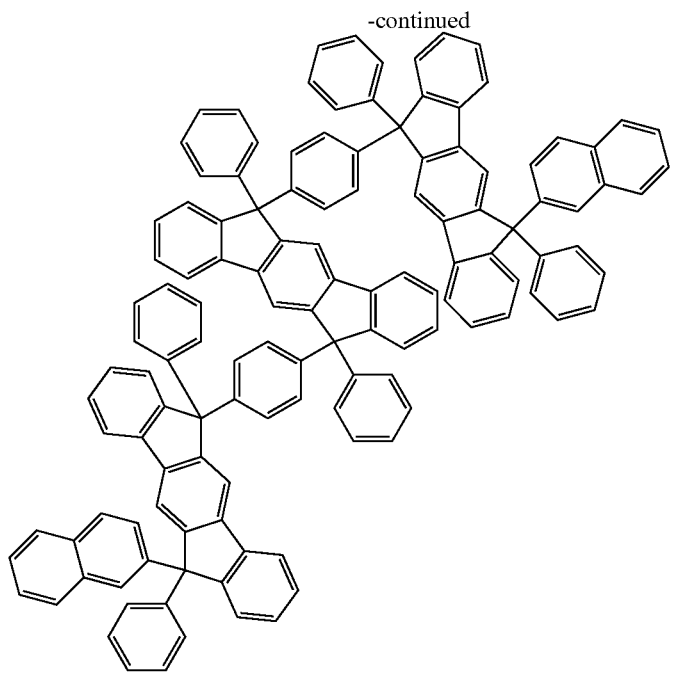

[Condensate]

The indeno[1,2-b]fluorene compound contained in the inventive resist underlayer film composition may be the condensate obtained by a condensation of a material containing the compound X and/or the compound Y. As such a condensate, a resin having a repeating unit shown by the formula (3) is particularly preferable,

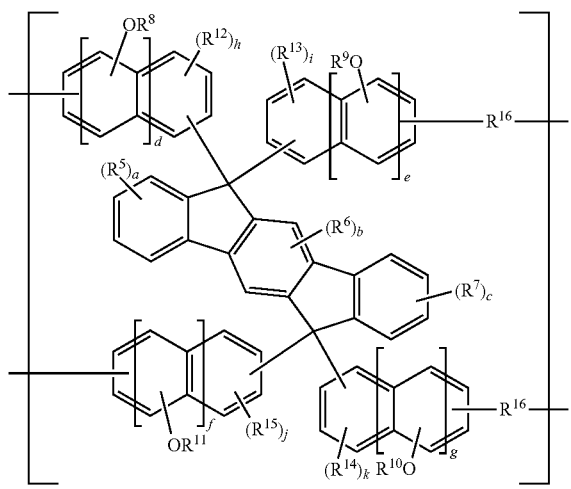

(3)

wherein $R^5$, $R^6$, $R^7$, "a", "b" and "c" are as defined above; $R^8$, $R^9$, $R^{10}$, and $R^{11}$ each represent a hydrogen atom, a linear, branched, or cyclic alkyl group having 1 to 16 carbon atoms, a linear, branched, or cyclic alkenyl or alkynyl group having 2 to 10 carbon atoms, an aryl group having 6 to 12 carbon atoms, a linear, branched, or cyclic acyl group having 1 to 16 carbon atoms, an acid-labile group, a group having an oxirane structure, a group having an oxetane structure, or a sulfo group; $R^{12}$, $R^{13}$, $R^{14}$, and $R^{15}$ each represent a hydroxyl group, an acyloxy group, or a linear, branched, or cyclic alkyl group having 1 to 16 carbon atoms; $R^{12}$ and $R^{14}$ may bond to $R^{13}$ and $R^{15}$ respectively via an oxygen atom to form a cyclic ether structure; "d", "e", "f", and "g" each represent 0 or 1; "h", "i", "j", and "k" each represent an integer of 0 to 5; $R^{16}$ represents a single bond or a linear, branched, or cyclic alkylene group having 1 to 8 carbon atoms and optionally containing a linear, branched, or cyclic alkenyl group having 2 to 10 carbon atoms, an aryl group having 6 to 14 carbon atoms, an ether group, a thiol group, a thioether group, an ester group, a lactone ring, a nitro group, or a substituted or unsubstituted hydroxyl group or carboxyl group.

The resin having the repeating unit shown by the formula (3) may be obtained by, for example, adding aldehyde to a solution containing the compound X and undergoing a condensation reaction to form a novolak. Forming a novolak increases the molecular weight, thus enabling the inhibition of generation of outgas and particles due to low molecular weight components at baking.

Examples of the aldehyde used in the reaction include formaldehyde, trioxane, paraformaldehyde, benzaldehyde, methoxybenzaldehyde, phenylbenzaldehyde, tritylbenzaldehyde, cyclohexylbenzaldehyde, cyclopentylbenzaldehyde, tert-butylbenzaldehyde, naphthalenealdehyde, hydroxynaphthalenealdehyde, anthracenealdehyde, fluorenealdehyde, pyrenealdehyde, methoxynaphthalenealdehyde, dimethoxynaphthalenealdehyde, acetaldehyde, propylaldehyde, phenylacetaldehyde, naphthaleneacetaldehyde, substituted or unsubstituted carboxylnaphthaleneacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, furfural, furancarboxaldehyde, and thiophenealdehyde. These aldehydes can be used alone or in combination of two or more kinds.

The amount of the aldehyde to be used is preferably in the range of 0.2 to 5 mol, more preferably 0.5 to 2 mol with respect to 1 mol of the compound X.

A catalyst may be used in condensation reaction of the compound X with the aldehyde. Illustrative examples thereof include acid catalysts such as hydrochloric acid, nitric acid, sulfuric acid, formic acid, oxalic acid, acetic acid, methanesulfonic acid, camphor sulfonic acid, tosic acid, and trifluoromethane sulfonic acid. The amount of the acid catalyst to be used is preferably in the range of $1 \times 10^{-5}$ to $5 \times 10^{-1}$ mol with respect to 1 mol of the compound X.

The resin having the repeating unit shown by the formula (3) is a condensate obtained by forming a novolak of a material containing the compound X. The condensate is not limited to this resin, and may be a condensate obtained by forming a novolak of a material containing the compound Y or a condensate obtained by forming a novolak of a material containing both the compound X and the compound Y. Such condensates can be synthesized in the same manner as the resin having the repeating unit shown by the formula (3) is synthesized.

To form the novolak of the compound X (or the compound Y), other monomers may be co-condensed therewith. Illustrative example of the monomer that can be co-condensed include phenol, o-cresol, m-cresol, p-cresol, 2,3-dimethyphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 4,4'-(9H-fluorene-9-ylidene)bisphenol, 2,2'dimethyl-4,4'-(9H-fluorene-9-ylidene)bisphenol, 2,2'diallyl-4,4'-(9H-fluorene-9-ylidene)bisphenol, 2,2'difluoro-4,4'-(9H-fluorene-9-ylidene)bisphenol, 2,2'diphenyl-4,4'-(9H-fluorene-9-ylidene)bisphenol, 2,2'dimethoxy-4,4'-(9H-fluorene-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,4-dihydroxynaphthalene, 2,5-dihydroxynaphthalene, 2,6-dihydroxynaphthalene, 2,7-dihydroxynaphthalene, 2,8-dihydroxynaphthalene, 1-naphthol, 2-naphthol, 2-methyl-1-naphthol, 4-methoxy-1-naphthol, 7-methoxy-2-naphthol, 6-methoxy-2-naphthol, 3-methoxy-2-naphthol, 1,4-dimethoxynaphthalene, 1,5-dimethoxynaphthalene, 1,6-dimethoxynaphthalene, 1,7-dimethoxynaphthaiene, 1,8-dimethoxynaphthalene, 2,3-dimethoxynaphthalene, 2,6-dimethoxynaphthalene, 2,7-dimethoxynaphthalene, methyl 3-hydroxy-naphthalene-2-carboxylate, naphthalene, 1-methylnaphthalene, 2-methylnaphthalene, 1,2-dimethylnaphthalene, 1,3-dimethylnaphthalene, 1,4-dimethylnaphthalene, 1,5-dimethylnaphthalene, 1,6-dimethylnaphthalene, 1,7-dimethylnaphthalene, 1,8-dimethylnaphthalene, 2,3-dimethylnaphthalene, 2,6-dimethylnaphthalene, 2,7-dimethylnaphthalene, 1-ethylnaphthalene, 2-ethylnaphthalene, 1-propylnaphthalene, 2-propylnaphthalene, 1-butylnaphthalene, 2-butylnaphthalene, 1-phenylnaphthalene, 1-cyclohexylnaphthalene, 1-cyclopentylnaphthalene, 1,1'-bi(2-naphthol), o-cresol, m-cresol, p-cresol, indene, hydroxyanthracene, acenaphthylene, acenaphthene, biphenyl, bisphenol, trisphenol, dicyclopentadiene, 6,6'-(9H-fluorene-9-ylidene)bis-2-naphthol, phenolphthalein, phenol red, cresolphthalein, cresol red, thymolphthalein, naphtholphthalein, fluorescein, naphthofluorescein, and carbazole.

The molecular weight of the compound X (or the compound Y) can be increased without using the aldehyde. For example, the compound X (or the compound Y) may be reacted with dicyclopentadiene to obtain a condensate; or indeno[1,2-b]fluorene-6,12-dione may be reacted with various aromatic compounds or the above monomers to obtain a condensate.

The condensate obtained by a condensation of a material containing the compound X and/or the compound Y preferably has a molecular weight of 400 to 20,000, more preferably 500 to 10,000, much more preferably 600 to 10,000 as weight average molecular weight determined by gel permeation chromatography (GPO) in terms of polystyrene. The condensate having smaller molecular weight is more excellent in filling property.

In addition, resins other than the condensate obtained by a condensation of the material containing the compound X and/or the compound Y may also be blended to the inventive resist underlayer film composition. Examples of the blendable resin include novolak resins obtained by reaction of aldehyde with a monomer such as phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 1-naphthol, 2-naphthol, 2-methyl-1-naphthol, 4-methoxy-1-naphthol, 7-methoxy-2-naphthol, dihydroxynaphthalene such as 1,5-dihydroxynaphthalene, 1,7-dihydroxynaphthalene, and 2,6-dihydroxynaphthalene, methyl 3-hydroxynaphthalene-2-carboxylate, indene, hydroxyindene, benzofuran, hydroxyanthracene, acenaphthylene, biphenyl, bisphenol, trisphenol, and bisnaphtholfluorene. Other examples include resins obtained by co-condensation of a phenol compound with dicyclopentadiene, tetrahydroindene, 4-vinylcyclohexene, norbornadiene, 5-vinylnorborna-2-ene, α-pinene, β-pinene, or limonene, without using aldehyde.

Other examples of the blendable resin include polymers obtained by polymerizing monomers selected from hydroxystyrene, alkoxystyrene, hydroxyvinylnaphthalene, alkoxyvinylnaphthalene, (meth) acrylate, vinylether, maleic anhydride, and itaconic anhydride.

The inventive resist underlayer film composition may further contain a high-carbon resin. Examples of such a resin include resins used in an underlayer film composition disclosed in Japanese Patent Laid-Open Publication No. 2004-205658, No. 2004-205676, No. 2004-205685, No. 2004-271838, No. 2004-354554, No. 2005-010431, No. 2005-

049810, No. 2005-114921, No. 2005-128509, No. 2005-250434, No. 2006-053543, No. 2006-227391, No. 2006-259249, No. 2006-259482, No. 2006-285095, No. 2006-293207, No. 2006-293298, No. 2007-140461, No. 2007-171895, No. 2007-199653, No. 2007-316282, No. 2008-026600, No. 2008-065303, No. 2008-096684, No. 2008-257188, No. 2010-160189, No. 2010-134437, No. 2010-170013, No. 2010-271654, No. 2008-116677, and No. 2008-145539.

The resist underlayer film is conventionally required to be prevented from intermixing with a resist middle layer film containing silicon or the like and a resist upper layer film, such as a photoresist film, formed on the resist underlayer film and from diffusing lower molecular weight components into the resist upper layer film and the resist middle layer film. To prevent these problems, the resist underlayer film is generally crosslinked by baking after spin coating. Thus, in the case that a crosslinking agent is added to the resist underlayer film composition, a crosslinkable substituent may be introduced into the indeno[1,2-b]fluorene compound. Even if a crosslinking agent is not added, the indeno[1,2-b]fluorene compound contained in the inventive resist underlayer film composition can be crosslinked by heating at a temperature exceeding 300° C. In the case that an inorganic metallic middle layer film is formed on the resist underlayer film by CVD or sputtering, the resist underlayer film does not need to be insolubilized in a solvent, but is preferably crosslinked to prevent the resist underlayer film from deforming due to high temperature during CVD or sputtering and from generating outgas.

[Other Additives]
(Organic Solvent)

The inventive resist underlayer film may further contain an organic solvent. The organic solvent usable in the inventive resist underlayer film composition is not limited so long as it can dissolve the compound having an indenofluorene structure, later-described acid generator, crosslinking agent, and other additives. Illustrative examples thereof include ketones such as cyclohexanone, cyclopentanone, and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combination of two or more kinds, although it is not limited thereto. Among these organic solvents, diethylene glycol dimethyl ether, 1-ethoxy-2-propanol, ethyl lactate, propylene glycol monomethyl ether acetate, and a mixed solvent thereof are particularly preferable in the inventive resist underlayer film composition.

The formulation amount of the organic solvent in the inventive resist underlayer film composition is preferably 200 to 10,000 parts by mass, particularly preferably 300 to 8,000 parts by mass, based on 100 parts by mass of the compound having an indenofluorene structure.

(Acid Generator)

The inventive resist underlayer film may further contain an acid generator to promote crosslinking reaction. The acid generator includes one capable of generating an acid by thermal decomposition and one capable of generating an acid by light irradiation, and any acid generator can be added. Illustrative examples thereof include materials disclosed in paragraphs (0061) to (0085) of Japanese Patent Laid-Open Publication No. 2007-199653.

(Crosslinking Agent)

The inventive resist underlayer film may further contain a crosslinking agent to promote crosslinking reaction. Examples of the crosslinking agent include melamine compounds, guanamine compounds, glycoluril compounds, and urea compounds each substituted with at least one group selected from a methylol group, an alkoxymethyl group, and acyloxymethyl group, epoxy compounds, isocyanate compounds, azide compounds, and compounds having a double bond such as an alkenyl ether group. These crosslinking agents may be used as additives, or may be introduced into a side chain of the indeno[1,2-b]fluorene compound as a pendant group. In addition, a compound having a hydroxyl group may also be used as the crosslinking agent.

Illustrative examples of the crosslinking agent include epoxy compounds such as tris(2,3-epoxypropyl)isocyanurate, trimethylolmethane triglycidyl ether, trimethylolpropane triglycidyl ether, and triethylolethane triglycidyl ether; melamine compounds such as hexamethylol melamine, hexamethoxymethyl melamine, a hexamethylol melamine compound in which 1 to 6 methylol groups are methoxymethylated, a mixture thereof, hexamethoxyethyl melamine, hexaacyloxymethyl melamine, and a hexamethylol melamine compound in which 1 to 6 methylol groups are acyloxymethylated, and a mixture thereof; guanamine compounds such as tetramethylol guanamine, tetramethoxymethyl guanamine, a tetramethylol guanamine compound in which 1 to 4 methylol groups are methoxymethylated, a mixture thereof, tetramethoxyethyl guanamine, tetraacyloxy guanamine, a tetramethylol guanamine compound in which 1 to 4 methylol groups are acyloxymethylated, and a mixture thereof; glycoluril compounds such as tetramethylol glycoluril, tetramethoxy glycoluril, tetramethoxymethyl glycoluril, a tetramethylol glycoluril compound in which 1 to 4 methylol groups are methoxymethylated, a mixture thereof, a tetramethylol glycoluril compound in which 1 to 4 methylol groups are acyloxymethylated, and a mixture thereof; urea compounds such as tetramethylol urea, tetramethoxymethyl urea, a tetramethylol urea compound in which 1 to 4 methylol groups are methoxymethylated, a mixture thereof, and tetramethoxyethyl urea; isocyanate compounds such as tolylene diisocyanate, diphenylmethane diisocyanate, hexamethylene diisocyanate, and cyclohexane diisocyanate; and azide compounds such as 1,1'-biphenyl-4,4'-bisazide, 4,4'-methylidene bisazide, and 4,4'-oxybisazide.

As the crosslinking agent for forming crosslinking by an acetal group, there may be mentioned a compound having multiple enolether groups within the molecule. Examples of the crosslinking agent having at least two enolether groups within the molecule include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, ethylene glycol dipropenyl ether, triethylene glycol dipropenyl ether, 1,2-propanediol dipropenyl ether, 1,4-butanedisol dipropenyl ether, tetramethylene glycol dipropenyl ether, neopentyl glycol dipropenyl ether, trimethylol propane tripropenyl ether, hexanediol dipropenyl ether, 1,4-cyclohexanediol dipropenyl ether, pentaerythritol tripropenyl ether, pentaerythritol tetrapropenyl ether, sorbitol tetrapropenyl ether, and sorbitol pentapropenyl ether.

In addition, a crosslinking agent containing an acid-labile tertiary ester group having two or more oxirane within the molecule may also be added. Illustrative examples thereof include compounds disclosed in Japanese Patent Laid-Open Publication No. 2006-096848. When such a crosslinking agent is used, the oxirane is crosslinked by heat and the tertiary ester portion is decomposed by acid, as described in Japanese Patent Laid-Open Publication No. 2001-226430.

The formulation amount of the crosslinking agent in the inventive resist underlayer film composition is preferably 0 to 50 parts by mass, more preferably 5 to 50 parts by mass, much more preferably 10 to 40 parts by mass, based on 100 parts by mass of the compound having an indenofluorene structure. In particular, when the amount is 5 parts by mass or more, mixing with a photoresist film is effectively prevented; when the amount is 50 parts by mass or less, there is no fear of lowering antireflective effect and cracking the film after crosslinking.

The compound having an indenofluorene structure (particularly, an indeno[1,2-b]fluorene structure) contained in the inventive resist underlayer film composition not only has larger molecular weight than the compound having a fluorene structure used in the conventional resist underlayer film composition, but also has twice as much crosslinking points as the conventional one. Thus, the inventive resist underlayer film composition containing such a compound generates little outgas even if only monomer components are contained therein or many monomer components are added thereto, is excellent in filling property, prevents pattern wiggling at dry etching due to high crosslinking density, and has high heat resistance.

<Patterning Process>
[2-Layer Process]

The present invention provides a patterning process for forming a pattern in a substrate by lithography, including the steps of: (A1) forming a resist underlayer film on the substrate from the inventive resist underlayer film composition; (A2) forming a photoresist film on the resist underlayer film; (A3) forming a photoresist pattern by subjecting the photoresist film to exposure and development; (A4) transferring the pattern to the resist underlayer film by dry etching using the photoresist pattern as a mask; and (A5) processing the substrate by using the resist underlayer film having the transferred pattern as a mask.

FIG. 1 is an explanatory view showing an example of the patterning process by 2-layer process of the present invention. In the patterning process of FIG. 1, a resist underlayer film 3 is formed from the inventive resist underlayer film composition on a substrate 1 on which a layer to be processed 2 has been formed (step (A1) of FIG. 1), a photoresist film 4 is formed on the resist underlayer film 3 (step (A2) of FIG. 1), the photoresist film 4 is exposed to light to form an exposed part 5 (step (A3-1) of FIG. 1), the exposed part 5 is removed by development to form a photoresist pattern 4' (step (A3-2) of FIG. 1), the pattern is transferred to the resist underlayer film 3 by dry etching using the photoresist pattern 4' as a mask (step (A4) of FIG. 1), and the layer to be processed 2 on the substrate 1 is processed by using the resist underlayer film 3 having the transferred pattern as a mask (step (A5) of FIG. 1).

In the step (A1), a resist underlayer film is formed from the inventive resist underlayer film composition on a substrate. The substrate (substrate to be processed) may be, but is not limited to, a substrate on which a layer to be processed is formed. The substrate is preferably made of a material different from the layer to be processed such as Si, α-Si, p-Si, SiO$_2$, SiN, SiON, W, TiN, and Al, although it is not particularly limited thereto. The layer to be processed is preferably made of Si, SiO$_2$, SiON, SiN, p-Si, α-Si, W, W—Si, Al, Cu, Al—Si, or the like; and various low dielectric constant (low-k) films, etching stopper films thereof, and a substrate with gaps for Fin-FET are preferably used. The thickness of the layer to be processed is preferably 10 to 10,000 nm, particularly preferably 20 to 5,000 nm.

A hard mask for processing the substrate may be formed between the substrate and the resist underlayer film. SiN, SiON, p-Si, α-Si, W, W—Si, amorphous carbon or the like is used as the hard mask when the substrate is a SiO$_2$ insulator film substrate. SiO$_2$, SiN, SiON or the like is used as the hard mask when the substrate is a gate electrode such as p-Si, W—Si, and Al—Si.

When the resist underlayer film is formed on the substrate, the inventive resist underlayer film composition is preferably applied by a spin coating method or other method, like the photoresist film described later. Good filling property can be achieved by using the spin coating method. After spin coating, baking is preferably performed to evaporate the solvent and prevent mixing with the overlying film (the photoresist film or the metallic middle layer film), to prevent heat deformation, or to promote crosslinking reaction. The baking temperature is preferably 150° C. or higher and 800° C. or lower, more preferably higher than 300° C. and 800° C. or lower, much more preferably 350° C. or higher and 700° C. or lower. The baking time is preferably 10 to 600 seconds, more preferably 10 to 300 seconds.

Baking may be carried out on a hot plate or in an electric furnace, or may be carried out by irradiation with infrared rays. In particular, a furnace, in which many wafers can be treated at once in a batch manner, allows high throughput and thus is preferable.

A novolak resin generates phenoxy radicals by heating, and methylene groups of the novolac bonds are thereby activated to crosslink the methylene groups. This radical reaction produces no releasing molecule, thus causing no film shrinkage due to crosslinking if a material having high heat resistance is used. If oxygen exists during baking, crosslinking by oxidative coupling also proceeds. To promote the crosslinking by oxidative coupling, baking may be performed in the air.

The baking may be performed in the air or may be performed in an inert gas such as N$_2$, Ar, and He to reduce oxygen. When baking is performed in the inert gas, oxidation of the resist underlayer film can be prevented, and thus the increase in absorption and the decrease in etching resistance can be prevented. Baking in the inert gas is preferably carried out at baking after crosslinking. To prevent the oxidation, oxygen concentration is preferably controlled. The oxygen concentration is preferably 1,000 ppm or less, more preferably 100 ppm or less.

The crosslinking reaction may be performed by light irradiation. In particular, irradiation with ultraviolet rays having a wavelength of 300 nm or less produces radicals. These radicals are coupled with each other, thereby promoting the crosslinking reaction. Examples of the ultraviolet ray include low-pressure mercury lamp with 254 nm wavelength, KrF excimer light with 248 nm wavelength, ArF excimer light with 193 nm wavelength, F$_2$ excimer light with 157 nm wavelength, Xe excimer light with 172 nm wavelength, Kr$_2$ excimer light with 146 nm wavelength, Are excimer light with 126 nm wavelength, and electron beam.

The thickness of the resist underlayer film to be formed is appropriately determined, and is preferably 5 to 50,000 nm, more preferably 10 to 20,000 nm, much more preferably 30 to 15,000 nm, still more preferably 50 to 10,000 nm. The thickness may be determined in view of antireflective effect.

In the step (A2), a photoresist film is formed on the resist underlayer film. The photoresist film can be formed by applying a photoresist film composition by the spin coating method or other method. As the photoresist film composition, a composition containing known hydrocarbon base polymers as disclosed in Japanese Patent Laid-Open Publication No. H09-073173 and No. 2000-336121 is suitably used. The thickness of the photoresist film is preferably, but not particularly limited to, 20 to 500 nm, particularly preferably 30 to 400 nm. The photoresist film composition is usually applied by the spin coating method or other method, and then pre-baked. The pre-baking is preferably performed, for example, at 80 to 180° C. for 10 to 300 seconds.

In addition, a resist top coat may be formed on the photoresist film. The resist top coat may have antireflective function. The resist top coat material can be classified into water-soluble one and water-insoluble one. The water-insoluble material is further classified into a material that is soluble in an alkali developer and a material that is insoluble in an alkali developer and removable with a fluorinated solvent. The former has a process advantage that the top coat can be removed at the time of development of the photoresist film. In the case of liquid immersion exposure, the resist top coat is often formed for the purpose of preventing elution of additives such as an acid generator from the photoresist film and improving water-sliding property. The resist top coat is preferably water-insoluble and alkali-soluble, and a solution in which a polymer compound having α-trifluoromethylhydroxyl group is dissolved in a higher alcohol having 4 or more carbon atoms or an ether compound having 8 to 12 carbon atoms may be used. The resist top coat can be formed by, for example, applying the resist top coat composition on the pre-baked photoresist film by spin coating and then baking it. The thickness of the resist top coat is preferably 10 to 200 nm.

In the step (A3), the photoresist film is exposed to light and developed to form a photoresist pattern. The exposure may be performed in accordance with a conventional method, and liquid immersion exposure may be employed. After exposure and before development, post-exposure baking (PEB) is preferably performed.

To fully remove water on the photoresist film before PEB, water on the photoresist film is preferably dried or recovered by suitable means, for example, spin drying prior to PEB, purging of the photoresist film surface with dry air or nitrogen, or optimizing the water recovery nozzle configuration or process on a stage after exposure. Such operations can remove water on the photoresist film, thus preventing failure in pattern formation due to water which absorbs acids in the photoresist film during PEB.

The development may be performed in accordance with a conventional method. Positive development or negative development may be appropriately selected depending on the used photoresist film composition. In the case of positive development, the following method is preferable: the development is performed by a puddling method or a dipping method with a developer of an alkali aqueous solution, followed by rinsing with pure water and drying by spin drying or nitrogen blowing. In particular, the puddling method with a 2.38 mass % tetramethylammonium hydroxide aqueous solution is preferable. The treatment time with the developer is preferably 10 to 300 seconds at room temperature.

In the case of negative development, the following method is preferable: the development is performed by a puddling method or a dipping method with a developer of an organic solvent, followed by rinsing and drying by spin drying or nitrogen blowing. Preferable organic solvent is a solvent containing one or more selected from 2-octanone, 2-nonanone, 2-heptanone, 3-heptanone, 4-heptanone, 2-hexanone, 3-hexanone, diisobutylketone, methylcyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxy-isobutyrate, ethyl 2-hydroxy-isobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. Meanwhile, the puddling method is preferable and the treatment time with the developer is preferably 10 to 300 seconds at room temperature, like the positive development.

In the case that the resist top coat that is soluble in the developer is formed on the photoresist film, the resist top coat can be removed at the time of development of the photoresist film, as mentioned above.

In the step (A4), the pattern is transferred to the resist underlayer film by dry etching using the photoresist pattern as a mask. An etching gas used in this step is preferably an oxygen-based gas.

In the step (A5), the substrate is processed by using the resist underlayer film having the transferred pattern as a mask. The substrate can be processed by, for example, transferring the pattern to the substrate by dry etching using the resist underlayer film having the transferred pattern as a mask, or implanting ions into the substrate by using the resist underlayer film having the transferred pattern as a mask although it is not particularly limited thereto.

[3-Layer Process]

Furthermore, the present invention provides a patterning process for forming a pattern in a substrate by lithography, including the steps of: (B1) forming a resist underlayer film on the substrate from the inventive resist underlayer film composition; (B2) forming a metallic middle layer film containing an element selected from the group consisting of silicon, titanium, zirconium, hafnium, tungsten, aluminum, germanium, tin, and chromium on the resist underlayer film; (B3) forming a photoresist film on the metallic middle layer film; (B4) forming a photoresist pattern by subjecting the photoresist film to exposure and development; (B5) transferring the pattern to the metallic middle layer film by dry etching using the photoresist pattern as a mask; (B6) transferring the pattern to the resist underlayer film by dry etching using the metallic middle layer film having the transferred pattern as a mask; and (B7) processing the substrate by using the resist underlayer film having the transferred pattern as a mask.

Figure 2:
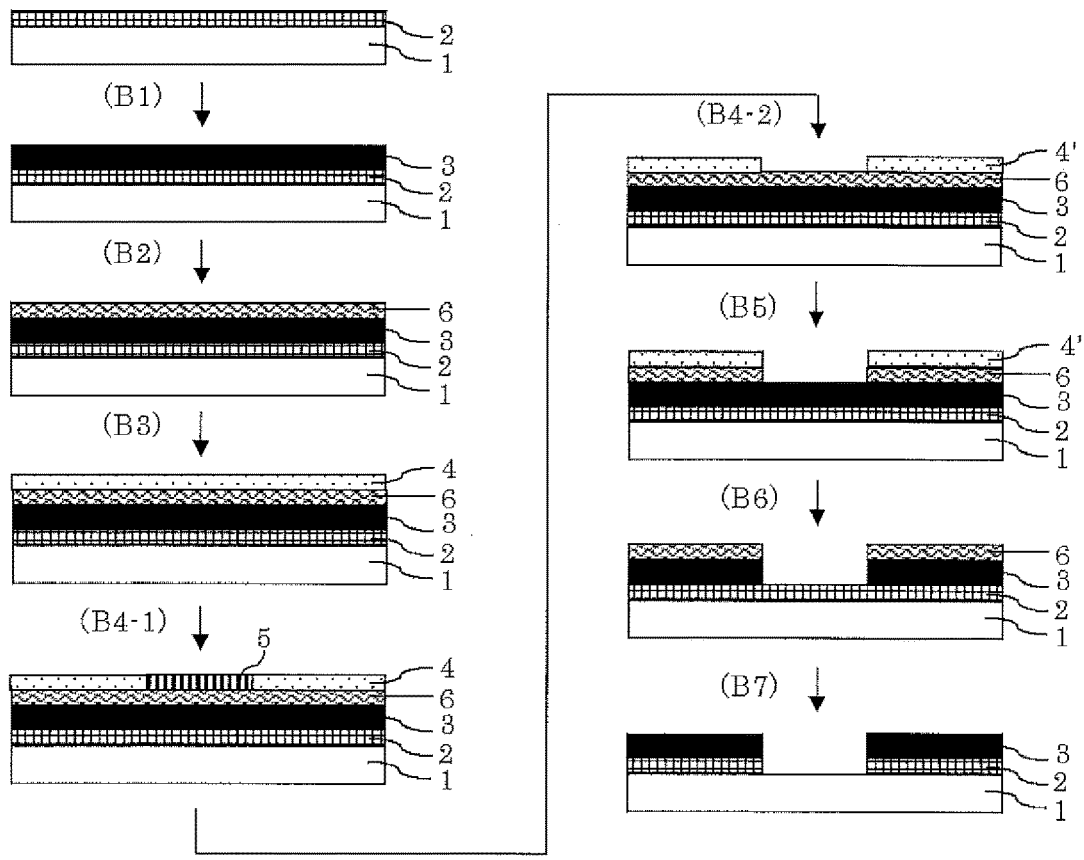
FIG. 2 is an explanatory view showing an example of the patterning process by 3-layer process of the present invention.

FIG. 2 is an explanatory view showing an example of the patterning process by 3-layer process of the present invention. In the patterning process of FIG. 2, a resist underlayer film 3 is formed from the inventive resist underlayer film composition on a substrate 1 on which a layer to be processed 2 has been formed (step (B1) of FIG. 2), a metallic middle layer film 6 is formed on the resist underlayer film 3 (step (B2) of FIG. 2), a photoresist film 4 is formed on the metallic middle layer film 6 (step (B3) of FIG. 2), the photoresist film 4 is exposed to light to form an exposed part 5 (step (B4-1) of FIG. 2), the exposed part 5 is removed by development to form a photoresist pattern 4' (step (B4-2) of FIG. 2), the pattern is transferred to the metallic middle layer film 6 by dry etching using the photoresist pattern 4' as a mask (step (B5) of FIG. 2), the pattern is transferred to the resist underlayer film 3 by dry etching using the metallic middle layer film 6 having the transferred pattern as a mask (step (B6) of FIG. 2), and the layer to be processed 2 on the substrate 1 is processed by using the resist underlayer film 3 having the transferred pattern as a mask (step (B7) of FIG. 2).

The steps (B1), (B3), (B4), and (B7) may be performed in the same manner as in the steps (A1), (A2), (A3), and (A5) in the patterning process by 2-layer process, respectively. To prevent outgas generated from the resist underlayer film, the resist underlayer film is preferably baked in the step (B1) at a temperature higher than temperature for forming the metallic middle layer film.

In the step (B2), a metallic middle layer film containing an element selected from the group consisting of silicon, titanium, zirconium, hafnium, tungsten, aluminum, germanium, tin, and chromium is formed on the resist underlayer film. The metallic middle layer film may be a metallic middle layer film formed by spin coating and baking or a metallic middle layer film formed by CVD or sputtering. As the metallic middle layer film formed by spin coating and baking, silicon oxide film is most preferable. In the case of forming a metallic middle layer film having higher dry etching resistance than the silicon oxide film, for example, a silicon nitride film, a silicon oxynitride film, a silicon carbide film, a polysilicon film, a titanium oxide film, a titanium nitride film, a zirconium oxide film, a hafnium oxide film, a tungsten film, an aluminum oxide film, a tungsten oxide film, a germanium oxide film, a tin oxide film, a chromium oxide film, a chromium film, or the like is preferably formed by CVD or sputtering.

In the 3-layer process, optimum optical constants (n-value and k-value) of the metallic middle layer film for antireflective effect are as follows: the n-value ranges from 1.5 to 1.9; the k-value ranges from 0.15 to 0.3; the film thickness ranges from 20 to 130 nm, as disclosed in Japanese Patent Laid-Open Publication No. 2006-293207. In addition, optimum optical constants (n-value and k-value) of the resist underlayer film for antireflective effect are as follows: the n-value ranges from 1.3 to 1.8; the k-value ranges from 0.2 to 0.8. In the 3-layer process, thicknesses of the metallic middle layer film and the resist underlayer film may be determined in view of these properties.

In the step (B5), the pattern is transferred to the metallic middle layer film by dry etching using the photoresist pattern as a mask. An etching gas used in this step is preferably a fluorocarbon-based gas.

In the step (B6), the pattern is transferred to the resist underlayer film by dry etching using the metallic middle layer film having the transferred pattern as a mask. An etching gas used in this step is preferably an oxygen-based gas.

[4-Layer Process]

Furthermore, the present invention provides a patterning process for forming a pattern in a substrate by lithography, including the steps of: (C1) forming a resist underlayer film on the substrate from the inventive resist underlayer film composition; (C2) forming a metallic middle layer film containing an element selected from the group consisting of silicon, titanium, zirconium, hafnium, tungsten, aluminum, germanium, tin, and chromium on the resist underlayer film; (C3) forming an organic antireflective film on the metallic middle layer film; (C4) forming a photoresist film on the organic antireflective film; (C5) forming a photoresist pattern by subjecting the photoresist film to exposure and development; (C6) transferring the pattern to the organic antireflective film and the metallic middle layer film by dry etching using the photoresist pattern as a mask; (C7) transferring the pattern to the resist underlayer film by dry etching using the metallic middle layer film having the transferred pattern as a mask; and (C8) processing the substrate by using the resist underlayer film having the transferred pattern as a mask.

FIG. 3 is an explanatory view showing an example of the patterning process by 4-layer process of the present invention. In the patterning process of FIG. 3, a resist underlayer film 3 is formed from the inventive resist underlayer film composition on a substrate 1 on which a layer to be processed 2 has been formed (step (C1) of FIG. 3), a metallic middle layer film 6 is formed on the resist underlayer film 3 (step (C2) of FIG. 3), an organic antireflective film 7 is formed on the metallic middle layer film 6 (step (C3) of FIG. 3), a photoresist film 4 is formed on the organic antireflective film 7 (step (C4) of FIG. 3), the photoresist film 4 is exposed to light to form an exposed part 5 (step (C5-1) of FIG. 3), the exposed part 5 is removed by development to form a photoresist pattern 4' (step (C5-2) of FIG. 3), the pattern is transferred to the organic antireflective film 7 and the metallic middle layer film 6 by dry etching using the photoresist pattern 4' as a mask (step (C6) of FIG. 3), the pattern is transferred to the resist underlayer film 3 by dry etching using the metallic middle layer film 6 having the transferred pattern as a mask (step (C7) of FIG. 3), and the layer to be processed 2 on the substrate 1 is processed by using the resist underlayer film 3 having the transferred pattern as a mask (step (C8) of FIG. 3).

The steps (C1), (C4), (C5), and (C8) may be performed in the same manner as in the steps (A1), (A2), (A3), and (A5) in the patterning process by 2-layer process, respectively. The steps (C2) and (C7) may be performed in the same manner as in the steps (B2) and (B6) in the patterning process by 3-layer process, respectively. To prevent outgas generated from the resist underlayer film, the resist underlayer film is preferably baked in the step (C1) at a temperature higher than temperature for forming the metallic middle layer film.

In the step (C3), an organic antireflective film is formed on the metallic middle layer film. As the organic antireflective film, any known organic antireflective film can be used without particular limitation.

In the step (C6), the pattern is transferred to the organic antireflective film and the metallic middle layer film by dry etching using the photoresist pattern as a mask. An etching gas used in this step is preferably a fluorocarbon-based gas.

[5-Layer Process]

Furthermore, the present invention provides a patterning process for forming a pattern in a substrate by lithography, including the steps of: (D1) forming a resist underlayer film on the substrate from the inventive resist underlayer film composition; (D2) forming a metallic middle layer film containing an element selected from the group consisting of silicon, titanium, zirconium, hafnium, tungsten, aluminum, germanium, tin, and chromium on the resist underlayer film; (D3) forming a hydrocarbon film on the metallic middle layer film; (D4) forming a silicon-containing film on the hydrocarbon film; (D5) forming a photoresist film on the silicon-containing film; (D6) forming a photoresist pattern by subjecting the photoresist film to exposure and development; (D7) transferring the pattern to the silicon-containing film by dry etching using the photoresist pattern as a mask; (D8) transferring the pattern to the hydrocarbon film by dry etching using the silicon-containing film having the transferred pattern as a mask; (D9) transferring the pattern to the metallic middle layer film by dry etching using the hydrocarbon film having the transferred pattern as a mask; (D10) transferring the pattern to the resist underlayer film by dry etching using the metallic middle layer film having the transferred pattern as a mask; and (D11) processing the substrate by using the resist underlayer film having the transferred pattern as a mask.

FIG. 4 is an explanatory view showing an example of the patterning process by 5-layer process of the present invention. In the patterning process of FIG. 4, a resist underlayer film 3 is formed from the inventive resist underlayer film composition on a substrate 1 on which a layer to be processed 2 has been formed (step (D1) of FIG. 4), a metallic middle layer film 6 is formed on the resist underlayer film 3 (step (D2) of FIG. 4), a hydrocarbon film 8 is formed on the metallic middle layer film 6 (step (D3) of FIG. 4), a silicon-containing film 9 is formed on the hydrocarbon film 8 (step (D4) of FIG. 4), a photoresist film 4 is formed on the silicon-containing film 9 (step (D5) of FIG. 4), the photoresist film 4 is exposed to light to form an exposed part 5 (step (D6-1) of FIG. 4), the exposed part 5 is removed by development to form a photoresist pattern 4' (step (D6-2) of FIG. 4), the pattern is transferred to the silicon-containing film 9 by dry etching using the photoresist pattern 4' as a mask (step (D7) of FIG. 4), the pattern is transferred to the hydrocarbon film 8 by dry etching using the silicon-containing film 9 having the transferred pattern as a mask (step (D8) of FIG. 4), the pattern is transferred to the metallic middle layer film 6 by dry etching using the hydrocarbon film 8 having the transferred pattern as a mask (step (D9) of FIG. 4), the pattern is transferred to the resist underlayer film 3 by dry etching using the metallic middle layer film 6 having the transferred pattern as a mask (step (D10) of FIG. 4), and the layer to be processed 2 on the substrate 1 is processed by using the resist underlayer film 3 having the transferred pattern as a mask (step (D11) of FIG. 4).

The steps (D1), (D5), (D6), and (D11) may be performed in the same manner as in the steps (A1), (A2), (A3), and (A5) in the patterning process by 2-layer process, respectively. The steps (D2) and (D10) may be performed in the same manner as in the steps (B2) and (B6) in the patterning process by 3-layer process, respectively. To prevent outgas generated from the resist underlayer film, the resist underlayer film is preferably baked in the step (D1) at a temperature higher than temperature for forming the metallic middle layer film.

In the step (D3), a hydrocarbon film is formed on the metallic middle layer film. As a material for the hydrocarbon film, the inventive resist underlayer film composition may be used. Alternatively, a resist underlayer film composition containing the aforementioned high carbon resin may be used.

In the step (D4), a silicon-containing film is formed on the hydrocarbon film. A material for the silicon-containing film is preferably a material capable of forming a film by spin coating and baking, and any known materials can be used.

In the step (D7), the pattern is transferred to the silicon-containing film by dry etching using the photoresist pattern as a mask. An etching gas used in this step is preferably a fluorocarbon-based gas.

In the step (D8), the pattern is transferred to the hydrocarbon film by dry etching using the silicon-containing film having the transferred pattern as a mask. An etching gas used in this step is preferably an oxygen-based gas.

In the step (D9), the pattern is transferred to the metallic middle layer film by dry etching using the hydrocarbon film having the transferred pattern as a mask. An etching gas used in this step is preferably, a fluorocarbon-based gas or a halogen-based gas.

Thus, the inventive resist underlayer film composition can be suitably used for patterning processes by multilayer resist processes such as 2-layer process, 3-layer process, 4-layer process, and 5-layer process. Moreover, as described above, the inventive resist underlayer film composition, which is excellent in filling property, generates little outgas, and has high heat resistance, can significantly reduce defects in fine processing in a process of manufacturing semiconductor apparatuses or the like.

EXAMPLES

In the following, the present invention will be specifically described with reference to Synthesis Examples, Examples, and Comparative Examples, but the present invention is not limited thereto.

Synthesis of Indeno[1,2-b]fluorene Compound

[Synthesis Example 1] Synthesis of Compound X1

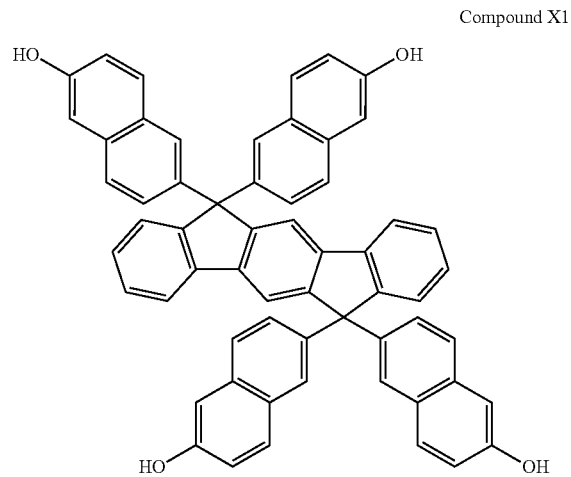 [SMILES: Oc1ccc2cc(C3(c4ccc5cc(O)ccc5c4)c4ccccc4-c4cc5c(cc43)-c3ccccc3C5(c3ccc4cc(O)ccc4c3)c3ccc4cc(O)ccc4c3)ccc2c1]

Compound X1

10.0 g of indeno[1,2-b]fluorene-6,12-dione, 40.9 g of 2-naphthol, and 150 mL of 1,2-dichloroethane were mixed to form a homogeneous solution at 50° C. in a nitrogen atmosphere. 16.1 g of methanesulfonic acid and 1.3 g of 3-mercaptopropionic acid were added dropwise thereto gently, and the mixture was stirred under heating at 60° C. for 6 hours. After cooling to room temperature, 300 g of methyl isobutyl ketone and 100 g of pure water were added thereto. An insoluble matter was then removed by filtration, the water layer was removed, and the organic layer was washed with 100 g of pure water four times. After washing, the organic layer was evaporated under reduced pressure to dryness and dissolved in 100 g of ethyl acetate. Then, it was added to 400 g of methanol to precipitate a crystal. The crystal was collected by filtration with Kiriyama funnel, washed with 100 g of methanol twice, and then dried at 60° C. under vacuum to obtain 20.3 g of Compound X1.

The obtained compound was identified as Compound X1 shown by the above structural formula by analysis with IR, $^1$H-NMR, and $^{13}$C-NMR.

IR (ATR method): ν=3327, 3059, 2972, 2929, 1632, 1604, 1541, 1506, 1480, 1442, 1384, 1370, 1275, 1250, 1216, 1195, 1174, 1151, 1098, 997, 962, 901, 875, 859, 808 cm$^{-1}$ $^1$H-NMR (600 MHz in DMSO-d$_6$): δ=9.68 (4H, —OH), 8.17 (2H, s), 7.95 (2H, d), 7.61 (4H, d), 7.57 (4H, d), 7.54 (4H, s), 7.47 (2H, d), 7.33 to 7.37 (6H, m), 7.33 (2H, T-d), 7.06 (4H, s-d), 6.99 (4H, d-d) ppm $^{13}$C-NMR (150 MHz in DMSO-d$_6$): δ=155.34, 151.18, 151.09, 139.77, 139.69, 139.55, 133.39, 129.46, 127.68, 127.57, 127.28, 127.11, 126.32, 126.16, 125.50, 120.73, 118.68, 118.10, 108.31, 64.54 ppm

[Synthesis Example 2] Synthesis of Compound X2

Compound X2

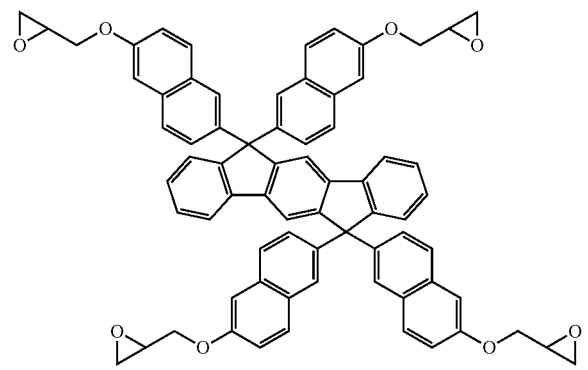

5.0 g of Compound X1, 22.5 g of epichlorohydrin, 0.05 g of tetraethylammonium chloride, and 40 g of tetrahydrofuran were mixed to form a homogeneous solution at 50° C. in a nitrogen atmosphere. After the solution was stirred at 50° C. for 6 hours, 5.0 g of sodium hydroxide was added dropwise thereto, and the solution was further stirred for 12 hours. After cooling to room temperature, 200 g of methyl isobutyl ketone and 100 g of pure water were added thereto. The water layer was then removed, and the remainder was washed with 100 g of pure water five times. After washing, the organic layer was evaporated under reduced pressure to dryness and dissolved in 40 g of methyl isobutyl ketone. Then, it was added to 200 g of diisopropyl ether to precipitate a crystal. The crystal was collected by filtration with Kiriyama funnel, washed with 80 g of diisopropyl ether twice, and then dried at 60° C. under vacuum to obtain 5.3 g of Compound X2 shown by the above structural formula. Epoxy equivalent thereof was 265 g/eq, and softening point was 175° C.

[Synthesis Example 3] Synthesis of Compound X3

Compound X3

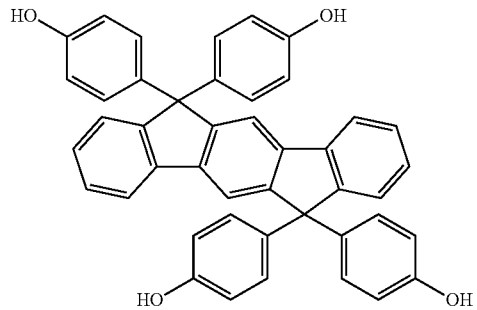

10.0 g of indeno[1,2-b]fluorene-6,12-dione, 26.7 g of phenol, and 120 mL of 1,2-dichloroethane were mixed to form a homogeneous solution at 50° C. in a nitrogen atmosphere. Then, 17.8 g of methanesulfonic acid and 1.5 g of 3-mercaptopropionic acid were added dropwise thereto gently, and the mixture was stirred under heating at 60° C. for 6 hours. After cooling to room temperature, 300 g of methyl isobutyl ketone and 100 g of pure water were added thereto. An insoluble matter was then removed by filtration, the water layer was removed, and the organic layer was washed with 100 g of pure water four times. After washing, the organic layer was evaporated under reduced pressure to dryness and dissolved in 80 g of ethyl acetate. Then, it was added to 320 g of toluene to precipitate a crystal. The crystal was collected by filtration with Kiriyama funnel, washed with 100 g of toluene twice, and then dried at 60° C. under vacuum to obtain 19.3 g of Compound X3.

The obtained compound was identified as Compound X3 shown by the above structural formula by analysis with IR, $^1$H-NMR, and $^{13}$C-NMR.

IR (ATR method): ν=3517, 3045, 1611, 1509, 1474, 1443, 1427, 1331, 1292, 1261, 1173, 1108, 873, 834 cm$^{-1}$ $^1$H-NMR (600 MHz in DMSO-d$_6$): δ=9.29 (4H, —OH), 7.85 to 7.89 (4H, m), 7.29 to 7.33 (4H, m), 7.25 (2H, t-d), 6.98 (8H, m), 6.64 (8H, m) ppm $^{13}$C-NMR (150 MHz in DMSO-d$_6$): δ=155.96, 152.01, 151.51, 139.28, 139.23, 136.12, 128.81, 127.42, 127.16, 125.90, 120.39, 117.61, 114.93, 63.30 ppm

[Synthesis Example 4] Synthesis of Compound X4

Compound X4

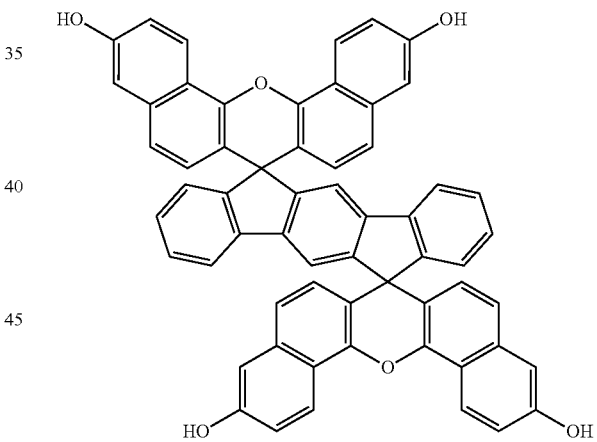

10.0 of indeno[1,2-b]fluorene-6,12-dione, 34.3 g of 1,6-dihydroxynaphthalene, and 120 mL of 1,2-dichloroethane were mixed to form a homogeneous solution at 50° C. in a nitrogen atmosphere. Then, a mixed liquid of 17.8 g of methanesulfonic acid and 1.5 g of 3-mercaptopropionic acid was added dropwise thereto gently, and the mixture was stirred under heating at 60° C. for 6 hours. After cooling to room temperature, 300 g of methyl isobutyl ketone and 100 g of pure water were added thereto. An insoluble matter was then removed by filtration, the water layer was removed, and the organic layer was washed with 100 g of pure water four times. After washing, the organic layer was evaporated under reduced pressure to dryness and dissolved in 80 g of ethyl acetate. Then, it was added to 320 g of toluene to precipitate a crystal. The crystal was collected by filtration with Kiriyama funnel, washed with 100 g of toluene twice, and then dried at 60° C. under vacuum to obtain 15.7 g of Compound X4.

The obtained compound was identified as Compound X4 shown by the above structural formula by analysis with IR, $^1$H-NMR, and $^{13}$C-NMR.

IR (ATR method): ν=3317, 3057, 1631, 1608, 1574, 1520, 1479, 1443, 1379, 1352, 1277, 1260, 1197, 1154, 1104, 953, 856, 818 cm$^{-1}$ $^1$H-NMR (600 MHz in DMSO-d$_6$): δ=8.67 (4H, d), 8.60 (4H, —OH), 7.71 to 7.74 (4H, m), 7.27 (4H, d-d), 7.08 (2H, m), 7.00 to 7.10 (12H, m), 6.35 (4H, d) ppm $^{13}$C-NMR (150 MHz in DMSO-d$_6$): δ=157.43, 157.35, 157.29, 146.94, 141.52, 140.67, 136.37, 128.65, 128.22, 126.79, 126.68, 123.85, 123.34, 120.88, 119.89, 118.87, 118.57, 116.26, 109.96, 54.68 ppm

[Synthesis Example 5] Synthesis of Condensate (Novolak Resin 1)

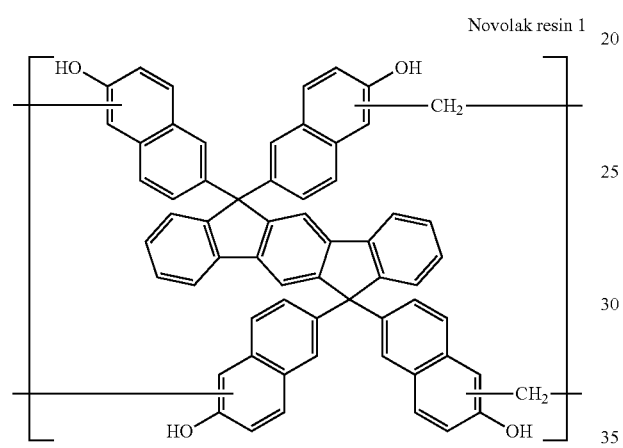

Novolak resin 1

10.0 g of Compound X1, 40 g of 1-methoxy-2-propanol, and 0.5 g of p-toluenesulfonic acid monohydride were mixed to form a homogeneous solution at 80° C. in a nitrogen atmosphere. 0.5 g of 37% formalin was added dropwise thereto gently, and the mixture was stirred at 100° C. for 12 hours. After cooling to room temperature, 200 g of methyl isobutyl ketone and 100 g of pure water were added thereto. An insoluble matter was then removed by filtration, the water layer was removed, and the organic layer was washed with 100 g of pure water four times. After washing, the organic layer was evaporated under reduced pressure to dryness to obtain 9.8 g of Novolak resin 1 consisting of a repeating unit shown by the above formula. The molecular weight (Mw) and dispersity (Mw/Mn) were determined by GPC, resulting in Mw=3,100 and Mw/Mn=3.23.

[Compound X5]

As Compound X5, indeno[1,2-b]fluorene-6,12-dione (available from Sigma-Aldrich Co.) shown by the following structural formula was prepared.

Compound X5

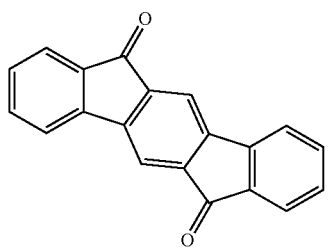

[Comparative Novolak Resin and Comparative Monomer]

Comparative novolak resins 1 and 2 having the following repeating units and Comparative monomers 1 and 2 shown by the following structural formulae were prepared to be used in Comparative Examples instead of the Compounds X1 to X5 and Novolak resin 1.

(Comparative Novolak Resin 1)

Molecular weight (Mw)=6,800

Dispersity (Mw/Mn)=5.53

Comparative novolak resin 1

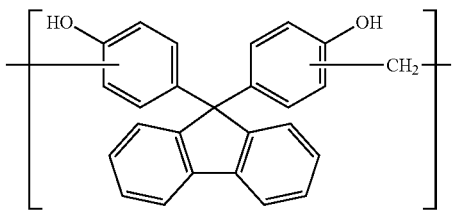

(Comparative Novolak Resin 2)

Molecular weight (Mw)=3,200

Dispersity (Mw/Mn)=4.31

Comparative novolak resin 2

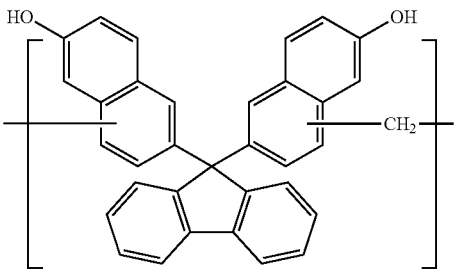

(Comparative Monomer 1)

Comparative monomer 1

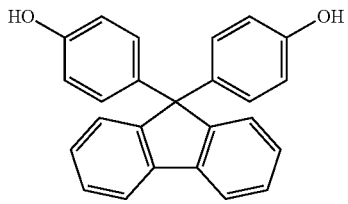

(Comparative Monomer 2)

Comparative monomer 2

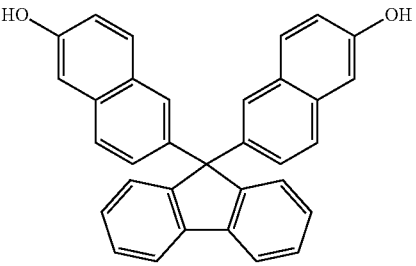

[Blend Underlayer Film Monomer]

Blend underlayer film monomers 1 to 3 shown below were prepared as monomers to be blended in the resist underlayer film composition.

(Blend Underlayer Film Monomer 1)

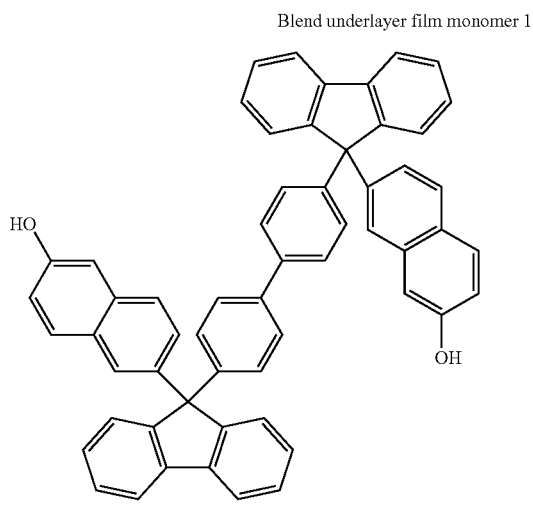 [SMILES: Oc1ccc2cc(C3(c4ccc(-c5ccc(C6(c7ccc8ccc(O)cc8c7)c7ccccc7-c7ccccc76)cc5)cc4)c4ccccc4-c4ccccc43)ccc2c1]

Blend underlayer film monomer 1

(Blend Underlayer Film Monomer 2)

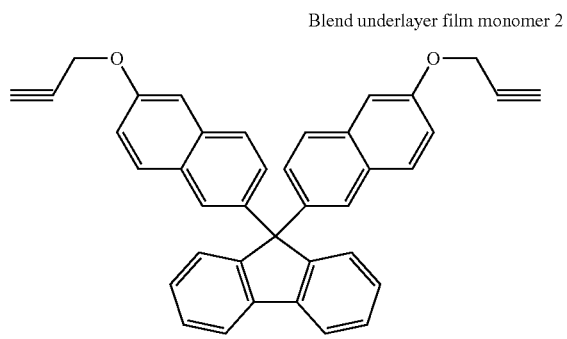 [SMILES: C#CCOc1ccc2cc(C3(c4ccc5cc(OCC#C)ccc5c4)c4ccccc4-c4ccccc43)ccc2c1]

Blend underlayer film monomer 2

(Blend Underlayer Film Monomer 3)

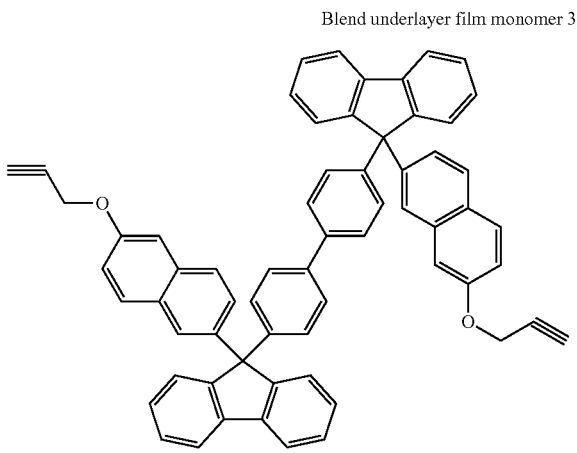 [SMILES: C#CCOc1ccc2cc(C3(c4ccc(-c5ccc(C6(c7ccc8ccc(OCC#C)cc8c7)c7ccccc7-c7ccccc76)cc5)cc4)c4ccccc4-c4ccccc43)ccc2c1]

Blend underlayer film monomer 3

EXAMPLES AND COMPARATIVE EXAMPLES

[Preparation of Resist Underlayer Film Composition]

Compounds X1 to X5, Novolak resin 1, Blend underlayer film monomers 1 to 3, Comparative novolak resins 1 and 2, Comparative monomers 1 and 2, and the following acid generator TAG1 were dissolved in an organic solvent containing 0.1 mass % FC-4430 (available from Sumitomo 3M Ltd.) with the proportion shown in Table 1. The solution was filtered through a 0.1-μm filter made of a fluorinated resin to prepare resist underlayer film compositions (Underlayer film compositions 1 to 9 and Comparative underlayer film compositions 1 to 4).

Thermal Acid Generator: TAG1

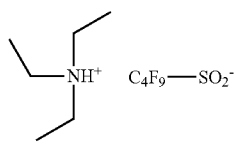

TAG1

Organic solvent: PGMEA (propylene glycol monomethyl ether acetate)

CyH (Cyclohexane)

[Measurement of Refractive Index of Resist Underlayer Film]

Underlayer film compositions 1 to 9 and Comparative underlayer film compositions 1 to 4 thus prepared were each applied onto a silicon substrate, baked on a hot plate at 350° C. for 60 seconds in the air, and further baked on a hot plate at 450° C. for 60 seconds in a nitrogen gas stream to form a resist underlayer film with a thickness of 80 nm (Examples 1-1 to 1-9 and Comparative Examples 1-1 to 1-4). After formation of the resist underlayer film, refractive index (n-value and k-value) at 193 nm wavelength was measured by a spectroscopic ellipsometer with a variable incident light angle (VASE) manufactured by J. A. Woollam Co., Inc. The result is given in Table 1.

TABLE 1

| Resist underlayer film composition | | Polymer (part by mass) | Monomer (part by mass) | Acid generator/ crosslinking agent (part by mass) | Organic solvent (part by mass) | n-value | k-value |
|---|---|---|---|---|---|---|---|
| Example 1-1 | Underlayer film composition 1 | Novolak resin 1 (50) | Compound X5 (50) | TAG1 (2.0) | PGMEA (2,000) CyH (500) | 1.38 | 0.42 |
| Example 1-2 | Underlayer film composition 2 | — | Compound X1 (100) | — | PGMEA (2,500) | 1.40 | 0.43 |
| Example 1-3 | Underlayer film composition 3 | — | Compound X2 (100) | — | PGMEA (2,500) | 1.41 | 0.49 |
| Example 1-4 | Underlayer film composition 4 | Novolak resin 1 (30) | Compound X3 (70) | — | PGMEA (2,500) | 1.37 | 0.43 |
| Example 1-5 | Underlayer film composition 5 | — | Compound X4 (100) | — | PGMEA (2,500) | 1.44 | 0.48 |
| Example 1-6 | Underlayer film composition 6 | Comparative novolak resin 2 (10) | Compound X1 (90) | — | PGMEA (2,500) | 1.48 | 0.44 |
| Example 1-7 | Underlayer film composition 7 | — | Compound X5 (50) Blend underlayer film monomer 1 (50) | — | PGMEA (2,500) | 1.42 | 0.42 |
| Example 1-8 | Underlayer film composition 8 | — | Compound X5 (60) Blend underlayer film monomer 2 (40) | — | PGMEA (2,500) | 1.43 | 0.42 |
| Example 1-9 | Underlayer film composition 9 | — | Compound X5 (70) Blend underlayer film monomer 3 (30) | — | PGMEA (2,500) | 1.44 | 0.43 |
| Comparative Example 1-1 | Comparative underlayer film composition 1 | Comparative novolak resin 1 (30) | Comparative monomer 2 (70) | — | PGMEA (2,500) | 1.43 | 0.52 |
| Comparative Example 1-2 | Comparative underlayer film composition 2 | Comparative novolak resin 2 (30) | Comparative monomer 1 (70) | — | PGMEA (4,000) | 1.38 | 0.69 |
| Comparative Example 1-3 | Comparative underlayer film composition 3 | Comparative novolak resin 2 (30) | Comparative monomer 2 (70) | — | PGMEA (4,000) | 1.39 | 0.44 |
| Comparative Example 1-4 | Comparative underlayer film composition 4 | Comparative novolak resin 2 (70) | Comparative monomer 2 (30) | — | PGMEA (4,000) | 1.39 | 0.43 |

As shown in Table 1, the resist underlayer films in Examples 1-1 to 1-9 had refractive index, a n-value of 1.3 to 1.6 and a k-value of 0.3 to 0.7. These values are equivalent to the n-value and the k-value of the conventional resist underlayer films (Comparative Examples 1-1 to 1-4). This result indicates that the resist underlayer film formed from the inventive resist underlayer film composition has optimum refractive index (n-value) and extinction coefficient (k-value) to exhibit a sufficient antireflective effect, like the conventional resist underlayer film.

[Preparation of Silicon-Containing Middle Layer Film Composition]

A resin shown by the following ArF silicon-containing middle layer film polymer 1 and crosslinking catalyst 1 were dissolved in an organic solvent containing 0.1 mass % FC-4430 (available from Sumitomo 3M Ltd.) with the proportion shown in Table 2. The solution was filtered through a 0.1-μm filter made of a fluorinated resin to prepare Silicon-containing middle layer film composition 1.

ArF Silicon-Containing Middle Layer Film Polymer 1

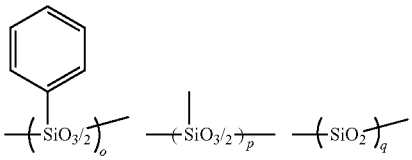

ArF silicon-containing middle layer film polymer 1
(o = 0.20, p = 0.50, q = 0.30 Mw = 3,400)

Crosslinking Catalyst 1

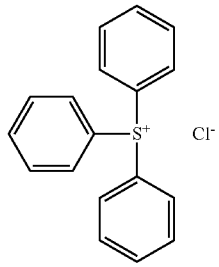

Crosslinking catalyst 1

Organic solvent: PGEE (propylene glycol monoethyl ether)

[Measurement of Refractive Index of Silicon-Containing Middle Layer Film]

Silicon-containing middle layer film composition 1 thus prepared was applied onto a silicon substrate, baked at 200° C. for 60 seconds to form a silicon-containing middle layer film with a thickness of 40 nm. After formation of the silicon-containing middle layer film, refractive index (n-value and k-value) at 193 nm wavelength was measured by a spectroscopic ellipsometer with a variable incident light angle (VASE) manufactured by J. A. Woollam Co., Inc. The result is given in Table 2.

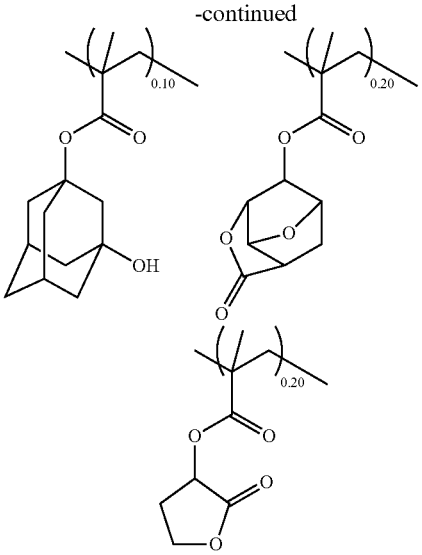

Water-Repellent Polymer 1
Molecular weight (Mw)=9,500
Dispersity (Mw/Mn)=1.69

TABLE 2

| Silicon-containing middle layer film composition | Polymer (part by mass) | Crosslinking catalyst (part by mass) | Organic solvent (part by mass) | n-value | k-value |
|---|---|---|---|---|---|
| Silicon-containing middle layer film composition 1 | ArF Silicon-containing middle layer film polymer 1 (100) | Crosslinking catalyst 1 (1.0) | PGEE (4,000) | 1.61 | 0.25 |

[Preparation of Resist Upper Layer Film Composition]

The following resist polymer 1, water-repellent polymer 1, acid generator PAG1, and Quencher 1 were dissolved in an organic solvent containing 0.1 mass % FC-4430 (available from Sumitomo 3M Ltd.) with the proportion shown in Table 3. The solution was filtered through a 0.1-μm filter made of a fluorinated resin to prepare a resist upper layer film composition for ArF exposure (ArF resist 1).

Resist Polymer 1
Molecular weight (Mw)=7,500
Dispersity (Mw/Mn)=1.92

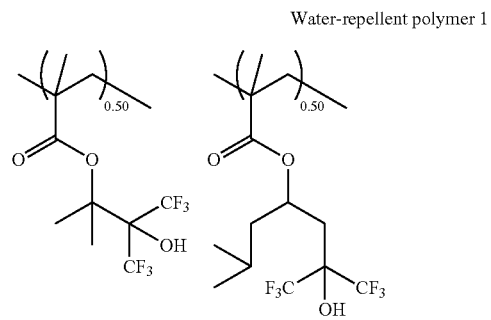

Water-repellent polymer 1

Resist polymer 1

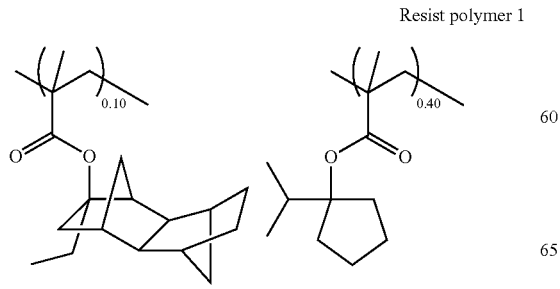

Photo Acid Generator: PAG1

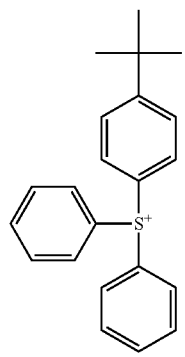

PAG1

-continued

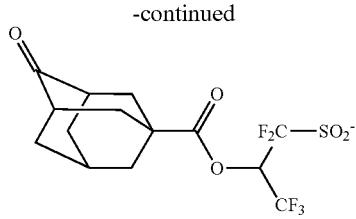

Quencher: Quencher 1

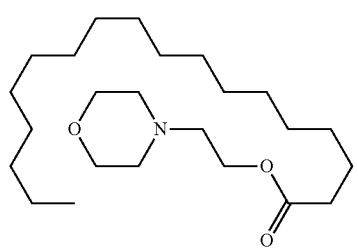

Quencher 1

Organic Solvent: GBL (γ-Butyrolactone)

TABLE 3

| Resist upper layer film composition | Polymer (part by mass) | Water-repellent polymer (part by mass) | Acid generator (part by mass) | Quencher (part by mass) | Organic solvent (part by mass) |
|---|---|---|---|---|---|
| ArF resist 1 | Resist polymer 1 (100) | Water-repellent polymer 1 (5) | PAG 1 (10.0) | Quencher 1 (2.5) | PGMEA (2,250) GBL (250) |

[Pattern Etching Test]

The resist underlayer film compositions (Underlayer film compositions 1 to 9 and Comparative underlayer film compositions 1 to 4) were each applied onto a 300-mm diameter Si wafer substrate having a $SiO_2$ film 100 nm thick, baked at 350° C. for 60 seconds in the air, and further baked at 450° C. for 60 seconds in a nitrogen gas stream to form a resist underlayer film with a thickness of 80 nm. Silicon-containing middle layer film composition 1 was applied thereon and baked at 200° C. for 60 seconds to form a silicon-containing middle layer film with a thickness of 35 nm. ArF resist 1 was applied thereon and baked at 105° C. for 60 seconds to form a photoresist film with a thickness of 80 nm. Then, the photoresist film was exposed to light with an ArF liquid immersion exposure apparatus (NSR-S610C manufactured by Nikon Corporation, NA: 1.30, a: 0.98/0.65, 35° dipole s-polarized illumination, 6% halftone phase shift mask), baked at 100° C. for 60 seconds (PEB), and developed with a 2.38 mass % tetramethylammonium hydroxide (TMAH) aqueous solution for 30 seconds to obtain a 40-nm 1:1 positive line and space pattern.

Then, the pattern was transferred to the silicon-containing middle layer film by dry etching using the formed photoresist pattern as a mask under the following condition. The pattern was then transferred to the resist underlayer film by dry etching using the transferred pattern (silicon-containing middle layer film pattern) as a mask under the following condition. The pattern was then transferred to the $SiO_2$ film by dry etching using the transferred pattern (resist underlayer film pattern) as a mask under the following condition. The cross-section of the pattern in each step was observed with an electron microscope (S-4700) manufactured by Hitachi, Ltd., to compare pattern profiles and the presence or absence of pattern wiggling after transfer to the substrate. The result is given in Table 4.

The etching conditions were as follows. For dry etching, an etching apparatus Telius manufactured by Tokyo Electron Ltd., was used.

(Condition for Transferring Photoresist Pattern to Silicon-Containing Middle Layer Film)

| | |
|---|---|
| Chamber pressure | 10.0 Pa |
| RF power | 1,500 W |
| $CF_4$ gas flow rate | 15 sccm (mL/min) |
| $O_2$ gas flow rate | 75 sccm (mL/min) |
| Treatment time | 15 sec |

(Condition for Transferring Silicon-Containing Middle Layer Film Pattern to Resist Underlayer Film)

| | |
|---|---|
| Chamber pressure | 2.0 Pa |
| RF power | 500 W |
| Ar gas flow rate | 75 sccm (mL/min) |
| $O_2$ gas flow rate | 45 sccm (mL/min) |
| Treatment time | 120 sec |

(Condition for Transferring Resist Underlayer Film Pattern to $SiO_2$ Film)

| | |
|---|---|
| Chamber pressure | 2.0 Pa |
| RF power | 2,200 W |
| $C_5F_{12}$ gas flow rate | 20 sccm (mL/min) |
| $C_2F_6$ gas flow rate | 10 sccm (mL/min) |
| Ar gas flow rate | 300 sccm (mL/min) |
| $O_2$ gas flow rate | 60 sccm (mL/min) |
| Treatment time | 90 sec |

TABLE 4

| | Resist underlayer film composition | Resist upper layer film composition | Pattern profile after development | Pattern profile after transfer to middle layer film | Pattern profile after transfer to underlayer film | Pattern profile after transfer to substrate | Pattern wiggling after transfer to substrate |
|---|---|---|---|---|---|---|---|
| Example 2-1 | Underlayer film composition 1 | ArF resist 1 | Vertical profile | Vertical profile | Vertical profile | Vertical profile | Absent |
| Example 2-2 | Underlayer film composition 2 | ArF resist 1 | Vertical profile | Vertical profile | Vertical profile | Vertical profile | Absent |
| Example 2-3 | Underlayer film composition 3 | ArF resist 1 | Vertical profile | Vertical profile | Vertical profile | Vertical profile | Absent |
| Example 2-4 | Underlayer film composition 4 | ArF resist 1 | Vertical profile | Vertical profile | Vertical profile | Vertical profile | Absent |
| Example 2-5 | Underlayer film composition 5 | ArF resist 1 | Vertical profile | Vertical profile | Vertical profile | Vertical profile | Absent |
| Example 2-6 | Underlayer film composition 6 | ArF resist 1 | Vertical profile | Vertical profile | Vertical profile | Vertical profile | Absent |
| Example 2-7 | Underlayer film composition 7 | ArF resist 1 | Vertical profile | Vertical profile | Vertical profile | Vertical profile | Absent |
| Example 2-8 | Underlayer film composition 8 | ArF resist 1 | Vertical profile | Vertical profile | Vertical profile | Vertical profile | Absent |
| Example 2-9 | Underlayer film composition 9 | ArF resist 1 | Vertical profile | Vertical profile | Vertical profile | Vertical profile | Absent |
| Comparative Example 2-1 | Comparative underlayer film composition 1 | ArF resist 1 | Vertical profile | Vertical profile | Vertical profile | Tapered profile Film loss occurs | Present |
| Comparative Example 2-2 | Comparative underlayer film composition 2 | ArF resist 1 | Vertical profile | Vertical profile | Vertical profile | Vertical profile | Present |
| Comparative Example 2-3 | Comparative underlayer film composition 3 | ArF resist 1 | Vertical profile | Vertical profile | Vertical profile | Vertical profile | Absent |
| Comparative Example 2-4 | Comparative underlayer film composition 4 | ArF resist 1 | Vertical profile | Vertical profile | Vertical profile | Vertical profile | Absent |

As shown in Table 4, Examples 2-1 to 2-9, in which the resist underlayer film was formed from the inventive resist underlayer film composition, demonstrated that the cross-section of the pattern in each step had vertical profile, and pattern wiggling did not occur after transfer to the substrate. By contrast, Comparative Example 2-1, in which the resist underlayer film was formed from the conventional resist underlayer film composition, demonstrated that the pattern had tapered profile after transfer to the substrate, and film loss occurred. Moreover, in Comparative Examples 2-1 and 2-2, pattern wiggling occurred after transfer to the substrate.

[Evaluation of Filling Property]

Onto a Si substrate on which a 500-nm thick $SiO_2$ film having a dense hole pattern with a diameter of 160 nm has been formed, the resist underlayer film compositions (Underlayer film compositions 1 to 9 and Comparative underlayer film compositions 1 to 4) were each applied under a condition where a film 80 nm thick can be formed on a flat substrate. After application, the substrate was baked at 350° C. for 60 seconds to form a resist underlayer film. The substrate on which the resist underlayer film has been formed was cut to observe whether the holes were filled to bottom with the resist underlayer film by a scanning electron microscope (SEM). The result is given in Table 5.

TABLE 5

| | Resist underlayer film composition | Filling property |
|---|---|---|
| Example 3-1 | Underlayer film composition 1 | Holes were filled to bottom well |
| Example 3-2 | Underlayer film composition 2 | Holes were filled to bottom well |
| Example 3-3 | Underlayer film composition 3 | Holes were filled to bottom well |
| Example 3-4 | Underlayer film composition 4 | Holes were filled to bottom well |
| Example 3-5 | Underlayer film composition 5 | Holes were filled to bottom well |
| Example 3-6 | Underlayer film composition 6 | Holes were filled to bottom well |
| Example 3-7 | Underlayer film composition 7 | Holes were filled to bottom well |
| Example 3-8 | Underlayer film composition 8 | Holes were filled to bottom well |
| Example 3-9 | Underlayer film composition 9 | Holes were filled to bottom well |

TABLE 5-continued

| | Resist underlayer film composition | Filling property |
|---|---|---|
| Comparative Example 3-1 | Comparative underlayer film composition 1 | Holes were filled to bottom well |
| Comparative Example 3-2 | Comparative underlayer film composition 2 | Holes were filled to bottom well |
| Comparative Example 3-3 | Comparative underlayer film composition 3 | Holes were filled to bottom well |
| Comparative Example 3-4 | Comparative underlayer film composition 4 | Filling failure |

As shown in Table 5, Examples 3-1 to 3-9, in which the resist underlayer film was formed from the inventive resist underlayer film composition, demonstrated that the holes were filled to bottom well. By contrast, Comparative Example 3-4, in which the resist underlayer film was formed from the conventional resist underlayer film composition, resulted in filling failure.

[Outgas Measurement]

The resist underlayer film compositions (Underlayer film compositions 1 to 9 and Comparative underlayer film compositions 1 to 4) were each applied onto a Si substrate, and baked at 350° C. for 60 seconds to form a resist underlayer film with a thickness of 80 nm. The number of particles with a size of 0.3 μm or 0.5 μm generated inside a hot plate oven during the baking at 350° C. was measured with a particle counter KR-11A, manufactured by RION Co., Ltd. The result is given in Table 6.

TABLE 6

| | Resist underlayer film composition | 0.3-μm particles | 0.5-μm particles |
|---|---|---|---|
| Example 4-1 | Underlayer film composition 1 | 8 | 2 |
| Example 4-2 | Underlayer film composition 2 | 3 | 0 |
| Example 4-3 | Underlayer film composition 3 | 1 | 0 |
| Example 4-4 | Underlayer film composition 4 | 0 | 0 |
| Example 4-5 | Underlayer film composition 5 | 1 | 0 |
| Example 4-6 | Underlayer film composition 6 | 1 | 0 |
| Example 4-7 | Underlayer film composition 7 | 8 | 2 |
| Example 4-8 | Underlayer film composition 8 | 3 | 0 |
| Example 4-9 | Underlayer film composition 9 | 1 | 0 |
| Comparative Example 4-1 | Comparative underlayer film composition 1 | 240 | 83 |
| Comparative Example 4-2 | Comparative underlayer film composition 2 | 250 | 69 |
| Comparative Example 4-3 | Comparative underlayer film composition 3 | 220 | 46 |
| Comparative Example 4-4 | Comparative underlayer film composition 4 | 30 | 5 |

As shown in Table 6, Examples 4-1 to 4-9, in which the resist underlayer film was formed from the inventive resist underlayer film composition, demonstrated that the number of particles generated during baking of the resist underlayer film was significantly reduced. By contrast, Comparative Examples 4-1 to 4-3, in which the resist underlayer film was formed from the conventional resist underlayer film composition, demonstrated that many particles were generated during baking of the resist underlayer film. In Comparative Example 4-4, more particles were generated than in Examples 4-1 to 4-9 although the number of particles was fewer than in Comparative Examples 4-1 to 4-3.

As described above, it was revealed that the inventive resist underlayer film composition could form a resist underlayer film that had optimum refractive index (n-value) and extinction coefficient (k-value) to exhibit a sufficient anti-reflective effect and was insoluble in a solvent. This resist underlayer film could be formed from the resin alone by heating at 300° C. or higher. When this resist underlayer film was used in patterning process, good pattern profile could be achieve after development and after pattern transfer to respective layers without pattern wiggling. In addition, the inventive resist underlayer film composition could prevent particles generated during baking even if many monomer components were contained therein to improve filling property. Thus, it was revealed that the inventive composition could achieve both the improvement in filling property and the reduction in outgas, which conventionally have the trade-off relationship.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A resist underlayer film composition for lithography, comprising a compound having an indenofluorene structure, wherein the compound having an indenofluorene structure is one or more compounds selected from the group consisting of: a compound X shown by the formula (2); a compound Y in which a plurality of the compounds X is bonded directly or via an arylene group having 6 to 28 carbon atoms and optionally containing an alkylene group having 1 to 10 carbon atoms; and a condensate obtained by a condensation of a material containing the compound X and/or the compound Y,

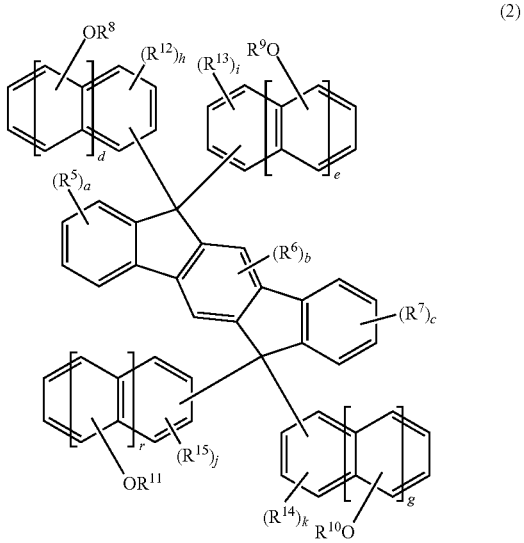

(2)

wherein
R⁵, R⁶, and R⁷ each represent a halogen atom, an amino group, a linear, branched, or cyclic alkyl group having 1 to 16 carbon atoms, a linear, branched, or cyclic alkenyl group having 2 to 10 carbon atoms, a linear, branched, or cyclic alkynyl group having 2 to 10 carbon atoms, or an aryl group having 6 to 12 carbon atoms;
"a", "b", and "c" each represent an integer of 0 to 2;
R⁸, R⁹, R¹⁰, and R¹¹ each represent a hydrogen atom, a linear, branched, or cyclic alkyl group having 1 to 16 carbon atoms, a linear, branched, or cyclic alkenyl or alkynyl group having 2 to 10 carbon atoms, an aryl group having 6 to 12 carbon atoms, a linear, branched, or cyclic acyl group having 1 to 16 carbon atoms, an acid-labile group, a group having an oxirane structure, a group having an oxetane structure, or a sulfo group;
R¹², R¹³, R¹⁴, and R¹⁵ each represent a hydroxyl group, an acyloxy group, or a linear, branched, or cyclic alkyl group having 1 to 16 carbon atoms;
R¹² and R¹⁴ may bond to R¹³ and R¹⁵ respectively via an oxygen atom to form a cyclic ether structure;
"d", "e", "f", and "g" each represent 1; and
"h", "i", "j", and "k" each represent an integer of 0 to 5.

2. The resist underlayer film composition according to claim 1, wherein the condensate is a resin having a repeating unit shown by the formula (3),

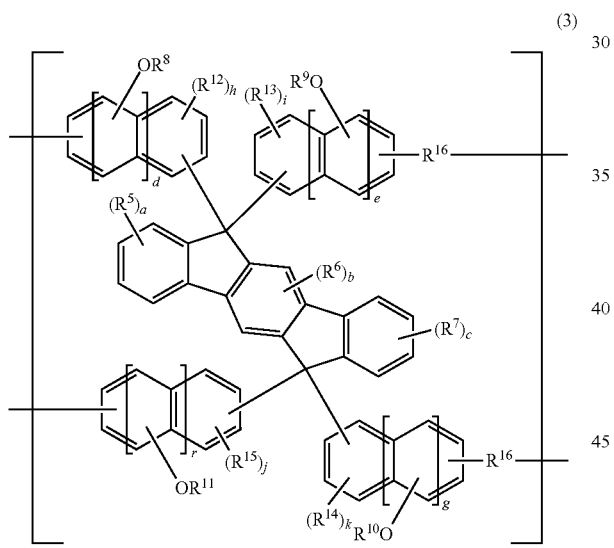

wherein R⁵, R⁶, R⁷, "a", "b" and "c" are as defined above; R⁸, R⁹, R¹⁰, and R¹¹ each represent a hydrogen atom, a linear, branched, or cyclic alkyl group having 1 to 16 carbon atoms, a linear, branched, or cyclic alkenyl or alkynyl group having 2 to 10 carbon atoms, an aryl group having 6 to 12 carbon atoms, a linear, branched, or cyclic acyl group having 1 to 16 carbon atoms, an acid-labile group, a group having an oxirane structure, a group having an oxetane structure, or a sulfo group; R¹², R¹³, R¹⁴, and R¹⁵ each represent a hydroxyl group, an acyloxy group, or a linear, branched, or cyclic alkyl group having 1 to 16 carbon atoms; R¹² and R¹⁴ may bond to R¹³ and R¹⁵ respectively via an oxygen atom to form a cyclic ether structure; "d", "e", "f", and "g" each represent 1; "h", "i", "j", and "k" each represent an integer of 0 to 5; R¹⁶ represents a single bond or a linear, branched, or cyclic alkylene group having 1 to 8 carbon atoms and optionally containing a linear, branched, or cyclic alkenyl group having 2 to 10 carbon atoms, an aryl group having 6 to 14 carbon atoms, an ether group, a thiol group, a thioether group, an ester group, a lactone ring, a nitro group, or a substituted or unsubstituted hydroxyl group or carboxyl group.

3. The resist underlayer film composition according to claim 1, further comprising an organic solvent.

4. The resist underlayer film composition according to claim 1, further comprising an acid generator and/or a crosslinking agent.

5. A patterning process for forming a pattern in a substrate by lithography, comprising the steps of:
(A1) forming a resist underlayer film on the substrate from the resist underlayer film composition according to claim 1;
(A2) forming a photoresist film on the resist underlayer film;
(A3) forming a photoresist pattern by subjecting the photoresist film to exposure and development;
(A4) transferring the pattern to the resist underlayer film by dry etching using the photoresist pattern as a mask; and
(A5) processing the substrate by using the resist underlayer film having the transferred pattern as a mask.

6. A patterning process for forming a pattern in a substrate by lithography, comprising the steps of:
(B1) forming a resist underlayer film on the substrate from the resist underlayer film composition according to claim 1;
(B2) forming a metallic middle layer film containing an element selected from the group consisting of silicon, titanium, zirconium, hafnium, tungsten, aluminum, germanium, tin, and chromium on the resist underlayer film;
(B3) forming a photoresist film on the metallic middle layer film;
(B4) forming a photoresist pattern by subjecting the photoresist film to exposure and development;
(B5) transferring the pattern to the metallic middle layer film by dry etching using the photoresist pattern as a mask;
(B6) transferring the pattern to the resist underlayer film by dry etching using the metallic middle layer film having the transferred pattern as a mask; and
(B7) processing the substrate by using the resist underlayer film having the transferred pattern as a mask.

7. A patterning process for forming a pattern in a substrate by lithography, comprising the steps of:
(C1) forming a resist underlayer film on the substrate from the resist underlayer film composition according to claim 1;
(C2) forming a metallic middle layer film containing an element selected from the group consisting of silicon, titanium, zirconium, hafnium, tungsten, aluminum, germanium, tin, and chromium on the resist underlayer film;
(C3) forming an organic antireflective film on the metallic middle layer film;
(C4) forming a photoresist film on the organic antireflective film;
(C5) forming a photoresist pattern by subjecting the photoresist film to exposure and development;
(C6) transferring the pattern to the organic antireflective film and the metallic middle layer film by dry etching using the photoresist pattern as a mask;

(C7) transferring the pattern to the resist underlayer film by dry etching using the metallic middle layer film having the transferred pattern as a mask; and (C8) processing the substrate by using the resist underlayer film having the transferred pattern as a mask.

8. A patterning process for forming a pattern in a substrate by lithography, comprising the steps of:

(D1) forming a resist underlayer film on the substrate from the resist underlayer film composition according to claim 1;

(D2) forming a metallic middle layer film containing an element selected from the group consisting of silicon, titanium, zirconium, hafnium, tungsten, aluminum, germanium, tin, and chromium on the resist underlayer film;

(D3) forming a hydrocarbon film on the metallic middle layer film;

(D4) forming a silicon-containing film on the hydrocarbon film;

(D5) forming a photoresist film on the silicon-containing film;

(D6) forming a photoresist pattern by subjecting the photoresist film to exposure and development;

(D7) transferring the pattern to the silicon-containing film by dry etching using the photoresist pattern as a mask;

(D8) transferring the pattern to the hydrocarbon film by dry etching using the silicon-containing film having the transferred pattern as a mask;

(D9) transferring the pattern to the metallic middle layer film by dry etching using the hydrocarbon film having the transferred pattern as a mask;

(D10) transferring the pattern to the resist underlayer film by dry etching using the metallic middle layer film having the transferred pattern as a mask; and (D11) processing the substrate by using the resist underlayer film having the transferred pattern as a mask.

* * * * *